United States Patent [19]

Kaibuchi et al.

[11] Patent Number: 5,906,819
[45] Date of Patent: May 25, 1999

[54] RHO TARGET PROTEIN RHO-KINASE

[75] Inventors: Kozo Kaibuchi, Ikoma; Akihiro Iwamatsu, Yokohama; Takeshi Nakano; Masaaki Ito, both of Tsu; Nobuaki Takahashi, Yokohama, all of Japan

[73] Assignee: Kirin Beer Kabushiki Kaisha, Tokyo-To, Japan

[21] Appl. No.: 08/685,576

[22] Filed: Jul. 24, 1996

[30]  Foreign Application Priority Data

Nov. 20, 1995 [JP] Japan .................................. 7-325129
Jan. 5, 1996 [JP] Japan .................................. 8-017150
Apr. 26, 1996 [JP] Japan .................................. 8-131206

[51] Int. Cl.$^6$ .............................. C12N 9/12; C12Q 1/00; A61K 38/51
[52] U.S. Cl. ............................... 424/94.5; 435/4; 435/194
[58] Field of Search ................................ 435/194, 172.1, 435/172.3, 4; 424/94.5

[56]  References Cited

PUBLICATIONS

Amano et al., "Identification of A Putative Target For Rho As The Serine–Threonine Kinase Protein Kinase N", *Science*, vol. 271:648–650, (1996).

Ando et al., "Post–Translation Processing Of rac p21s Is Important Both For Their Interaction With The GDP/GTP Exchange Proteins And For Their Activation of NADPH Oxidasde," *The Journal Of Biological Chemistry*, vol. 267(36):25709–25713, (1992).

Ando et al., "Functions And Modes of Action Of Small G Proteins", *Experimental Medicine*, vol. 11(15):1873–1979, (1993).

Bengur et al., "Sequence Of The Sites Phosphorylated By Protein Kinase C In The Smooth Muscle Myosin Light Chain", *The Journal of Biological Chemistry*, vol. 262(16):7613–7617, (1987).

Bradley et al., "Alterations In Cytoplasmic Calcium Sensitivity During Porcine Coronary Artery Contractions As Detected By Aequorin", *J. Physiol.*, vol. 385:437–448, (1987).

Bresnick et al., "Phosphorylation On Threonine–18 Of The Regulatory Light Chain Dissociates The ATPase And Motor Properties Of Smooth Muscle Myosin II", *Biochemistry*, vol. 34:12576–12583, (1995).

Brook et al., "Molecular Basis of Myotonic Dystrophy: Expansion Of A Trinucleotide (CTG) Repeat At The 3' End Of A Transcript Encoding A Protein Kinase Family Member", *Cell*, vol. 68:799–808, (1992).

Chen et al., "Molecular Cloning of cDNA Encoding The 110 kDa And 21 kDa Regulatory Subunits Of Smooth Muscle Protein Phosphatase 1M", *FEBS Letters*, vol. 356:51–55, (1994).

Chong et al., "The Small GTP–Binding Protein Rho Regulates A Phosphatidylinositol 4–Phosphate 5–Kinase In Mammalian Cells", *Cell*, vol. 79:507–513, (1994).

Collard, "Signaling Pathways Regulated By Rho–like Proteins: A Possible Role In Tumor Formation And Metastasis (Review)", *International Journal of Oncology*, vol. 8:1–8, (1996).

Drgonova et al., "Rho 1p, A Yeast Protein At The Interface Between Cell Polarization And Morphogenesis", *Science*, vol. 272:277–279, (1996).

Gong et al., "Role Of Guanine Nucleotide–Binding Proteins– Ras–family Or Trimeric Proteins Or Both–In $Ca^{2+}$ Sensitization Of Smooth Muscle", *Proc. Natl. Acad. Sci.*, vol. 93:1340–1345, (1996).

Hart et al., "Cellular Transformation And Guanine Nucleotide Exchange Activity Are Catalyzed By A Common Domain On The dbl Oncogene Product", *The Journal of Biological Chemistry*, vol. 269(1):62–65, (1994).

Hartshorne, "Biochemistry Of The Contractile Process In Smooth Muscle", *Physiology Of The Gastrointestinal Tract*, pp. 423–483.

Hathaway et al., "Selective Purification Of The 20,000–Da Light Chains Of Smooth Muscle Myosin", *Analytical Biochemistry*, vol. 135:37–43, (1983).

Hill et al., "The Rho Family GTPases RhoA, Rac1, And CDC42Hs Regulate Transcriptional Activation By SRF", *Cell*, vol. 81:1159–1170, (1995).

Hirata et al., "Involvement Of rho p21 In The GTP–Enhanced Calcium Ion Sensitivity Of Smooth Muscle Contraction", *The Journal Of Biological Chemistry*, vol. 267(13):8719–8722, (1992).

Horii et al., "A Novel Oncogene, ost, Encodes A Guanine Nucleotide Exchange Factor That Potentially Links Rho and Rac Signaling Pathways", *The EMBO Journal*, vol. 13(20):4776–4786, (1994).

Horiuchi et al., "The Posttranslational Processing Of ras p21 Is Critical For Its Stimulation Of Yeast Adenylate Cyclase", *Molecular and Cellular Biology*, vol. 12(10):4515–4520, (1992).

Huttenlocher et al., "Adhesion in Cell Migration", *Current Opinion In Cell Biology*, vol. 7:697–706, (1995).

Ikebe et al., "Phosphorylation Of Smooth Muscle Myosin At Two Distinct Sites By Myosin Light Chain Kinase", *The Journal Of Biological Chemistry*, vol. 260(18):10027–10031, (1985).

Ikebe et al., "Phosphorylation Of Bovine Platelet Myosin By Protein Kinase C", *Biochemistry*, vol. 29:2713–2720, (1990).

(List continued on next page.)

*Primary Examiner*—Robert A. Wax
*Assistant Examiner*—Einar Stole
*Attorney, Agent, or Firm*—Foley & Lardner

[57] ABSTRACT

The object of the present invention is to provide a target protein for the activated Rho protein. The present invention is a protein having activated Rho protein binding activity and protein kinase activity or derivatives thereof. The molecular weight of the protein derived from bovine is about 164 kDa as measured by SDS-PAGE. The protein kinase activity of this protein is enhanced when it binds to the activated Rho protein.

49 Claims, 25 Drawing Sheets

OTHER PUBLICATIONS

Ishizaki et al., "The Small GTP–Binding Protein Rho Binds To And Activates A 160 kDa Ser/Thr Protein Kinase Homologous To Myotonic Dystrophy Kinase", *The EMBO Journal*, vol. 15(8):1885–1893, (1996).

Itoh et al., "The Post–Translational Processing Of ras p21 Is Critical For Its Stimulation Of Mitogen–Activated Protein Kinase", *The Journal Of Biological Chemistry*, vol. 268(5):3025–3028, (1993).

Kamisoyama et al., "Mutagenesis Of The Phosphorylation Site (Serine 19) Of Smooth Muscle Myosin Regulatory Light Chain And Its Effects On The Properties Of Myosin", *Biochemistry*, vol. 33:840–847, (1994).

Kamm et al., "The Function of Myosin And Myosin Light Chain Kinase Phosphorylation In Smooth Muscle", *Ann. Rev. Pharmacol. Toxicol.*, vol. 25:593–620, (1985).

Khosravi–Far et al., "Activation Of Rac1, RhoA, And Mitogen–Activated Protein Kinases Is Required For Ras Transformation", *Molecular And Cellular Biology*, vol. 15(11):6443–6453, (1995).

Kishi et al., "Regulation Of Cytoplasmic Division Of Xenopus Embryo By rho p21 And Its Inhibitory GDP/GTP Exchange Protein (rho GDI)", *The Journal of Cell Biology*, vol. 120(5):1187–1195, (1993).

Kitazawa et al., "G Protein–Mediated Inhibition Of Myoshin Light–Chain Phosphatase In Vascular Smooth Muscle", *Proc. Natl. Acad. Sci. USA*, vol. 88:9307–9310, (1991).

Lamarche et al., "GAPs for Rho–Related GTPases", *TIG December*, vol. 10(12):436–440, (1994).

Laudanna et al., "Role of Rho In Chemoattractant–Activated Leukocyte Adhesion Through Integrins", *Science*, vol. 271:981–983, (1996).

Lebowitz et al., "Evidence That Farnesyltransferase Inhibitors Suppress Ras Transformation By Interfereing With Rho Activity", *Molecular And Cellular Biology*, vol. 15(12):6613–6622, (1995).

Leung et al., "A Novel Serine/Threonine Kinase Binding The Ras–Related RhoA GTPase Which Translocates The Kinase To Peripheral Membranes", *The Journal of Biological Chemistry*, vol. 270(49):29051–29054, (1995).

Mabuchi et al., "A Rho–Like Protein Is Involved In The Organisation Of The Contractile Ring In Dividing Sand Dollar Eggs", *Zygote*, vol. 1:325–331, (1993).

Mahadevan et al., "Myotonic Dystrophy Mutation: An Unstable CTG Repeat In The 3' Untranslated Region Of The Gene", *Science*, vol. 255:1253–1255, (1992).

Madaule et al., "A Novel Partner For The GTP–Bound Forms of rho and rac", *FEBS Letters*, vol. 377:243–248, (1995).

Matsui et al., "Identification Rho Protein Target Protein", *Seikagaku*, vol. 67(7):649, (1995).

Moe et al., "$\beta_2$–Microglobulin Induces Calcium Efflux From Cultured Neonatal Mouse Calvariae", *Am. J. Physiol.*, vol. 263:dF540–F544, (1992).

Morii et al., "A rho Gene Product In Human Blood Platelets", *The Journal of Biological Chemistry*, vol. 267(29):20921–20926, (1992).

Mukai et al., "A Novel Protein Kinase With Leucine Zipper–Like Sequences: Its Catalytic Domain Is Highly Homologous To That Of Protein Kinase C", *Biochemical And Biophysical Research Communications*, vol. 199(2):897–904, (1994).

Mukai et al., "Activation Of PKN, A Novel 120–DKa Protein Kinase With Leucine Zipper–Like Sequences, By Unsaturated Fatty Acids And By Limited Proteolysis", *Biodhemical And Biophysical Research Communications*, vol. 204(1):348–356, (1994).

Nishikawa et al., "Protein Kinase C Modulates in Vitro Phosphorylation Of The Smooth Muscle Heavy Meromyosin By Myosin Light Chain Kinase", *The Journal Of Biological Chemistry*, vol. 259(14):8808–8814, (1984).

Nishiyama et al., "Regulation of Cytoskeleton By Rho", *Experimental Medicine*, vol. 12:991–996, (1994).

Noda et al., "Involvement of rho in GTP$\gamma$S–induced Enhancement Of Phosphorylation of 20 kDa Myosin Light Chain In Vascular Smooth Muscle Cells: Inhibition Of Phosphatase Activity", *FEBS Letters*, vol. 367:246–250, (1995).

Nonaka et al., "A Downstream Target of RHO1 Small GTP–Binding Protein Is PKC1, A Homolog Of Protein Kinase C, Which Leads To Activation Of The MAP Kinase Cascade In Saccharomyces Cerevisiae", *The EMBO Journal*, vol. 14(23):5931–5938, (1995).

Nusrat et al., "Rho Protein Regulates Tight Junctions And Perijunctional Actin Organization in Polarized Epithelia", *Proc. Natl. Acad. Sci. USA*, vol. 92:10629–10633, (1995).

Paterson et al., "Microinjection Of Recombinant p21$^{rho}$ Induces Rapid Changes In Cell Morphology", *The Journal of Cell Biology*, vol. 111:1001–1007, (1990).

Prendergast et al., "Critical Role Of Rho In Cell Transformation By Oncogenic Ras", *Oncogene*, vol. 10:2289–2296, (1995).

Qadota et al., "Identification Of Yeast Rho1p GTPase As A Regulatory Subunit Of 1,3–$\beta$–Glucan Synthase", *Science*, vol. 272:279–281, (1996).

Qiu et al., "A Role For Rho In Ras Transformation", Proc. Natl. Acad. Sci. USA, vol. 92:11781–11785, (1995).

Reid et al., "Rhotekin, A New Putative Target For Rho Bearing Homology To A Serine/Threonine Kinase, PKN, And Rhophilin In The Bho–Binding Domain", *The Journal Of Biological Chemistry*, vol. 271(23):13556–13560, (1996).

Ridley et al., "The Small GTP–Binding Protein Rho Regulates The Assembly Of Focal Adhesions And Actin Stress Fibers In Response To Growth Factors", *Cell*, vol. 70:389–399, (1992).

Ridley et al., "Signal Transduction Pathways Regulating Rho–Mediated Stress Fibre Formation: Requirement For A Tyrosine Kinase", *The EMBO Journal*, vol. 13(11):2600–2610, (1994).

Sellers et al., "Regulation Of Contractile Activity", *The Enzymes*, vol. 18:381–418, (1987).

Shimizu et al., "Characterization Of The Myosin–Binding Subunit Of Smooth Muscle Myosin Phosphatase", *The Journal Of Biological Chemistry*, vol. 269(48):30407–30411, (1994).

Takai et al., "Rho As A Regulator Of The Cytoskeleton", *Trends Biochem. Sci.*, vol. 20:227–231, (1995).

Takaishi et al., "Involvement Of Rho p21 Small GTP–Binding Protein And Its Regulator In The HGF–Induced Cell Motility", *Oncogene*, vol. 9:273–279, (1994).

Tan et al., "Control Of Nonmuscle Myosins By Phosphorylation", *Annu. Rev. Biochem.*, vol. 61:721–759, (1992).

Tominaga et al., "Inhibition Of PMA–Induced, LFA–1–Dependent Lymphocyte Aggregation By ADP Ribosylation Of The Small Molecular Weight GTP Binding Protein, rho", *The Journal of Cell Biology*, vol. 120(6):1529–1537, (1993).

Yoshioka et al., "Participation Of rhop21 In Serum–Dependent Invasion By rat Ascites Hepatoma Cells", *FEBS Letters*, vol. 372:25–28, (1995).

Watanabe et al., "Protein Kinase N(PKN) And PKN–Related Protein Rhophilin As Targets Of Small GTPase Rho", *Science*, vol. 271:645–647, (1996).

Zhang et al., "Activation Of Platelet Phosphatidylinositide 3–Kinase Requires The Small GTP–Binding Protein Rho", *The Journal of Biological Chemistry*, vol. 268(30):22251–22254, (1993).

Kimura, K. et al., Science, vol. 273, pp. 245–248 (1996).

Palmer et al. (1995) Expression, purification and characterization of the ubiquitous protein kinase C–related kinase 1. Biochemical Journal 309: 315–320, Jul. 1, 1995.

Matsui et al. (1996) Rho–associated kinase, a novel serine/threonine kinase, as a putative target for the small GTP binding protein Rho. EMBO Journal 15 (9): 2208–2215, May 1, 1996.

Nakagawa et al. (1996) ROCK–I and ROCK–II, two isoforms of Rho–associated coiled–coil forming protein serine/threonine kinase in mice. FEBS Letters 392: 189–193, Sep. 26, 1996.

Ngo et al. (1994) Computational Complexity, Protein Structure Prediction, and the Levinthal Paradox, In: The Protein Folding Problem and Tertiary Structure Prediction. Eds. Merz et al. Birkhauser, Boston, MA, pp. 491–495, Jan. 1994.

Rudinger (1976) Characteristics of the amino acids as components of a peptide hormone sequence. IN: Peptide Hormones. University Park Press. Baltimore, MD, pp. 1–7, Jun. 1976.

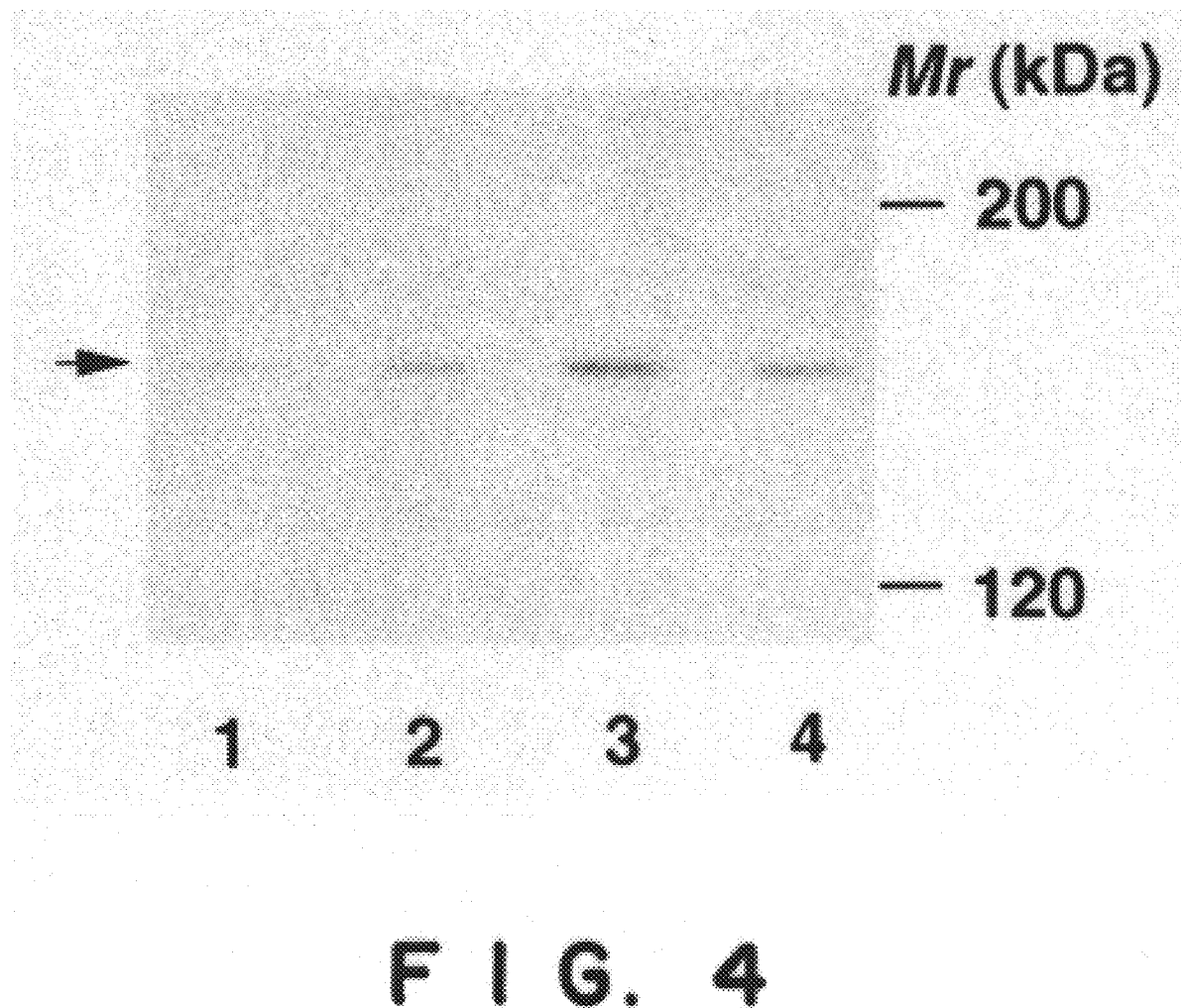
F I G. 4

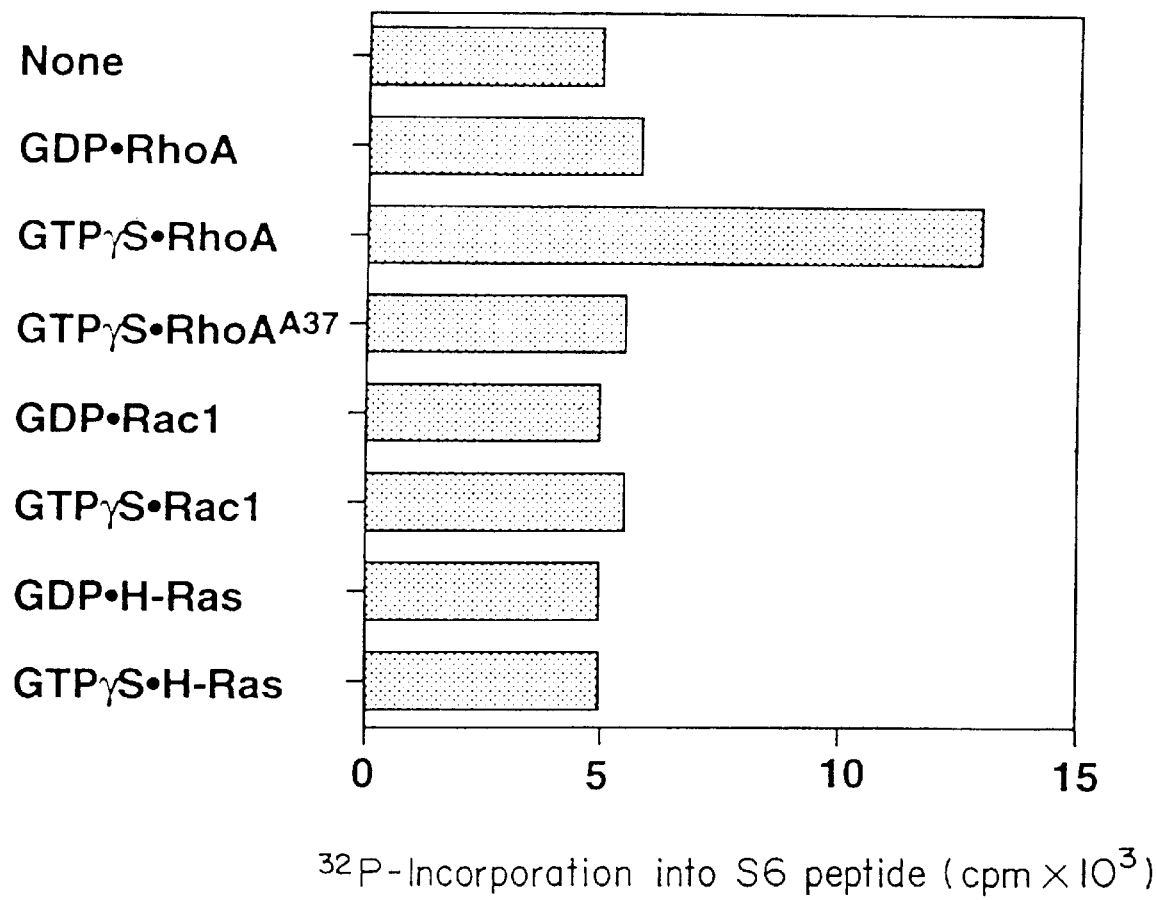
F I G. 6

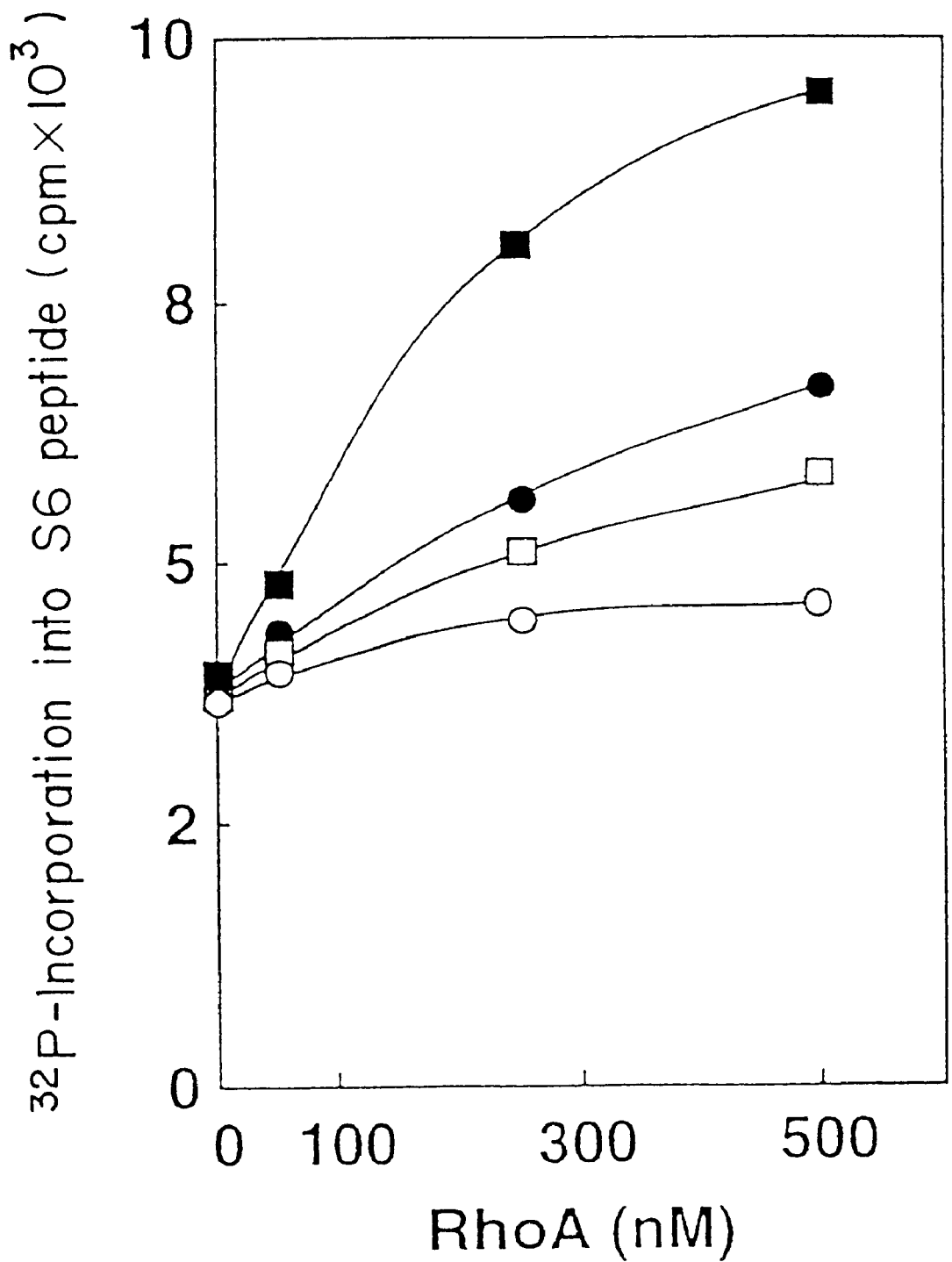
F I G. 8

```
         10         20         30         40         50         60
MSRPPPTGKM PGAPEAVSGD GAGASRQRKL EALIRDPRSP INVESLLDGL NPLVLDLDFP 70         80         90        100        110        120
ALRKNKNIDN FLNRYEKIVK KIRGLQMKAE DYDVVKVIGR GAFGEVQLVR HKASQKVYAM 130        140        150        160        170        180
KLLSKFEMIK RSDSAFFWEE RDIMAFANSP WVVQLFCAFQ DDKYLYMVME YMPGGDLVNL 190        200        210        220        230        240
MSNYDVPEKW AKFYTAEVVL ALDAIHSMGL IHRDVKPDNM LLDKHGHLKL ADFGTCMKMD 250        260        270        280        290        300
ETGMVHCDTA VGTPDYISPE VLKSQGGDGY YGRECDWWSV GVFLFEMLVG DTPFYADSLV 310        320        330        340        350        360
GTYSKIMDHK NSLCFPEDAE ISKHAKNLIC AFLTDREVRL GRNGVEEIKQ HPFFKNDQWN 370        380        390        400        410        420
WDNIRETAAP VVPELSSDID SSNFDDIEDD KGDVETFPIP KAFVGNQLPF IGFTYYRENL 430        440        450        460        470        480
LLSDSPSCKE NDSIQSRKNE ESQEIQKKLY TLEEHLSTEI QAKEELEQKC KSVNTRLEKV 490        500        510        520        530        540
AKELEEEITL RKNVESTLRQ LEREKALLQH KNAEYQRKAD HEADKKRNLE NDVNSLKDQL 550        560        570        580        590        600
EDLKKRNQNS QISTEKVNQL QRQLDETNAL LRTESDTAAR LRKTQAESSK QIQQLESNNR 610        620        630        640        650        660
DLQDKNCLLE TAKLKLEKEF INLQSVLESE RRDRTHGSEI INDLQGRISG LEEDVKNGKI 670        680        690        700        710        720
LLAKVELEKR QLQERFTDLE KEKNNMEIDM TYQLKVIQQS LEQEETEHKA TKARLADKNK 730        740        750        760        770        780
IYESIEEAKS EAMKEMEKKL SEERTLKQKV ENLLLEAEKR CSILDCDLKQ SQQKINELLK 790        800        810        820        830        840
QKDVLNEDVR NLTLKIEQET QKRCLTQNDL KMQTQQVNTL KMSEKQLKQE NNHLLEMKMS 850        860        870        880        890        900
LEKQNAELRK ERQDADGQMK ELQDQLEAEQ YFSTLYKTQV RELKEECEEK TKLCKELQQK 910        920        930        940        950        960
KQELQDERDS LAAQLEITLT KADSEQLARS IAEEQYSDLE KEKIMKELEI KEMMARHKQE 970        980        990       1000       1010       1020
LTEKDATIAS LEETNRTLTS DVANLANEKE ELNNKLKEAQ EQLSRLKDEE ISAAAIKAQF 1030       1040       1050       1060       1070       1080
EKQLLTERTL KTQAVNKLAE IMNRKEPVKR GNDTDVRRKE KENRKLHMEL KSEREKLTQQ 1090       1100       1110       1120       1130       1140
MIKYQKELNE MQAQIAEESQ IRIELQMTLD SKDSDIEQLR SQLQALHIGL DSSSIGSGPG 1150       1160       1170       1180       1190       1200
DTEADDGFPE SRLEGWLSLP VRNNTKKFGW VKKYVIVSSK KILFYDSEQD KEQSNPYMVL 1210       1220       1230       1240       1250       1260
DIDKLFHVRP VTQTDVYRAD AKEIPRIFQI LYANEGESKK EQEFPVEPVG EKSNYICHKG 1270       1280       1290       1300       1310       1320
HEFIPTLYHF PTNCEACMKP LWHMFKPPPA LECRRCHIKC HKDHMDKKEE IIAPCKVYYD 1330       1340       1350       1360       1370       1380
ISSAKNLLLL ANSTEEQQKW VSRLVKKIPK KPPAPDPFAR SSPRTSMKIQ QNQSIRRPSR 1390       1400       1410       1420       1430       1440
QLAPNKPS
```

FIG. 9

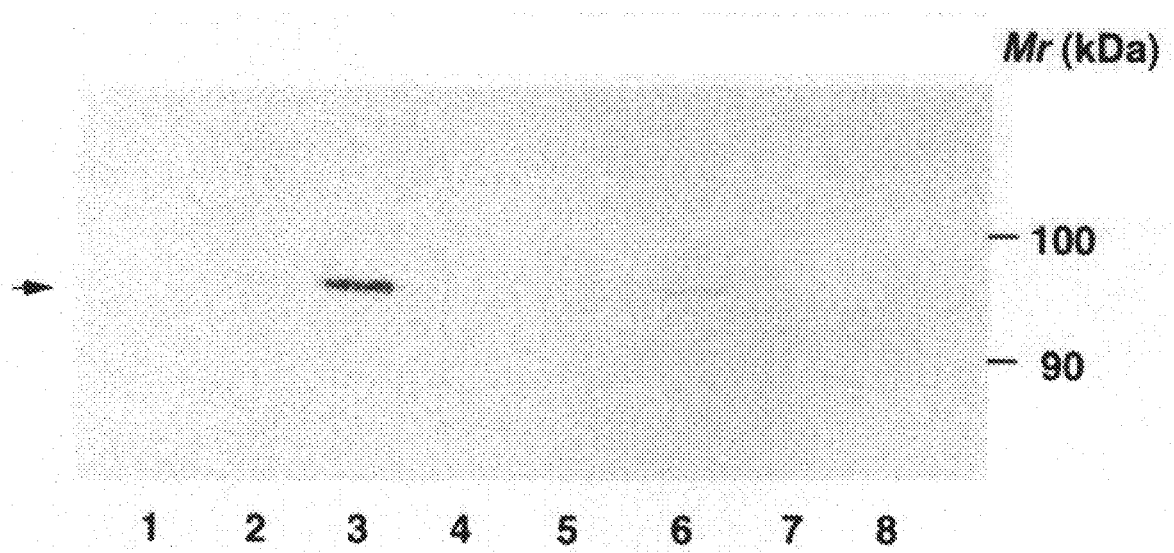
F I G. 12

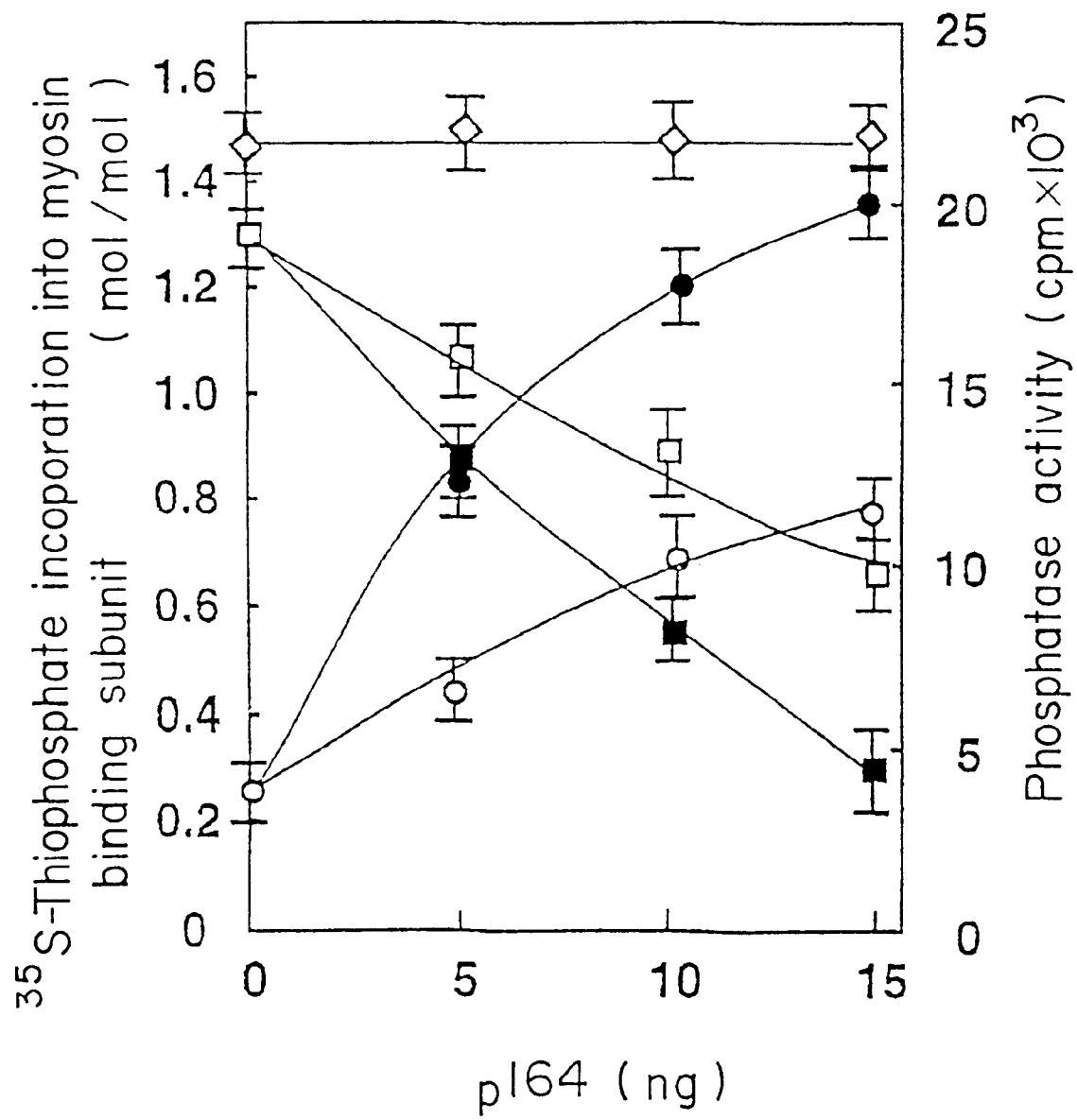
F I G. 14

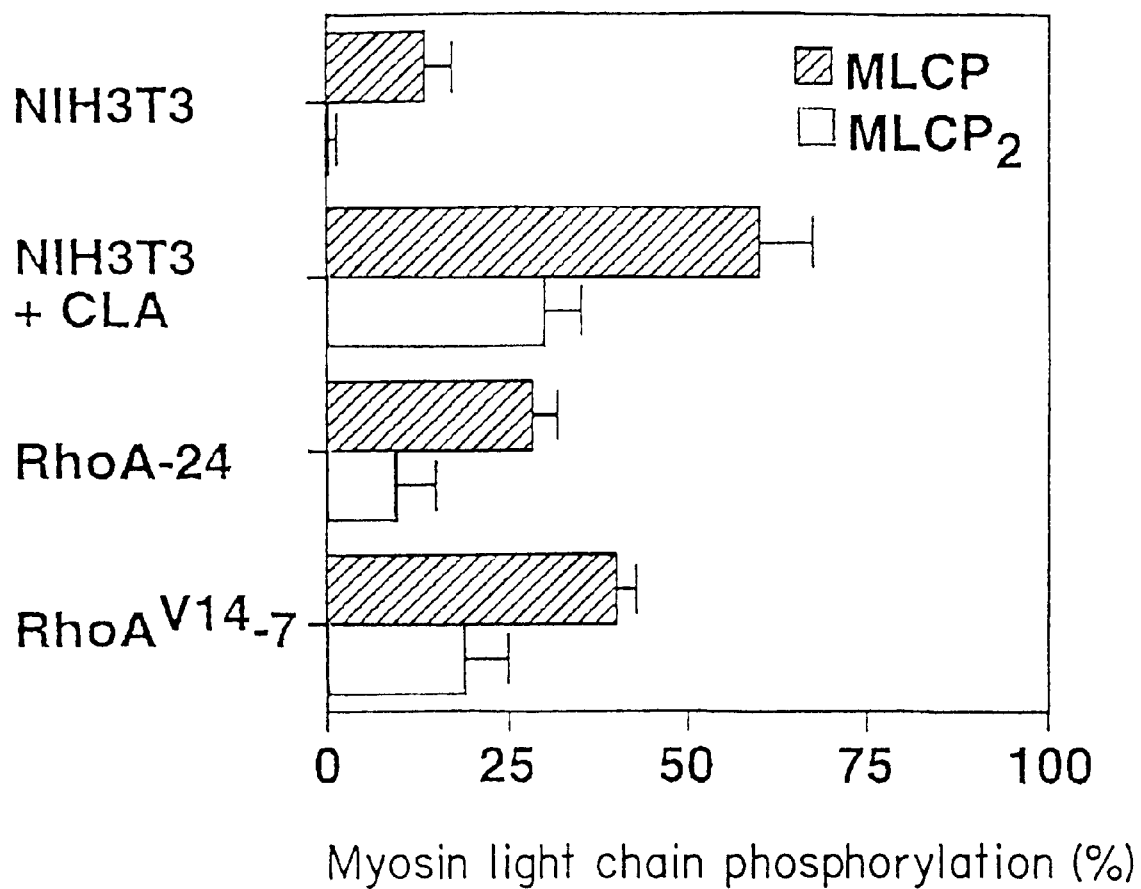
F I G. 16

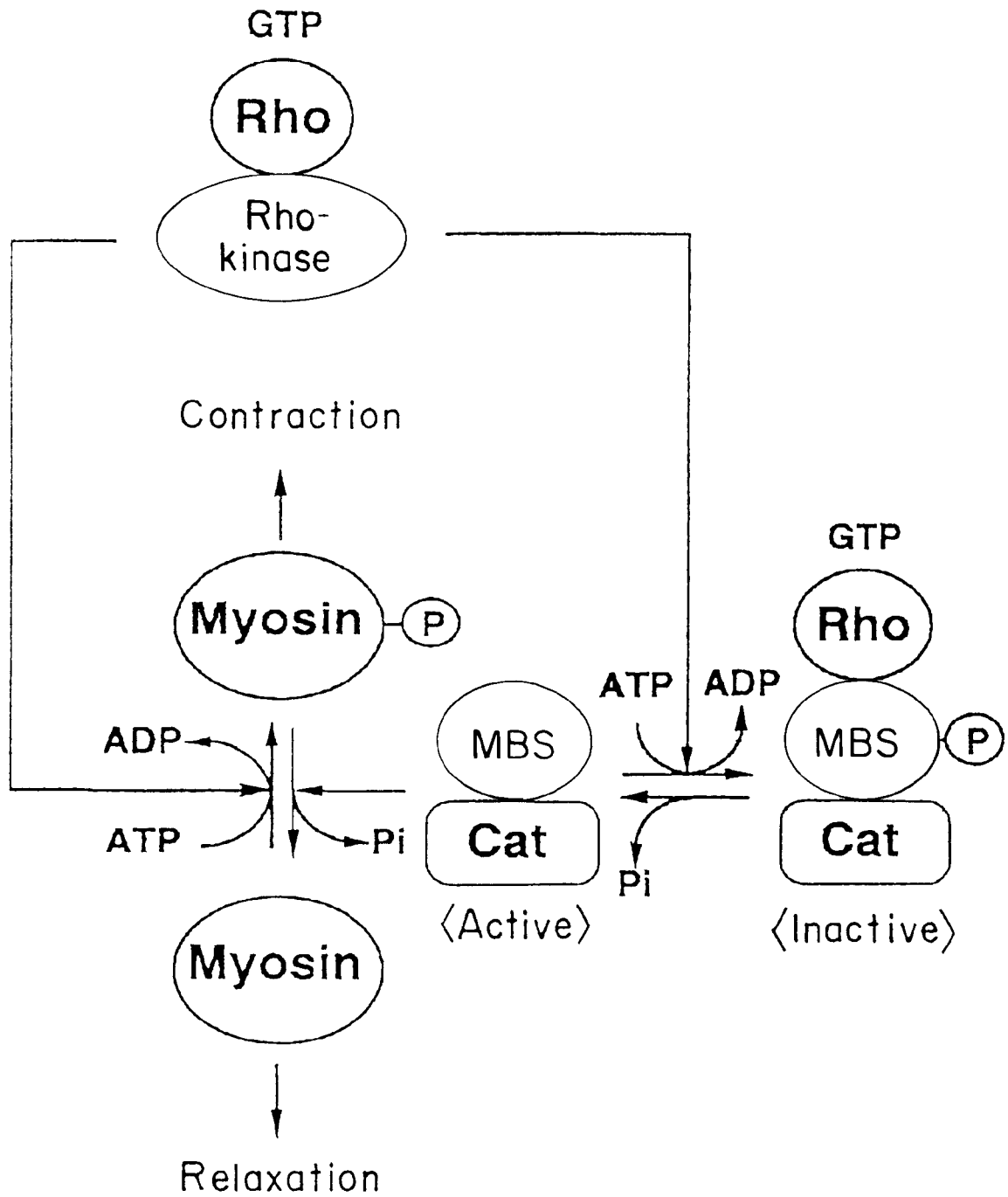
F I G. 22

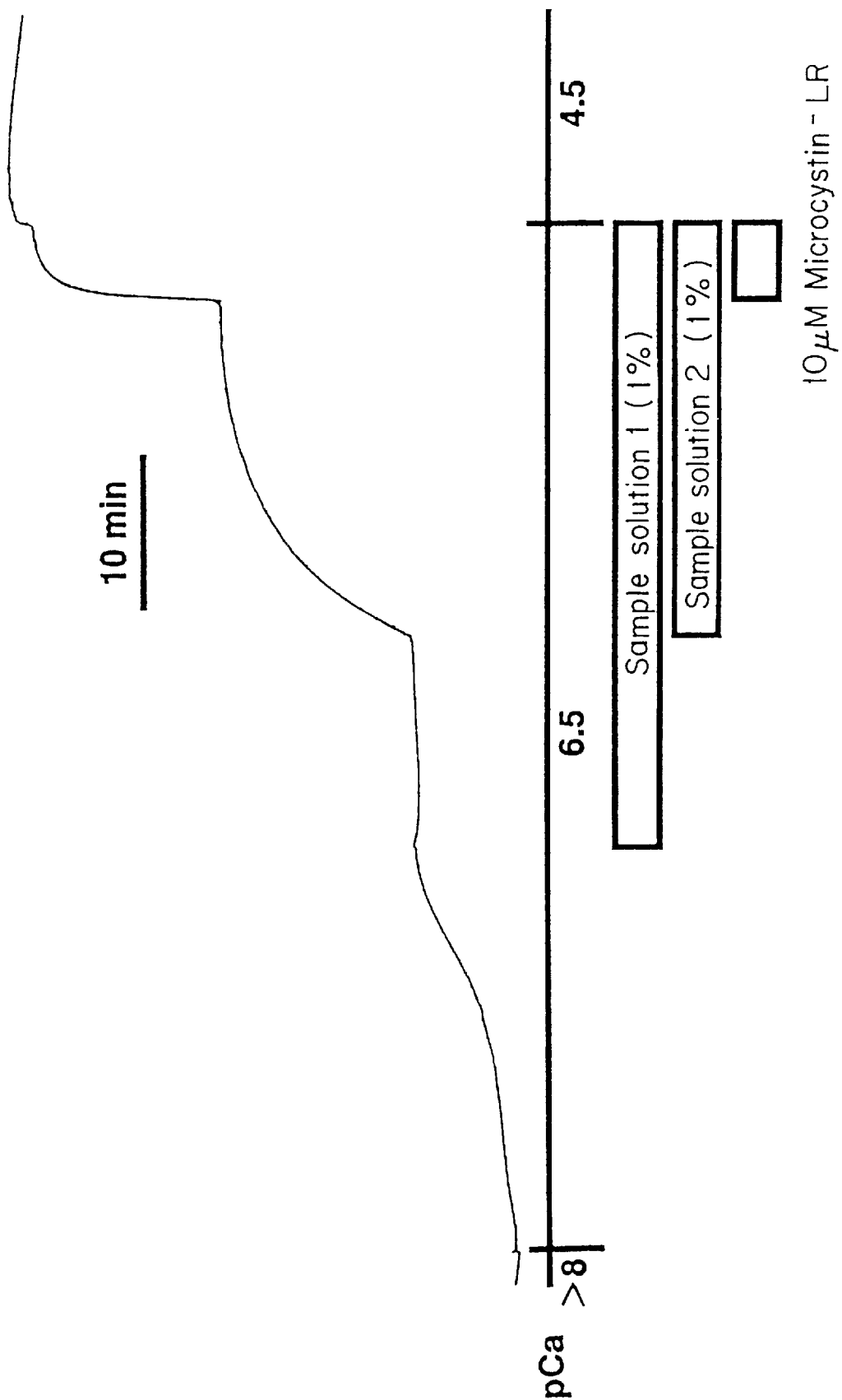
F I G. 24

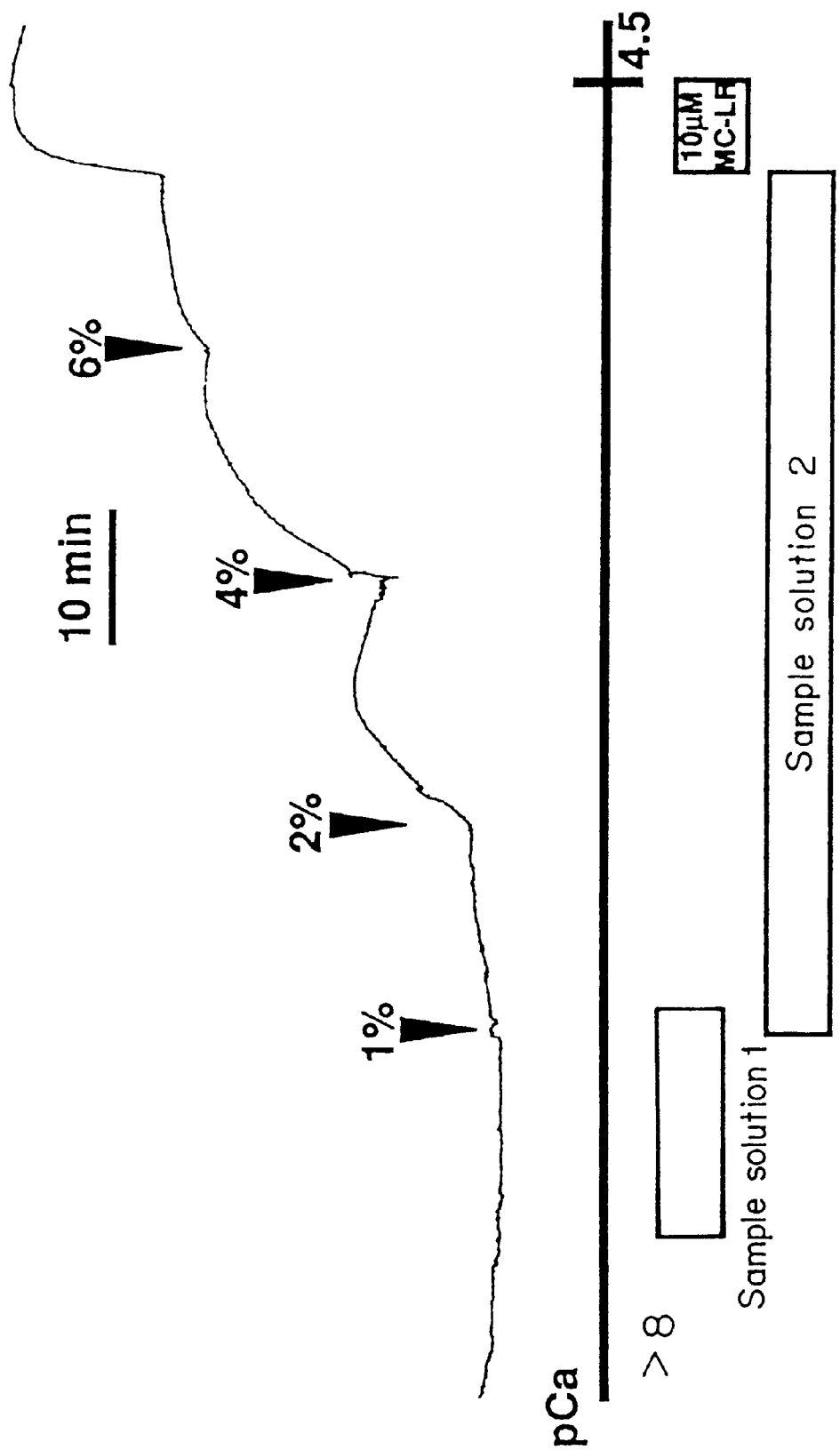
F I G. 25

RHO TARGET PROTEIN RHO-KINASE

FIELD OF THE INVENTION

This invention relates to a novel protein having activated Rho-binding activity.

BACKGROUND OF THE INVENTION

A group of low-molecular-weight GTP-binding proteins (G-proteins) with molecular weights of 20,000–30,000 with no subunit structures is observed in organisms. To date, over fifty or more members have been found as the super family of the low-molecular-weight G-proteins in a variety of organisms, from yeast to mammals. The low-molecular-weight G-proteins are divided into four families of Ras, Rho, Rab and the others based on homologies of amino acid sequences. It has been revealed that the small G-proteins control a variety of cellular functions. For example, the Ras protein is considered to control cell proliferation and differentiation, and the Rho protein is considered to control cell morphological change, adhesion and motility.

The Rho protein, having GDP/GTP-binding activity and intrinsic GTPase activity, is believed to be involved in cytoskeletal responses to extracellular signals such as lysophosphatidic acid (LPA) and certain growth factors. When the inactive GDP bound form of Rho is stimulated, it is transformed to the active GTP bound form of Rho protein (hereinafter referred to as "the activated Rho protein") by GDP/GTP exchange proteins such as Smg GDS, Dbl or Ost. The activated Rho protein then acts on target proteins to form stress fibers and focal contacts, thus inducing the cell adhesion and motility (Experimental Medicine, Vol. 12, No. 8, 97–102 (1994); Takai, Y. et al., Trends Biochem. Sci., 20, 227–231 (1995)). On the other hand, the intrinsic GTPase activity of the Rho protein transforms the activated Rho protein to the GDP bound form of Rho protein. This intrinsic GTPase activity is enhanced by what is called GTPase-activating proteins (GAP) (Lamarche, N. & Hall, A. et al., TIG, 10, 436–440 (1994)).

Natural RhoA proteins bear Cys-A-A-Leu (SEQ ID NO: 6) (A: aliphatic amino acid) on the C-terminal thereof. The Cys residue is geranylgeranylated by geranylgeranyl transferase and its carboxyl group methylated in posttranslational processing, which is considered essential for the binding of the Rho protein to cell membranes and interaction with activity regulating proteins as well as for the expression of the functions thereof (Imazumi, K. et al., Experimental Medicine, Vol. 13, 646–656 (1995)).

The Rho family proteins, including RhoA, RhoB, RhoC, Rac1, Rac2 and Cdc42, share more than 50% sequence identity with each other. The Rho family proteins are believed to be involved in inducing the formation of stress fibers and focal contacts in response to extracellular signals such as lysophosphatidic acid (LPA) and growth factors (A. J. Ridley & A. Hall, Cell, 70, 389–399 (1992); A. J. Ridley & A. Hall, EMBO J., 1353, 2600–2610 (1994)). The subfamily Rho is also considered to be implicated in physiological functions associated with cytoskeletal rearrangements, such as cell morphological change (H. F. Parterson et al., J. Cell Biol., 111, 1001–1007 (1990)), cell adhesion (Morii, N. et al., J. Biol. Chem., 267, 20921–20926 (1992); T. Tominaga et al., J. Cell Biol., 120, 1529–1537 (1993); Nusrat, A. et al., Proc. Natl. Acad. Sci. USA, 92, 10629–10633 (1995)*; Landanna, C. et al., Science, 271, 981–983 (1996)*, cell motility (K. Takaishi et al., Oncogene, 9, 273–279 (1994), and cytokinesis (K. Kishi et al., J. Cell Biol., 120, 1187–1195 (1993); I. Mabuchi et al., Zygote, 1, 325–331 (1993)). (An asterisk hereinafter indicates a publication issued after the first filed application which provides the right of the priority of the present application.) In addition, it has been suggested that the Rho is involved in the regulation of smooth muscle contraction (K. Hirata et al., J. Biol. Chem., 267, 8719–8722 (1992); M. Noda et al., FEBS Lett., 367, 246–250 (1995); M. Gong et al., Proc. Natl. Acad. Sci. USA, 93, 1340–1345 (1996)*), and the expression of phosphatidylinositol 3-kinase (PI3 kinase) (J. Zhang et al., J. Biol. Chem., 268, 22251–22254 (1993)), phosphatidylinositol 4-phosphate 5-kinase (PI 4,5-kinase) (L. D. Chong et al., Cell, 79, 507–513 (1994)) and c-fos (C. S. Hill et al., Cell, 81, 1159–1170 (1995)).

Recently, it has also be found that Ras-dependent tumorigenesis is suppressed when the Rho protein of which the amino acid sequence has been partly substituted is introduced to cells, revealing that the Rho protein plays an important role in Ras-induced transformation, that is, tumorigenesis (G. C. Prendergast et al., Oncogene, 10, 2289–2296 (1995); Khosravi-Far, R. et al., Mol. Cell. Biol., 15, 6443–6453 (1995)*; R. Qiu et al., Proc. Natl. Acad. Sci. USA, 92, 11781–11785 (1995)*; Lebowitz, P. et al., Mol. Cell, Biol., 15, 6613–6622 (1995)*).

It has also been proved that the Rho protein enhances not only cell proliferation, cell motility and cell aggregation but also smooth muscle contraction. Recent studies have demonstrated that the Rho protein is involved in the smooth muscle contraction (K. Hirata et al., J. Biol. Chem., 267, 8719–8722 (1992); Noda, M. et al., FEBS Lett., 367, 246–250 (1995)). Therefore, it can reasonably be assumed that the activated Rho-binding protein is also involved in the smooth muscle contraction.

The phosphorylation of myosin light chain plays vital roles in the smooth muscle contraction (Kamm, K. E. & Stull, J. T., Annu. Rev. Pharmacol. Toxicol., 25, 593–603 (1985); Hartshorne, D. J. & Johnson, D. R. (1987) in Physiology of the Gastrointestinal Tract, (Johnson, L. R., ed), pp. 423–482, Raven Press, New York; Sellers, J. R. & Adelstein, R. S. in The Enzyme (Boyer, P. and Erevs, E. G., eds), Vol. 18, pp. 381–418, Academic Press, San Diego, Calif. (1987)) and the actin-myosin interaction for stress fiber formation in non-muscle cells (Huttenlocher, A. et al., Curr. Opi. Cell Biol., 7, 697–706 (1995)) and, thus, involved in cytokinesis and cell motility (Huttenlocher, A. et al., Curr. Opi. Cell Biol., 7, 697–706 (1995)).

Myosin light chain kinase phosphorylates primarily the Ser-19 of myosin light chain (Kamm, K. E. & Stull, J. T., Annu. Rev. Pharmacol. Toxicol., 25, 593–603 (1985); Hartshorne, D. J. & Johnson, D. R., (1987) in Physiology of the Gastrointestinal Tract, (Johnson, L. R., ed), pp. 423–482, Raven Press, New York; Sellers, J. R. & Adelstein, R. S. in The Enzyme (Boyer, P. and Erevs, E. G., eds), Vol. 18, pp. 381–418, Academic Press, San Diego, Calif. (1987); Ikebe, M. & Hartshorne, D. J., J. Biol. Chem., 260, 10027–10031 (1985)). No protein kinase obtained thus far other than specific kinases such as myosin light chain kinase phosphorylates this site (Tan, J. L. et al., Annu. Rev. Biochem., 61, 721–759 (1992).

When a smooth muscle is stimulated by an agonist such as an angiotonic, $Ca^{2+}$ moves into cytoplasm, and activates the calmodulin-dependent myosin light chain kinase. The phosphorylated myosin light chain induces myosin-actin interaction, which in turn activates myosin ATPase (Kamm, K. E. & Stull, J. T., Annu. Rev. Pharmacol. Toxicol., 25, 593–603 (1985); Hartshorne, D. J. & Johnson, D. R., (1987) in Physiology of the Gastrointestinal Tract, (Johnson, L. R., ed), pp. 423–482, Raven Press, New York; Sellers, J. R. & Adelstein, R. S. in The Enzyme (Boyer, P. and Erevs, E. G., eds), Vol. 18, pp. 381–418, Academic Press, San Diego, Calif. (1987)), thus inducing the smooth muscle contraction (Kamm, K. E. & Stull, J. T., Annu. Rev. Pharmacol. Toxicol., 25, 593–603 (1985); Hartshorne, D. J. & Johnson, D. R., (1987) in Physiology of the Gastrointestinal Tract, (Johnson, L. R., ed), pp. 423–482, Raven Press, New York; Sellers, J. R. & Adelstein, R. S. in The Enzyme (Boyer, P. and Erevs, E. G., eds), Vol. 18, pp. 381–418, Academic Press, San Diego, Calif. (1987)). However, $Ca^{2+}$ level in the cytosol is not necessarily proportional to the contraction level, indicating another explanation for the mechanism of the regulation of $Ca^{2+}$ sensitivity in smooth muscle contraction (Bradley, A. B. & Morgan, K. G., J. Physiol., 385, 437–448 (1987)). As GTPγS (non-hydrolyzable GTP analog) decreases the $Ca^{2+}$ concentration necessary for the contraction of permeabilized (skinned) smooth muscles, GTP-binding proteins were expected to regulate $Ca^{2+}$ sensitivity (Kitazawa, T. et al., Proc. Natl. Acad. Sci. U.S.A., 88, 9307–9310 (1991); Moreland, S. et al., Am. J. Physiol., 263, 540–544 (1992)). The Rho protein was proved to be involved in $Ca^{2+}$ sensitivity of smooth muscles, which is enhanced by GTP (Hirata, K. et al., J. Biol. Chem., 267, 8719–8722 (1992)). Recently, in permeabilized smooth muscles, it was demonstrated that GTPγS enhances the phosphorylation of myosin light chain at submaximal $Ca^{2+}$ concentration, suggesting that the enhancement was attributed to the activation of the Rho protein and the inhibition of the enzymatic activity of myosin light chain phosphatase, which dephosphorylates myosin light chain (Noda, M. et al., FEBS Lett., 367, 246–250 (1995)). However, it has not been resolved yet how the Rho protein inhibits myosin light chain phosphatase, whether the enhancement of the phosphorylation of myosin light chain by the Rho protein is attributed solely to the inhibition of myosin light chain phosphatase activity, and, thus, how the Rho protein regulates the $Ca^{2+}$ sensitivity of smooth muscles and enhances the smooth muscle contraction.

These findings indicate that the Rho protein controls a variety of signal transduction pathways for cell morphological change, cell adhesion, cell motility, cytokinesis, tumorigenesis, metastasis, vascular smooth muscle contraction, etc. The Rho protein appears to be able to act on a number of target molecules to control all these signal transduction pathways.

It is only recently (after the first filed application which provides the right of the priority of the present application) that a several proteins have been reported as candidates of Rho-targets in mammals: protein kinase N (PKN) (Watanabe, G. et al., Science, 271, 645–648 (1996)*; Amano, M. et al., Science, 271, 648–650 (1996)*), rhophilin (Watanabe, G. et al., Science, 271, 645–648 (1996)*, citron (Madaule, P. et al., FEBS Lett., 377, 243–248 (1995)*), ROKα (Leung, T. et al., J. Biol. Chem., 270, 29051–29054 (1995)*), p160$^{ROCK}$ (Ishizaki, T. et al., EMBO J., 15, 1885–1893 (1996)*) and rhotekin (Reid, T. et al., J. Biol. Chem., 271, 13556–13560 (1996)*). All these proteins bind to GTP-binding RhoA protein, except that citron binds also to GTP-binding Rac1.

Among these proteins, PKN has an enzymatic region which closely resembles the protein kinase region of protein kinase C and exhibits serine/threonine kinase activity (Mukai, H. & Ono, Y., Biochem. Biopys. Res. Commun., 199, 897–904 (1994); Mukai, H. et al., Biochem. Biopys. Res. Commun., 204, 348–356 (1994)). On the other hand, ROKα (Leung, T. et al. (1995), ibid.) and p160$^{ROCK}$ (Ishizaki, T. et al. (1996)*, ibid.) also have amino acid sequences resembling a serine/threonine kinase region (Leung, T. et al. (1995)*, ibid.).

In addition to those reported in mammals, protein kinase C1 (PKC1) in yeast (*Saccharomyces cerevisiae*) has recently been identified as a target protein of the Rho1 protein, corresponding to RhoA in mammals (Nonaka, H. et al., EMBO J., 14, 5931–5938 (1995)*). Only recently, 1,3-β-glucan synthase has been identified as a target protein of the Rho1p protein in yeast (*Saccharomyces cerevisiae*) (Drgonova, J. et al., Science, 272, 277–279 (1996)*; Qadota, H. et al., Science, 272, 279–281 (1996)*).

However, mechanisms of intercellular signal transduction involving the activated Rho protein, particularly those of tumorigenesis and smooth muscle contraction, are still unknown.

An asterisk hereinafter indicates a publication issued after the first filed application which provides the right of the priority of the present application.

SUMMARY OF THE INVENTION

The inventors isolated a protein having activated Rho-binding activity and protein kinase activity from gray matter of bovine brain. The molecular weight of the protein was about 164 kDa as measured by SDS-PAGE. Also, the inventors have found that this protein (Rho-kinase) bound to the effector domain of the activated Rho protein, that the Rho-kinase showed kinase activity, that the kinase activity was enhanced by the GTPγS-Rho protein, and that the Rho-kinase had a coiled-coil domain in the internal region. In other words, the Rho-kinase proved to be a target, serine/threonine kinase, for the Rho protein and a mediator of the Rho protein dependent signal transduction pathway. The inventors also found that the Rho-kinase phosphorylates myosin-binding subunit of myosin light chain phosphatase and myosin and induces vascular smooth muscle contraction.

Also, the inventors successfully cloned the cDNA of human Rho-kinase. The present invention is based on these findings.

An object of the present invention is thus to provide a protein having activated Rho-binding activity and protein kinase activity (hereinafter referred to as "Rho-kinase").

Another object of the present invention is to provide a partial protein of said protein, the base sequence encoding said protein including the partial protein, a vector containing said base sequence, a host cell transformed by said vector, a process for preparing said proteins, a tumorigenesis or metastasis suppressing agent comprising said protein, a method for screening a material inhibiting the binding between the activated Rho protein and said proteins, a method for screening materials inhibiting the protein kinase activity of said proteins, a partial amino acid sequence of Rho-kinase, an antibody specifically reacting with said amino acid sequences, and a method and kit for detection using said antibody.

BRIEF DESCRIPTION OF THE DRAWINGS

FIG. 4 is an electrophoretic photograph showing autophosphorylation of bovine Rho-kinase. Rho-kinase was autophosphorylated in the presence of the following proteins (1 μM each): Lane 1: GST, Lane 2: GDP•GST-RhoA, Lane 3: GTPγS•GST-RhoA, Lane 4: GTPγS•GST-RhoA$^{Ala37}$. An arrow indicates the position of Rho-kinase on SDS-PAGE. The results shown are representative of three independent experiments.

FIG. 6 shows enhancement of the phosphorylation of S6 peptide (40 μM) by bovine Rho-kinase in the presence of GTPγS•GST-RhoA (1 μM).

FIG. 8 shows phosphorylation of S6 peptide by bovine Rho-kinase. Closed square: GTPγS-RhoA (posttranslationally processed type), Open square: GDP-RhoA (posttranslationally processed type) Closed circle: GTPγS•GST-RhoA (posttranslationally unprocessed type), Open circle: GDP•GST-RhoA (posttranslationally unprocessed type).

FIG. 9 shows the deduced amino acid sequence of bovine Rho-kinase SEQ ID NO: 1. Amino acid sequences determined by partial peptide sequencing of Rho-kinase purified from bovine brain gray matter are indicated by single underlines. The amino acid sequence of the probe used for Rho-kinase cDNA cloning is indicated by double underlines.

FIG. 12 is an electrophoretic photograph showing binding between the activated Rho and a protein corresponding to the coiled-coil domain of bovine Rho-kinase prepared by in vitro translation. Lane 1: GST, Lane 2: GDP•GST-RhoA, Lane 3: GTPγS•GST-RhoA, Lane 4: GTPγS•GST-RhoA$^{Ala37}$, Lane 5: GDP•GST-Rac1, Lane 6: GTPγS•GST-Rac1, Lane 7: GDP•GST-H-Ras, Lane 8: GTPγS•GST-H-Ras.

FIG. 14 shows thiophosphorylation of chicken myosin-binding subunit and inhibition of myosin light chain phosphatase activity, as a function of bovine Rho-kinase concentration. Myosin-binding subunit was $^{35}$S-thiophosphorylated with (closed circle) or without (open circle) GTPγS•GST-RhoA. Myosin light chain phosphatase activity was measured with (closed square) or without (open square) GTPγS•GST-RhoA, using Rho-kinase that were phosphorylated in the presence of ATPγS. Myosin light chain phosphatase activity was also measured in the absence of ATPγS; i.e., using non-phosphorylated Rho-kinase (diamond shape).

FIG. 16 shows degree of myosin light chain phosphorylation in NIH/3T3 cell lines overexpressing RhoA or RhoA$^{Val14}$.

FIG. 22 shows the model for regulation of myosin light chain by Rho protein, Rho-kinase, and myosin light chain phosphatase.
Cat: catalytic subunit of myosin light chain phosphatase.
MBS: myosin-binding subunit.

FIG. 24 shows permeabilized smooth muscle contraction by GST-Rho-kinase at pCa 6.5 (Ca$^{2+}$ concentration of 10$^{-6.5}$ M) as a function of time.

FIG. 25 shows dose-dependent contraction of a permeabilized smooth muscle by GST-Rho-kinase at pCa 8 (Ca$^{2+}$ concentration of 10$^{-8}$ M) or above.

DETAILED DESCRIPTION OF THE INVENTION

Definitions

Figure 1:
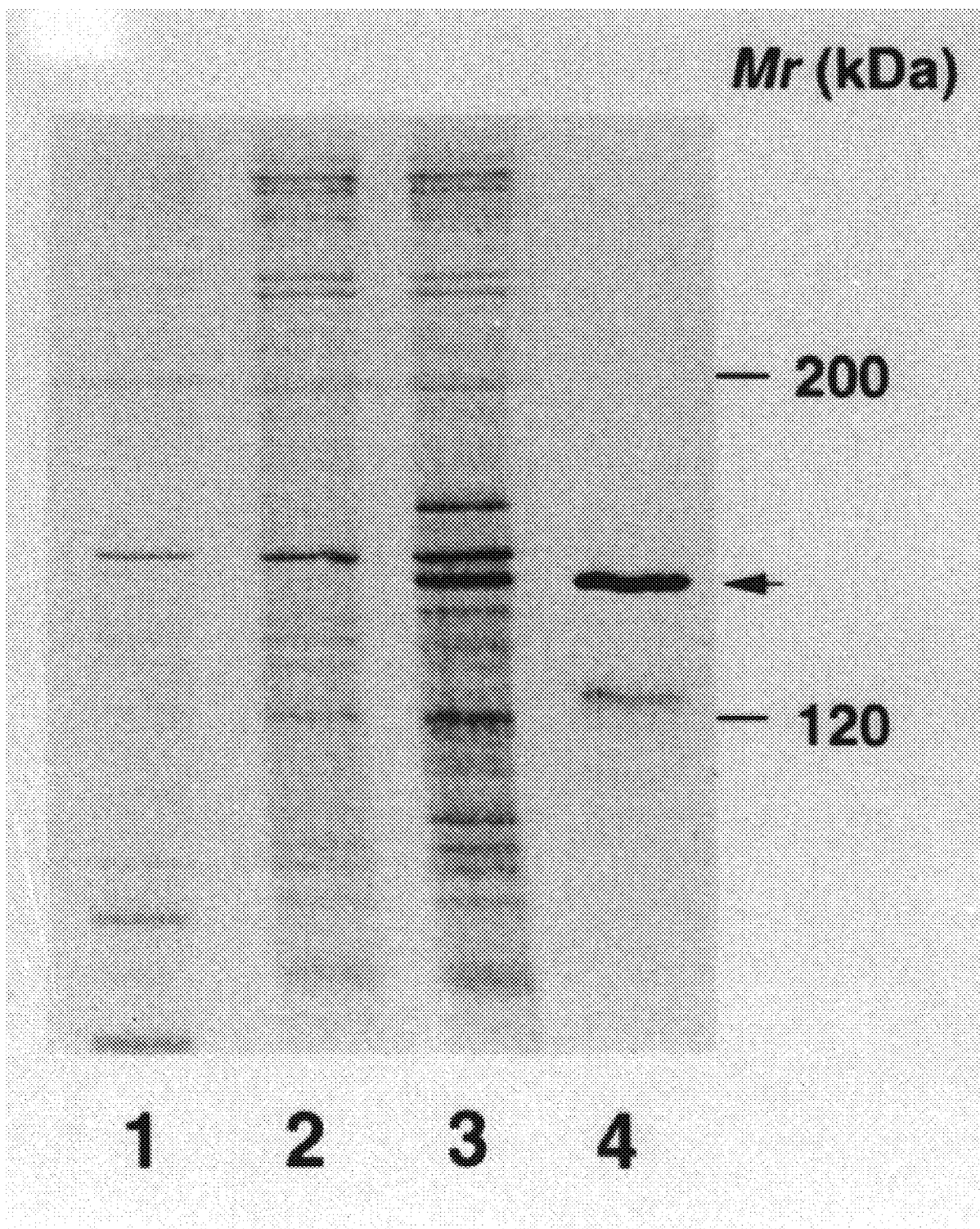
FIG. 1 is an electrophoretic photograph showing a result of the purification of a protein which specifically binds to the activated Rho protein. The crude membrane fraction was loaded onto a glutathione-Sepharose column containing either GST (lane 1), GDP•GST-RhoA (lane 2), or GTPγS•GST-RhoA (lane 3). To enrich bovine Rho-kinase, the crude membrane fraction was loaded onto a glutathione- Sepharose column containing GTPγS•GST-RhoA, and bovine Rho-kinase was eluted by addition of 1% CHAPS (lane 4).

The term "amino acid" herein refers to the meaning including either of optical isomers, i.e., an L-isomer and a D-isomer. Thus, the term "peptide" herein refers to the meaning including not only peptides constituted by L-amino acids solely but also peptides comprising D-amino acids partially or totally.

Furthermore, the term "amino acid" herein refers to the meaning including not only twenty α-amino acids which constitute natural proteins but also other α-amino acids as well as β-, γ- and δ-amino acids, non-natural amino acids, and the like. Thus, amino acids with which peptides are substituted or amino acids inserted into peptides as shown below are not restricted to twenty α-amino acids which constitute natural proteins but may be other α-amino acids as well as β-, γ- and δ-amino acids, non-natural amino acids, and the like. Such β-, γ- and δ-amino acids include β-alanine, γ-aminobutyric acid or ornithine. In addition, the amino acids other than those constituting natural proteins or the non-natural amino acids include 3,4-dihydroxyphenylalanine, phenylglycine, cyclohexylglycine, 1,2,3,4-tetrahydroisoquinolin-3-carboxylic acid or nipecotinic acid.

The term "protein according to the present invention" refers to the meaning including derivatives of the proteins.

The term "base sequence" herein refers to RNA sequences as well as DNA sequences.

Protein

The protein according to the present invention is a protein having activated Rho protein binding activity and protein kinase activity (Rho-kinase) or derivatives thereof. Such Rho family proteins include RhoA, RhoB, RhoC and RhoG proteins.

In the present invention, the term "protein having activated Rho protein binding activity" means a protein which is evaluated by one skilled in the art to bind to the activated Rho protein, e.g., proteins which are evaluated to bind to the activated Rho protein when examined under the same condition as in example 1, 4 or 11.

In this specification, the Rho protein includes Rho protein which has been modified in such a manner that the binding between the Rho protein and the protein according to the present invention is not essentially damaged. Such modified proteins include an RhoA mutant (RhoA$^{Val14}$), in which the amino acid 14 is substituted by valine.

In the present invention, the term "protein having protein kinase activity" means a protein which is evaluated by one skilled in the art to have protein kinase activity, e.g., proteins which are evaluated to have protein kinase activity when examined under the same condition as in any one of examples 2, 5, 6–9.

The protein according to the present invention is characterized by the enhancement of the protein kinase activity as it binds to the activated Rho protein. The term "protein kinase activity" refer to the meaning including serine/threonine kinase activity.

The protein according to the present invention is not specifically restricted to any sources but it may be derived from mammals including bovine and humans, or any other sources.

The molecular weight of Rho-kinase from bovine is about 164 kDa as measured by SDS-PAGE.

Examples of the protein according to the present invention include proteins from bovine having the activated Rho protein binding activity and protein kinase activity with a molecular weight of about 164 kDa as measured by SDS-PAGE (hereinafter referred to as "bovine Rho-kinase").

Examples of the protein according to the present invention also include proteins from humans having the activated Rho protein binding activity and protein kinase activity (hereinafter referred to as "human Rho-kinase").

The protein according to the present invention can be obtained, for example, from bovine brain gray matter according the method described in example 1.

The term "derivatives of proteins" herein includes proteins in which an amino group at an amino terminal (N-terminal) or all or a part of amino groups of side chains of amino acids, and/or a carboxyl group at a carboxyl terminal (C-terminal) or all or a part of carboxyl groups of side chains of amino acids, and/or functional groups other than the amino groups and carboxyl groups of the side chains of the amino acids such as hydrogen, a thiol group or an amido group have been modified by appropriate other substituents. The modification by the appropriate other substituents is carried out in order to, for example, protect functional groups in the protein, improve safety and tissue-translocation of the protein or enhance the protein activity.

The derivatives of the proteins include:
(1) proteins in which one or more hydrogen atoms of the amino group at the amino terminal (N-terminal) or a part or all of the amino groups of the side chains of the amino acids are replaced by substituted or unsubstituted alkyl groups (which may be straight chain or branched chain or cyclic chain) such as a methyl group, an ethyl group, a propyl group, an isopropyl group, an isobutyl group, a butyl group, a t-butyl group, a cyclopropyl group, a cyclohexyl group or a benzyl group, substituted or unsubstituted acyl groups such as a formyl group, an acetyl group, a caproyl group, a cyclohexylcarbonyl group, a benzoyl group, a phthaloyl group, a tosyl group, a nicotinoyl group or a piperidincarbonyl group, urethane-type protective groups such as a p-nitrobenzyloxycarbonyl group, a p-methoxybenzyloxycarbonyl group, a p-biphenylisopropyl-oxycarbonyl group or a t-butoxycarbonyl group, or urea-type substituents such as a methylaminocarbonyl group, a phenylcarbonyl group or a cyclohexylaminocarbonyl group;

(2) proteins in which the carboxyl groups at the carboxyl terminal (C-terminal) or a part or all of the side chains of the amino acids are esterified (for example, the hydrogen atom(s) are replaced by methyl, ethyl, isopropyl, cyclohexyl, phenyl, benzyl, t-butyl or 4-picolyl), or amidated (for example, unsubstituted amides or C1–C6 alkylamide such as an methylamide, an ethylamide or an isopropylamide are formed; or (3) proteins in which a part or all of the functional groups other than the amino groups and the carboxyl groups of the side chains of the amino acids such as hydrogen, a thiol group or an amino group are replaced by the substituents described in (1) or a trityl group.

Examples of the protein according to the present invention include protein consisting of the amino acid sequence of SEQ ID NO.1 and derivatives thereof. The "bovine Rho-kinase" includes this protein. Examples of the amino acid sequence of SEQ ID No.1 can be obtained, for example, from the cDNA sequence derived from a bovine brain cDNA library using the oligonucleotide corresponding to the peptide indicated by double underlines in FIG. 9 as a probe (see example 3).

Examples of the protein according to the present invention also include the protein consisting of the amino acid sequence of SEQ ID NO.4 and derivatives thereof. The "human Rho-kinase" includes this protein.

Other examples of the protein according to the present invention include proteins consisting of the amino acid sequence of SEQ ID NO.1 and having the activated Rho protein binding activity and protein kinase activity, wherein one or more amino acid sequences are added and/or inserted in the amino acid sequence of SEQ ID NO.1, and/or one or more amino acids in the amino acid sequence of SEQ ID NO.1 are substituted and/or deleted. The terms "addition", "insertion", "substitution" and "deletion" refer to those that do not damage the activated Rho protein binding activity and protein kinase activity of the protein consisting of the amino acid sequence of SEQ ID NO.1.

Examples of such deletions include deletions of all or part of the regions of the amino acid sequence of SEQ ID NO.1 except the amino acid sequence 90–359 (protein kinase domain) and amino acid sequence 943–1068 (Rho protein binding domain); more specifically, deletions of the amino acid sequences 1–89, 360–942 and/or 1069–1388, or a part thereof.

According to another aspect of the present invention, we provide a protein having the amino acid sequence 90–359 (protein kinase domain) and amino acid sequence 943–1068 (Rho protein binding domain) in SEQ ID NO.1.

Other examples of the protein according to the present invention include proteins consisting of the amino acid sequence of SEQ ID NO.4 and having the activated Rho protein binding activity and protein kinase activity, wherein one or more amino acid sequences are added and/or inserted in the amino acid sequence of SEQ ID NO.4, and/or one or more amino acids in the amino acid sequence of SEQ ID NO.4 are substituted and/or deleted. The terms "addition", "insertion", "substitution" and "deletion" refer to the same meanings as above.

Examples of such deletions include deletions of all or part of the regions of the amino acid sequence of SEQ ID NO.4 except the amino acid sequence 90–359 (protein kinase domain) and the amino acid sequence 943–1068 (Rho protein binding domain); more specifically, deletions of the amino acid sequences 1–89, 360–942 and/or 1069–1388, or a part thereof.

According to another aspect of the present invention, we provide a protein having the amino acid sequence 90–359 (protein kinase domain) and amino acid sequence 943–1068 (Rho protein binding domain) in SEQ ID NO.4.

Rho-kinase is expressed primarily in cerebrum and cerebellum (see example 3 (4)). Rho-kinase crossreacts with the antibody described after (see example 3 (4) and example 10).

The term "expressed primarily in cerebrum and cerebellum" refer to the meaning that expression in cerebrum and cerebellum is evaluated by one skilled in the art to be more prominent than in other organs, for example, that expression in cerebrum and cerebellum is evaluated to be more prominent than in other organs when examined under the same condition as in example 3 (4).

The present invention provides a protein having the activated Rho protein binding activity and not having protein kinase activity or derivatives thereof.

Examples of such proteins include proteins consisting of the amino acid sequence of SEQ ID NO.1 and having the activated Rho protein binding activity and not having the protein kinase activity, wherein one or more amino acid sequences are added and/or inserted in the amino acid sequence of SEQ ID NO.1, and/or one or more amino acids in the amino acid sequence of SEQ ID NO. 1 are substituted and/or deleted. The terms "addition", "insertion", "substitution" and "deletion" refer to those that do not damage the activated Rho protein binding activity and damage the protein kinase activity of the protein consisting of the amino acid sequence of SEQ ID NO.1.

Examples of such deletions include deletions of the amino acid sequence 90–359 (protein kinase domain) in SEQ ID NO.1 or a region containing a part thereof having protein kinase activity.

Also, a protein consisting of the amino acid sequence of SEQ ID NO.1 (containing an addition, insertion, substitution and/or deletion) having the activated Rho protein binding activity and not having the protein kinase activity or derivatives thereof may contain, in addition to the above addition, insertion, substitution and/or deletion, other additions, insertions, substitutions and/or deletions that do not damage the Rho protein binding activity thereof.

Examples of such deletions include deletions of all or part of the regions of the amino acid sequence of SEQ ID NO.1 except the amino acid sequence 943–1068 (Rho protein binding domain) (see example 11); more specifically, deletions of the amino acid sequence 1–89 or a part thereof, the amino acid sequence 360–942 or a part thereof, or the amino acid sequence 1069–1388 or a part thereof.

Examples of the aforementioned proteins include proteins consisting of the amino acid sequence of SEQ ID NO.4 and having the activated Rho protein binding activity and not having the protein kinase activity, wherein one or more amino acid sequences are added and/or inserted in the amino acid sequence of SEQ ID NO.4, and/or one or more amino acids in the amino acid sequence of SEQ ID NO.4 are substituted and/or deleted. The terms "addition", "insertion", "substitution" and "deletion" refer to those that do not damage the activated Rho protein binding activity and damage the protein kinase activity of the protein consisting of the amino acid sequence of SEQ ID NO.4.

Examples of such deletions include deletions of the amino acid sequence 90–359 (protein kinase domain) of SEQ ID NO.4 or a region containing a part thereof having protein kinase activity.

Also, a protein consisting of the amino acid sequence of SEQ ID NO.4 (containing an addition, insertion, substitution and/or deletion) having the activated Rho protein binding activity and not having the protein kinase activity or derivatives thereof may contain, in addition to the above addition, insertion, substitution and/or deletion, other additions, insertions, substitutions and/or deletions that do not damage the Rho protein binding activity thereof.

Examples of such deletions include deletions of all or part of the regions of the amino acid sequence of SEQ ID NO.4 except the amino acid sequence 943–1068 (Rho protein binding domain) (see example 11); more specifically, deletions of the amino acid sequence 1–89 or a part thereof, the amino acid sequence 360–942 or a part thereof, or the amino acid sequence 1069–1388 or a part thereof.

According to another aspect of the present invention, we provide a protein comprising the amino acid sequence 943–1068 in SEQ ID NO.4 or derivatives thereof. This protein has the activated Rho protein binding activity and does not have the protein kinase activity.

According to the present invention, we also provide a protein having the protein kinase activity and not having the activated Rho protein binding activity or derivatives thereof. The term "protein kinase activity" refer to the meaning including serine/threonine kinase activity.

Examples of such proteins include proteins consisting of the amino acid sequence of SEQ ID NO.1 having the protein kinase activity and not having the activated Rho protein binding activity, wherein one or more amino acid sequences are added and/or inserted in the amino acid sequence of SEQ ID NO.1, and/or one or more amino acids in the amino acid sequence of SEQ ID NO.1 are substituted and/or deleted. The terms "addition", "insertion", "substitution" and "deletion" refer to those that do not damage the protein kinase activity and damage the activated Rho protein binding activity of the protein consisting of the amino acid sequence of SEQ ID NO.1.

Examples of such deletions include deletions of the amino acid sequence 943–1068 in SEQ ID NO.1 or a region containing a part thereof having the activated Rho protein binding activity.

Also, a protein consisting of the amino acid sequence in SEQ ID NO.1 (containing an addition, insertion, substitution and/or deletion) having protein kinase activity and not having activated Rho protein binding activity or derivatives thereof may contain, in addition to the above addition, insertion, substitution and/or deletion, other additions, insertions, substitutions and/or deletions that do not damage the protein kinase activity thereof.

Examples of such deletions include deletions of all or part of the regions of the amino acid sequence of SEQ ID NO.1 except the amino acid sequence 90–359 (protein kinase domain); more specifically, the deletion of the amino acid sequence 1–89 or a part thereof, or the amino acid sequence 360–1388 or a part thereof.

According to another aspect of the present invention, we provide a protein comprising the amino acid sequence 90–359 of SEQ ID NO.1 or derivatives thereof. Examples of such derivatives include a protein comprising the amino acid sequence 6–553 in SEQ ID NO.1 (see example 7). This protein has the protein kinase activity and does not have the activated Rho protein binding activity.

Examples of the aforementioned proteins include proteins consisting of the amino acid sequence of SEQ ID NO.4 having the protein kinase activity and not having the activated Rho protein binding activity, wherein one or more amino acid sequences are added and/or inserted in the amino acid sequence of SEQ ID NO. 4, and/or one or more amino acids in the amino acid sequence of SEQ ID NO.4 are substituted and/or deleted. The terms "addition", "insertion", "substitution" and "deletion" refer to those that do not damage the protein kinase activity and damage the activated Rho protein binding activity of the protein consisting of the amino acid sequence of SEQ ID NO.4.

Examples of such deletions include deletions of the amino acid sequence 943–1068 of SEQ ID NO.4 or a region containing any part thereof having the activated Rho protein binding activity.

Also, a protein consisting of the amino acid sequence of SEQ ID NO.4 (containing an addition, insertion, substitution and/or deletion) having protein kinase activity and not having activated Rho protein binding activity or derivatives thereof may contain, in addition to the above addition, insertion, substitution and/or deletion, other additions, insertions, substitutions and/or deletions that do not damage the protein kinase activity thereof.

Examples of such deletions include deletions of all or part of the regions of the amino acid sequence of SEQ ID NO.4 except the amino acid sequence 90–359 (protein kinase domain); more specifically, deletions of the amino acid sequence 1–89 or a part thereof, or the amino acid sequence 360–1388 or a part thereof.

According to another aspect of the present invention, we provide a protein comprising the amino acid sequence 90–359 or amino acid sequence 6–553 (corresponding to the amino acid sequence 6–553 in SEQ ID NO.1 ) in SEQ ID NO.4 or derivatives thereof. This protein has the protein kinase activity and does not have the activated Rho protein binding activity.

The protein according to the present invention is a protein having the activated Rho protein binding activity and protein kinase activity, or a protein modified to damage either of these functions. The Rho protein is closely involved in cellular functions such as cell morphological change, cell motility, cell adhesion and cytokinesis as well as tumorigenesis and metastasis (see Takai, Y. et al.; G. C. Prendergast et al.; Khosravi-Far, R. et al.; R. Qiu et al.; Lebowitz, P. et al.; Yoshioka, K. et al. ibid.). Therefore, the protein according to the present invention is useful in investigating mechanisms of tumorigenesis and metastasis.

Also, the Rho protein is known to be involved in smooth muscle contraction (see K. Hirata et al.; M. Noda et al. ibid.). Therefore, the protein according to the present invention is useful in investigating mechanisms of various circular system diseases such as hypertension, vasospasm (cardiovascular vasospsm and cerebrovascular vasospsm), cardiac angina, myocardial infarction, and arteriosclerosis obliterans.

Base Sequence

The present invention provides a base sequence encoding the protein according to the present invention. Typical examples of such base sequences include base sequences comprising all or part of the DNA sequence of SEQ ID NO.2. Other typical examples of such base sequences include base sequences comprising all or part of the DNA sequence of SEQ ID NO.5.

As mentioned above, the DNA sequence in SEQ ID NO.2 was obtained from a cDNA library derived from bovine brain. This DNA sequence contains the open reading frame of bovine Rho-kinase, which starts at ATG (1–3) and ends at TAA (4165–4167).

The DNA sequence in SEQ ID NO.5 was obtained from a cDNA library derived from human brain. This DNA sequence contains the open reading frame of human Rho-kinase, which starts at ATG (1–3) and ends at TAA (4165–4167).

When the amino acid sequence is given, the base sequence encoding the amino acid sequence is easily determined, and a variety of base sequences encoding the amino acid sequence described in SEQ ID NO: 1 can be selected. The base sequence encoding the protein according to the present invention thus means, in addition to a part or all of the DNA sequence described in SEQ ID NO: 2, another sequence encoding the same amino acid sequence and containing a DNA sequence of a degenerate codon(s), and also includes RNA sequences corresponding to the DNA sequences.

The base sequence according to the present invention may be naturally occurred or obtained by synthesis. It may also be synthesized with a part of a sequence derived from the naturally occurring one. DNAs may typically be obtained by screening a chromosome library or a cDNA library in accordance with a conventional manner in the field of genetic engineering, for example, by screening a chromosome library or a cDNA library with an appropriate DNA probe obtained based on information of the partial amino acid sequence. The base sequence according to the present invention can be prepared, for example, from a bovine brain cDNA library by using the oligonucleotide corresponding to the peptide indicated by double underlines in FIG. 9 as a screening probe (see example 3).

The base sequences from nature are not specifically restricted to any sources; but may be derived from mammals, including human, or other sources.

Examples of base sequences encoding the protein according to the present invention include the DNA sequence 1–4167 of SEQ ID NO.2 (corresponding to the open reading frame), the DNA sequence 1261–3411, 2395–3411 or 2827–3204 of SEQ ID NO.2 (corresponding to the activated Rho protein binding domain), the DNA sequence 1312–3372 of SEQ ID NO.2 (corresponding to the coiled-coil domain), the DNA sequence 268–1077 or 16–1659 of SEQ ID NO.2 (corresponding to the kinase catalytic domain), the DNA sequence 2827–3204 of SEQ ID NO.5 (corresponding to the activated Rho protein binding domain), and the DNA sequence 268–1077 of SEQ ID NO.5 (corresponding to the kinase domain).

Vector and Transformed Host Cell

According to the present invention, we provide a vector comprising the aforementioned base sequence in such a manner that the vector can be replicable and express the protein encoded by the base sequence in a host cell. In addition, according to the present invention, we provide a host cell transformed by the vector. There is no other restriction to the host-vector system. It may express proteins fused with other proteins. Examples of the fusion protein expression system include those expressing MBP (maltose binding protein), GST (glutathione-S-transferase), HA (hemagglutinin), polyhistidine, myc, Fas and the like.

Examples of the vector include plasmid vectors such as expression vectors for prokaryotic cells, yeast, insect cells or animal cells, virus vectors such as retrovirus vectors, adenovirus vectors, adeno-associated virus vectors, herpesvirus vectors, Sendai virus vectors or HIV vectors, and liposome vectors such as cationic liposome vectors.

The vector according to the present invention may contain, in addition to the base sequence according to the present invention, other sequences for controlling the expression and a gene marker for selecting host cells. In addition, the vector may contain the base sequence according to the present invention in a repeated form (e.g. in tandem). The base sequences may also be introduced in a vector according to the conventional manner, and host cells may be transformed by the vector based on the method conventionally used in the field.

The vector according to the present invention may be constructed based on the procedure and manner which have been conventionally used in the field of genetic engineering.

Furthermore, examples of the host cell include *Escherichia coli*, yeast, insect cells, animal cells such as COS cells, lymphocytes, fibroblasts, CHO cells, blood cells, tumor cells, and the like.

The transformed host cell is cultured in an appropriate medium, and the protein according to the present invention can be obtained from the cultured product. Thus, according to another embodiment of the present invention, we provide a process for preparing the protein according to the present invention. The culture of the transformed host cell and culture condition may be essentially the same as those for the cell to be used. In addition, the protein according to the present invention may be recovered from the culture medium and purified according to the conventional manner.

The present invention can be applied to the gene therapy of malignant tumors by introducing a vector having the base sequence according to the present invention into cancer cells of an organism including human (e.g., leukemia cells, carcinoma cells in digestive tract, lung carcinoma cells, pancreas carcinoma cells, ovary carcinoma cells, uterus carcinoma cells, melanoma cells,. brain tumor cells, etc.) with an appropriate method and expressing the protein according to the present invention, i.e., by transforming the cancer cells of cancer patients.

When the protein according to the present invention (having the activated Rho protein binding activity and not having the protein kinase activity) is expressed in an organism including human, the activated Rho protein binds to the protein and, then, it intercepts the signal transduction from the activated Rho protein to Rho-kinase, thereby suppressing tumorigenesis or metastasis in which the Rho protein is involved.

As for vectors for gene therapy, see Fumimaro Takaku, Experimental Medicine (extra edition), Vol. 12, No. 15 "Forefront of Gene therapy" (1994).

Use/Pharmaceutical Compositions

As mentioned above, a protein having the activated Rho protein binding activity and not having the protein kinase activity is considered to interrupt signal transduction pathway from the activated Rho protein to Rho-kinase, by binding to the activated Rho protein (by inhibiting the binding between Rho-kinase and the activated Rho protein).

In the meantime, as mentioned above, the Rho protein is known to be closely involved in tumorigenesis or metastasis. According to the present invention, Rho-kinase receives signals from the Rho protein. Therefore, Rho-kinase is also considered to be closely involved in tumorigenesis and metastasis. Thus, a protein having the activated Rho-binding activity and not having the protein kinase activity should be useful in suppressing tumorigenesis or metastasis.

Therefore, a protein having the activated Rho protein binding activity and not having the protein kinase activity can be used as a agent suppressing tumorigenesis or metastasis in which the Rho protein in involved (i.e., which depends on signal transduction via the Rho protein (hereinafter referred to as a "tumorigenesis/metastasis suppressing agent").

Examples of such tumorigenesis and metastasis include tumorigenesis in which the Rho protein, other small G-proteins (e.g., Ras, Rac, Cdc42, Ral, etc.), small G-protein GDP•GTP-exchange proteins (e.g., Dbl, Ost, etc.), lysophosphatidic acid (LPA), receptor-type tyrosine kinase (e.g., PDGF receptor, EGF receptor, etc.), transcription regulating proteins (myc, p53, etc.), or various human tumor viruses are involved.

The inventors also found that myosin light chain phosphatase existing in smooth muscles and one of the subunits thereof, myosin-binding subunit (Y. H. Chen et al., FEBS Lett., 356, 51–55 (1994)), were the most suitable physiological substrates for Rho-kinase (see example 2 (3) and examples 5 and 6); that the phosphorylation of myosin light chain phosphatase (including myosin-binding subunit) inhibited the phosphatase activity thereof (see examples 5 and 6); and that the expression of the Rho protein resulted in the phosphorylation of myosin-binding subunit and myosin light chain in cells that are believed to endogenously express Rho-kinase (see example 6).

Furthermore, the inventors found that Rho-kinase phosphorylated both isolated myosin light chain and the myosin light chain of intact myosin in a GTP-Rho-dependent manner (see example 7); that the primary site of phosphorylation by Rho-kinase on myosin light chain was Ser-19, which was the site phosphorylated by myosin light chain kinase (see example 8); that the phosphorylation of the myosin light chain of intact myosin enhanced the MgATPase activity of the myosin light chain (see example 9); and that Rho-kinase derivative of which protein kinase activity had been constitutively activated enhanced smooth muscle contraction (see example 12).

Hence, the mechanism of the enhancement of smooth muscle contraction by the Rho protein is considered to be, but not restricted to, the following:

(1) The binding of the activated Rho protein to Rho-kinase enhances the kinase activity of the Rho-kinase.
(2) The Rho-kinase then phosphorylates the myosin-binding subunit of myosin light chain phosphatase.
(3) The phosphorylation suppresses the phosphatase activity of the myosin light chain phosphatase, and then the dephosphorylation of the myosin light chain is inhibited.
(4) As a result of the inhibition of dephosphorylation, the myosin remains phosphorylated.
(5) Also, the Rho-kinase in (1) phosphorylates myosin light chain.
(6) As a result of (4) and (5), association of myosin and actin is enhanced while their dissociation is suppressed.
(7) As a consequence, smooth muscle contraction is enhanced and maintained.

The model is shown in FIG. 22.

Therefore, a protein having the activated Rho-binding activity and not having the protein kinase activity can be used as a smooth muscle contraction suppressing agent or a agent for treatment of various circulatory system diseases such as hypertension, vasospasm (cardiovascular vasospasm and cerebrovascular vasospasm), cardiac angina, myocardial infarction, and arteriosclerosis obliterans.

The tumorigenesis/metastasis suppressing agent and the agent for treatment of cardiovascular disease according to the present invention may preferably be administered to humans and other animals perorally, but also parenterally (e.g., intramuscularly, intravenously, subcutaneously, intrarectally, percutaneously or pernasally), in any appropriate form designed for peroral or parenteral administration.

The agents for suppressing the tumorigenesis/metastasis and the agents for treatment of circular system desease may be prepared in either of preparation forms including oral agents such as tablets, capsules, granules, powders, pills, grains, and troches, injections such as an intravenous injection and an intramuscular injection, rectal agents, fatty suppositories, and water-soluble suppositories depending on their intended uses. These preparations may be prepared according to methods well known in the art with conventional excipients, fillers, binding agents, wetting agents, disintegrants, surfacactants, lubricants, dispersants, buffering agents, preservatives, dissolution aids, antiseptics, flavors, analgesic agents and stabilizing agents. Examples of the non-toxic additives which can be used include lactose, fructose, glucose, starch, gelatin, magnesium carbonate, synthetic magnesium silicate, talc, magnesium stearate, methylcellulose, carboxymethylcellulose or a salt thereof, acacia, polyethylene glycol, syrup, vaseline, glycerine, ethanol, propylene glycol, citric acid, sodium chloride, sodium sulfite, sodium phosphate, and the like.

The content of the protein according to the present invention in a pharmaceutical agent varies depending on its dosage forms. The pharmaceutical generally contains about 0.1—about 50% by weight, preferably about 1—about 20% by weight, of the protein.

The dose of the protein for the treatment of the tumorigenesis and metastasis and circular system desease may appropriately be determined in consideration of its uses and the age, sex and condition of a patient, and is desirably in the range of about 0.1—about 500 mg, preferably about 0.5—about 50 mg, per day for an adult, which may be administered once or divided into several portions a day.

The present invention provides a method for suppressing tumorigenesis or metastasis and a method for suppressing the enhancement of smooth muscle contraction, comprising introducing a protein having the activated Rho protein binding activity and not having the protein kinase activity into cells which tumor is formed in or may transfer to or into cells where smooth muscle contraction is enhanced. The effective dosage, the method and form of administration, etc., may be selected as described for the tumorigenesis/metastasis suppressing agent.

A base sequence encoding a protein having the activated Rho protein binding activity and not having the protein kinase activity may be used to suppress tumorigenesis, metastasis or the enhancement of smooth muscle contraction, by transforming the target cells using the vector having this base sequence. In other words, the base sequence can be used as a agent for gene therapy to suppress tumorigenesis or metastasis or a agent for gene therapy of cardiovascular diseases.

Screening Method

The present invention provides a method for screening a material inhibiting the binding between the activated Rho protein and the protein according to the present invention having the activated Rho protein binding activity, comprising:

(1) placing the material to be screened in a screening system containing the activated Rho protein and the protein according to the present invention having the activated Rho protein binding activity, and (2) measuring degree of the inhibition of the binding between the activated Rho protein and the protein according to the present invention having the activated Rho protein binding activity.

Examples of methods for "measuring degree of inhibition of binding" include a method to measure the binding between the protein according to the present invention and recombinant GTPγS•GST-RhoA in an cell-free system using glutathione Sepharose beads, a method to measure the binding between the protein according to the present invention and the Rho protein in a cell system (animal cells) by using immunoprecipitation and immunoblotting and by a two hybrid system (M. Kawabata, Experimental Medicine (in Japanese), 13, 2111–2120 (1995); A. B. Vojetk et al., Cell, 74, 205–214 (1993)). For example, the degree of inhibition of binding can be measured as described in example 1 or 4. In this specification, the term "measuring degree of inhibition of binding" refer to the meaning including measuring the presence or absence of the binding.

A system for screening may be either a cell or a cell-free system. Examples of cell systems include yeast cells, COS cells, E. coli, insect cells, nematode cells, lymphocytes, fibroblasts (3Y1 cells, NIH/3T3 cells, Rat1 cells, Balb/3T3 cells, etc.), CHO cells, blood cells, tumor cells, smooth muscle cells, cardiac muscle cells, nerve cells, myelocytes, gliacytes and astrocytes.

The material to be screened includes, but is not restricted to, for example, peptides, analogues of peptides, microorganism culture, organic compounds, etc.

The present invention also provides a method for screening a material inhibiting the protein kinase activity of the protein according to the present invention having the protein kinase activity or derivatives thereof, comprising:

(1) placing the material to be screened in a screening system containing the protein according to the present invention having the protein kinase activity or derivatives thereof, and (2) measuring degree of the inhibition of the protein kinase activity of the protein according to the present invention having the protein kinase activity or derivatives thereof.

The present invention also provides a method for screening a material inhibiting the protein kinase activity of the protein according to the present invention having the activated Rho protein binding activity and protein kinase activity or derivatives thereof or the enhancement of the activity, comprising:

(1) placing the material to be screened in a screening system containing the activated Rho protein and the protein according to the present invention having the activated Rho protein binding activity and protein kinase activity or derivatives thereof, and (2) measuring the degree of inhibition of the protein kinase activity of the protein according to the present invention having the activated Rho-binding activity and protein kinase activity or derivatives thereof or the degree of inhibition of the enhancement of the activity.

Examples of methods for measuring "degree of inhibition of the protein kinase activity" or "degree of inhibition of the enhancement of the protein kinase activity" include methods to measure the autophosphorylation activity or activity to phosphorylate any other substrate, or the degree of the enhancement of the activities in the presence of the activated Rho protein. For example, the degree of inhibition of the enhancement of the protein kinase activity can be measured as described in examples 2, 5 and 6 through 9. In this specification, measuring "degree of inhibition of the protein kinase activity" or "degree of inhibition of the enhancement of the protein kinase activity" refers to the meaning including measurements the presence or absence of the inhibition of the protein kinase activity or the presence or absence of the inhibition of the enhancement of the protein kinase activity.

As described in the examples, "degree of inhibition of the protein kinase activity" can be measured by using Rho-kinase derivative having the protein kinase activity and not having the Rho-binding activity (see examples 7 and 12). Such Rho-kinase derivative is a derivative of which the protein kinase activity has been constitutively activated.

As described in the examples, the activated Rho protein posttranslationally processed enhances the protein kinase activity of Rho-kinase more effectively than unprocessed one (see example 2 (4)). Therefore, the screening according to the present invention can be achieved more accurately by using the activated Rho protein posttranslationally processed.

Examples of substrates include non-physiological substrates, such as myelin basic protein, S6 peptide, αp KC, histone, vinculin, talin, metavinculin, caldesmon, filamin, α-actinin and MAP-4, and physiological substrates, such as myosin, myosin light chain, and myosin light chain phosphatase and one of the subunits thereof (myosin-binding subunit (MBS)).

As described in examples 2 and 5, phosphorylation is enhanced 5- to 15-fold when myosin-binding subunit is used as a substrate in the presence of the activated Rho protein, as compared to the absence thereof. Therefore, the screening according to the present invention can be achieved more accurately by using myosin-binding subunit as a substrate in the presence of the activated Rho protein.

Also, as described in example 7, the $K_m$ value of Rho-kinase drops to about ⅕ when myosin light chain is used as a substrate in the presence of the activated Rho protein, as compared to the absence thereof. Therefore, the screening according to the present invention can be achieved more accurately by using myosin or myosin light chain as a substrate in the presence of the activated Rho protein.

The screening system and the material to be screened may be determined as in the aforementioned screening method.

As mentioned above, the activated Rho protein is known to be closely involved in tumorigenesis, metastasis, and smooth muscle contraction. Therefore, the above two screening methods can also be used as a method for screening tumorigenesis/metastasis suppressor or smooth muscle contraction suppressor.

Peptides and Antibodies

The present invention provides a peptide consisting of the amino acid sequence of SEQ ID NO.3 and a peptide comprising the amino acid sequence of SEQ ID NO.3. Such peptide contains a partial amino acid sequence of bovine or human Rho-kinase; more specifically, such peptide is a peptide consisting of 14 amino acid residues, wherein a cystein (Cys) is added to the N-terminal of the amino acid sequence 669–681 of SEQ ID NO.1 or NO.4 (13 amino acid residues). The amino acid sequence 669–681 of SEQ ID NO.1 or NO.4 exists in the coiled-coil domain of Rho-kinase.

The peptide can be used as an antigen for obtaining an antibody to the protein according to the present invention. Also, as mentioned above, the protein according to the present invention (especially, Rho-kinase) is closely involved in tumorigenesis, metastasis, and smooth muscle contraction. Therefore, the peptide according to the present invention should be useful in investigating their mechanisms.

The present invention provides an antibody to a peptide consisting of the amino acid sequence of SEQ ID NO. 3 or a peptide comprising the amino acid sequence of SEQ ID NO. 3. In the present invention, antibodies include polyclonal and monoclonal antibodies.

Examples of peptides comprising the amino acid sequence of SEQ ID NO.3 include peptides wherein any amino acid sequence is added to the N-terminal and/or C-terminal of the amino acid sequence of SEQ ID NO.3, including the protein according to the present invention.

The antibody according to the present invention can be prepared using conventional methods in the art; for example, by injecting the peptide of SEQ ID NO.3 into an animal (e.g., rabbit, goat, rat, mouse or sheep) with any carrier (e.g., bovine serum albumin) and, after a given period, purifying the serum of the animal.

The peptide of SEQ ID NO.3 contains a partial amino acid sequence of Rho-kinase (the amino acid sequence 669–681 of SEQ ID NO.1 or NO.4). Therefore, the specific reaction (i.e., immune reaction) of said polyclonal antibody may indicate the existence of Rho-kinase or a modified protein thereof.

Therefore, according to another aspect of the present invention, we provide a protein recognized by the antibody, and the protein according to the present invention recognized by the antibody.

Also, according to another aspect of the present invention, we provide a method for detecting a material recognized by the antibody according to the present invention, comprising:

(1) placing the material to be detected in a detection system containing the antibody according to the present invention, and (2) measuring the degree of reaction between the material to be detected and the antibody according to the present invention.

Examples of methods for measuring the degree of reaction with the antibody according to the present invention include ELISA method, radioimmunoassay, Western blotting, immunoprecipitation, immunofluorescence (see, for example, Monoclonal Antibody Experiment Manual, Kodansha (1987)). For example, the degree of reaction can be measured as described in example 3 (4). In this specification, the term "measuring degree of reaction" refer to the meaning including measurements the presence or absence of any reaction.

The detection system for the detection method according to the present invention may contain latex particles, for example, in addition to the polyclonal antibody according to the present invention.

The present invention also provides a detection kit comprising the antibody according to the present invention for materials specifically reacting with the antibody. The term "detection kit" refer to the meaning including detection reagents, diagnostic reagents, and diagnostic kit for diseases in which the protein according to the present invention is involved.

Examples of the detection method according to the present invention include a detection method for materials specifically reacting with said antibody, comprising:

(1) placing the material to be detected in a detection system containing latex particles bearing the antibody according to the present invention, and (2) measuring the degree of aggregation of the latex particles.

The degree of aggregation of latex particles can be measured by a photometric technique, such as turbidimetry, nephelometry.

The detection kit according to the present invention may contain latex particles, as in the detection system. Such latex particles may bear antibody on the surface thereof. Also, the detection kit according to the present invention comprising latex particles may be used as described in the above example of the detection method.

Examples of materials to be detected include body fluid from animals including humans (e.g., serum, blood, etc.), urine, feces, tissue specimens, cells (e.g., tumor cells, etc.).

Examples of materials reacting specifically with the polyclonal antibody according to the present invention include bovine or human Rho-kinase and derivatives thereof (containing the amino acid sequence 669–681 of SEQ ID NO.1 or NO.4), and proteins containing the peptide of SEQ ID NO.3.

The protein kinase activity of materials reacting specifically with the polyclonal antibody according to the present invention (e.g., bovine or human Rho-kinase) is stimulated in the presence of the activated Rho protein. Also, physiological substrates for the protein kinase of Rho-kinase are, as described in the examples, the myosin-binding subunit of myosin light chain phosphatase and intact myosin. Furthermore, myosin light chain phosphatase comprising myosin-binding subunit has been proved to be involved in various circular system diseases attributed to smooth muscle contraction, such as hypertension, vasospasm (cardiovascular vasospasm and cerebrovascular vasospasm), cardiac angina, myocardial infarction, and arteriosclerosis obliterans, as mentioned above.

Therefore, the above detection method and detection kit may be used as a detection method and detection kit (including detection reagents, diagnostic reagents, and diagnostic kit) for diseases involving the protein according to the present invention or diseases involving the Rho protein, myosin light chain phosphatase, myosin-binding subunit, myosin, or myosin light chain, such as cardiovascular diseases.

EXAMPLES

The present invention is illustrated in more details in, but not restricted to, the following examples:

Example 1 Identification and Purification of Activated Rho-Binding Protein (1) Preparation of brain membrane extract A crude membrane fraction was prepared from 200 g of scissored bovine brain gray matter specimens, by suspending them in 300 ml homogenizing buffer (25 mM Tris/HCl at pH 7.5, 5 mM EGTA, 1 mM dithiothreitol (DTT), 10 mM $MgCl_2$, 10 $\mu M$ (p-amidinophenyl)-methanesulfonyl fluoride, 1 mg/l leupeptin, and 10% sucrose). The protein in the crude membrane fraction was extracted by the addition of homogenizing buffer containing 4 M NaCl. After shaking for 1 hour at 4° C., the membrane fraction was centrifuged at 20,000×g for 1 hour at 4° C. The supernatant was dialyzed three times, using Buffer A (20 mM Tris/HCl at pH 7.5, 1 mM EDTA, 1 mM DTT, and 5 mM $MgCl_2$). Then, solid ammonium sulfate was added to a saturated concentration of 40%. The precipitate at 0–40% ammonium sulfate concentration was resolved in 16 ml Buffer A and dialyzed three times by Buffer A to obtain the bovine brain membrane extract.

(2) Preparation of small G-protein affinity column

Glutathione-S-transferase (GST hereafter)-RhoA, GST-RhoA$^{Ala37}$, GST-Rac1 and GST-H-Ras were purified according to the method described in H. Shimizu et al., J. Biol. Chem., 269, 30407–30411 (1994); H. Shimizu et al., J. Biol. Chem., 269, 22917–22920 (1994), and loaded with guanine nucleotides. The GST-small G-proteins (24 nmol each) were immobilized on 1 ml glutathione-Sepharose column 4B and loaded on the column.

(3) GST-small G-protein affinity column chromatography

The proteins of the bovine brain membrane extract were eluted through a 1 ml glutathione-Sepharose column. The pass-through fraction was loaded onto a glutathione-Sepharose column containing 24 nmol of GST, GDP•GST-RhoA or GTPγS•GST-RhoA. GTPγS is a nonhydrolyzable analog of GTP. The proteins bound to the glutathione-Sepharose column were eluted by addition of 10 ml Buffer A containing glutathione or 1% 3-[(3-cholamidopropyl) dimethylammonio] propanesulfonic acid (CHAPS), and fractions of 1 ml each were collected. Aliquots of the eluates were subjected to SDS-PAGE followed by silver staining, according to the method described in U. K. Laemmli, Nature, 227, 680–685 (1970).

The result is shown in FIG. 1. A protein with a molecular weight of about 164 kDa (bovine Rho-kinase) appeared in fractions 2–10. Bovine Rho-kinase appeared in the eluate from the GTPγS•GST-RhoA affinity column but not from the GST or GDP•GST-RhoA affinity column. The protein was scarcely retained on the GTPγS•GST-RhoA$^{Ala37}$ (a mutant RhoA protein containing an amino acid substitution in the effector domain) affinity column. The bovine Rho-kinase was not eluted from the GTPγS•GST-Rac1 or GTPγS•GST-H-Ras affinity column either. Thus, it was proved that bovine Rho-kinase interacts specifically with activated RhoA via the effector domain.

(4) Purification of bovine Rho-kinase

In order to purify bovine Rho-kinase, the eluates from the glutathione-Sepharose affinity column containing GTPγS•GST-RhoA (fractions 3–10) were diluted with an equal volume of Buffer A and subjected to a Mono Q 5/5 column equilibrated with Buffer A. After washing the column with 10 ml of Buffer A, proteins were eluted with a linear gradient of NaCl (0–0.5 M) in Buffer A, and fractions of 0.5 ml each were collected.

Figure 2:
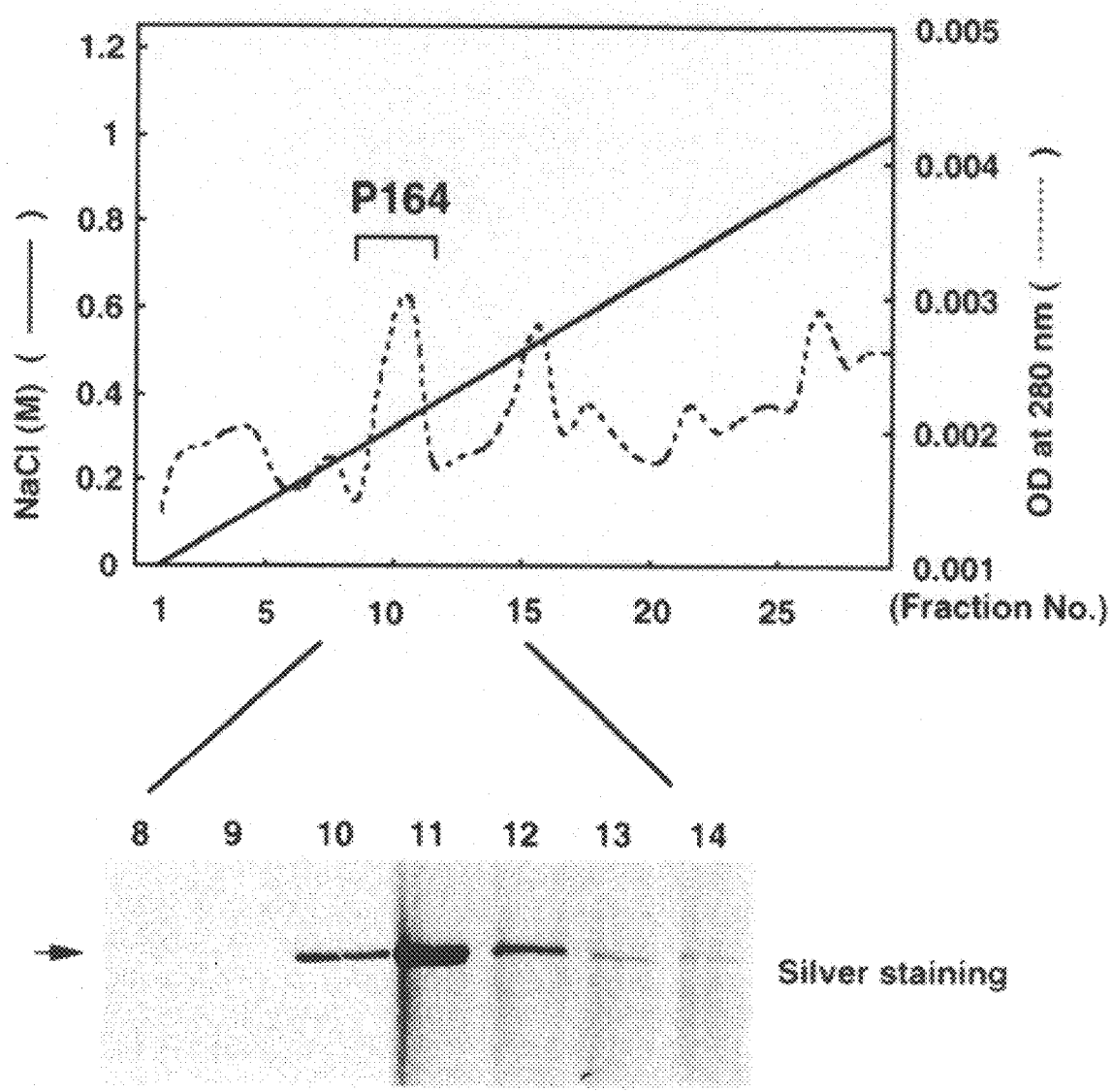
FIG. 2 is a diagram and an electrophoretic photograph showing results of the purification of bovine Rho-kinase by Mono Q column chromatography. The CHAPS-eluate was subjected to a Mono Q column and Rho-kinase was eluted with a linear gradient of NaCl. The results shown are representative of three independent experiments.

The result is shown in FIG. 2. Bovine Rho-kinase appeared as a single peak in fractions 10–12 (upper panel of FIG. 2). Aliquots of the eluates (fractions 8–14) subjected to SDS-PAGE followed by silver staining presented a purity of about 95% (lower panel of FIG. 2).

(5) Identification of Rho-binding protein by overlay assay

Overlay assay was carried out according a modified form of the method described previously (E. Manser et al., J. Biol. Chem., 267, 16025–16028 (1992)). The sample was applied to 6% SDS-PAGE and blotted to a nitrocellulose membrane. The membrane was incubated at 4° C. for 5 min with Buffer B (25 mM Hepes/NaOH at pH 7.0, 0.5 mM MgCl$_2$, and 0.05% Triton X-100) containing 6 M guanidium chloride and for 3 min with Buffer B. This was repeated four times and then an equal volume of Buffer B containing 6 M guanidium chloride was added. The membrane was agitated for 10 min and an equal volume of Buffer B was added 5 times sequentially at 10 min intervals. The membrane was soaked with Buffer B and transferred into phosphate buffer saline (PBS) containing 1% bovine serum albumin (BSA), 0.1% Triton X-100, 0.5 M MgCl$_2$, and 5 mM DTT. The membrane was soaked for 10 min with 0.5 ml of GAP buffer (25 mM Hepes/NaOH at pH 7.0, 2.5 mM DTT, 5 mM MgCl$_2$, 0.05% Triton X-100, and 100 mM GTP) containing [$^{35}$S]GTPγS•GST-RhoA or [$^{35}$S]GTPγS•GST-RhoA$^{Ala37}$. The membrane was washed three times with PBS containing 25 mM Hepes/NaOH at pH 7.0, 5 mM MgCl$_2$, and 0.05% Triton X-100, dried and exposed to an X-ray film for autoradiography. [$^{35}$S]GTPγS was purchased from DuPont New England Nuclear.

Figure 3:
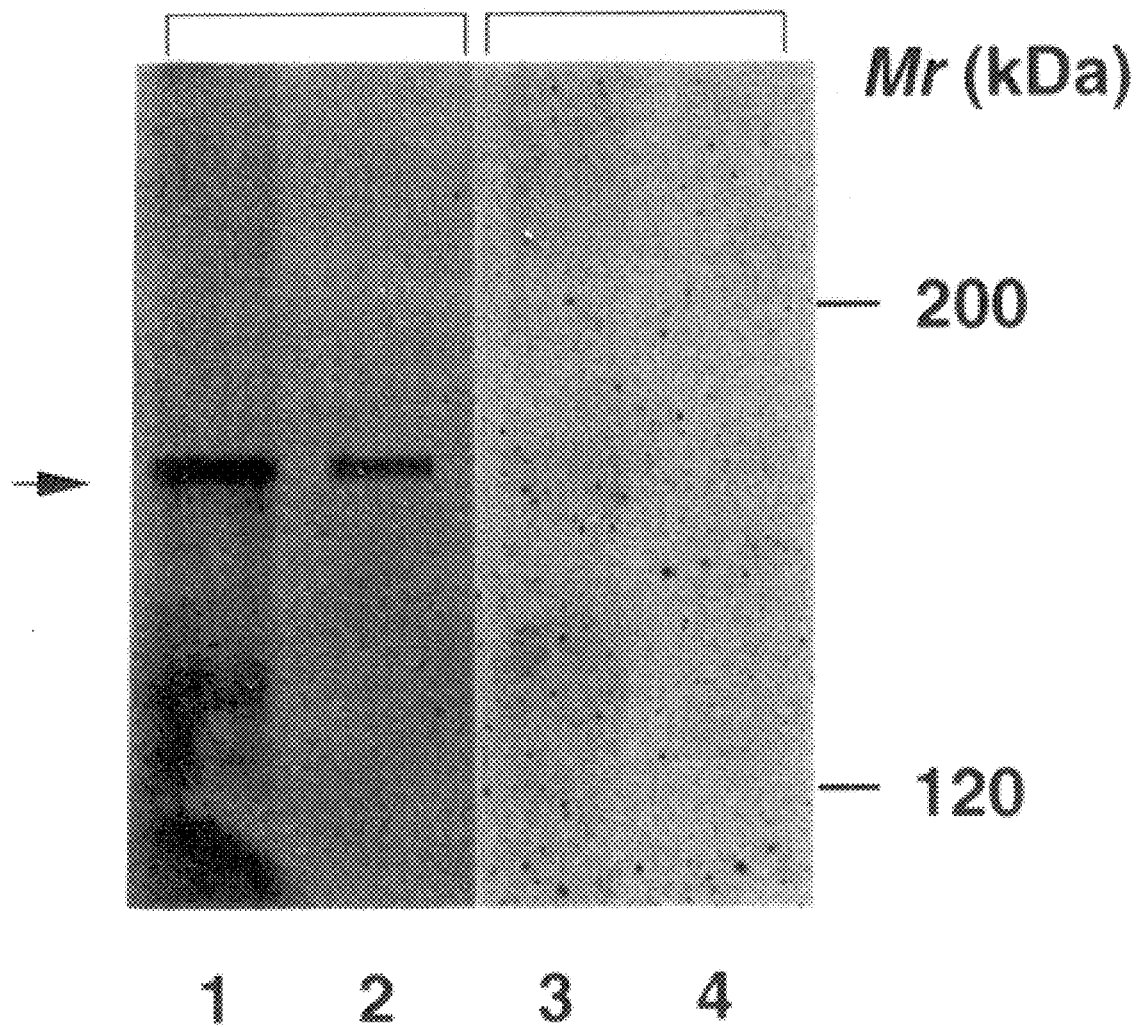
FIG. 3 is an electrophoretic photograph showing binding between bovine Rho-kinase and the activated RhoA. Lanes 1 and 3 indicate membrane extracts and lanes 2 and 4 indicate nitrocellulose filters containing purified Rho-kinase separated by SDS-PAGE. Lanes 1 and 2 were probed with [$^{35}$S]GTPγS•GST-RhoA and lanes 3 and 4 were probed with [$^{35}$S]GTPγS•GST-RhoA$^{Ala\ 37}$. An arrow indicates the position of Rho-kinase on SDS-PAGE. The results shown are representative of three independent experiments.

The result is shown in FIG. 3. [$^{35}$S]GTPγS•GST-RhoA bound to bovine Rho-kinase in the membrane extract and purified preparation, but [$^{35}$S]GTPγS•GST-RhoA$^{Ala37}$ did not bind to it, indicating that the activated RhoA protein directly binds to bovine Rho-kinase via the effector domain. GTPγS•GST-Rac1 did not bind to bovine Rho-kinase.

Example 2 Analysis of Bovine Rho-Kinase Activity

In order to examine whether bovine Rho-kinase has kinase activity, the following experiment was carried out: Kinase reaction was carried out in 50 µl of kinase buffer (50 mM Tris/HCl at pH 7.5, 1 mM EDTA, 5 mM MgCl$_2$, and 0.06% CHAPS) containing 2 µM [γ-$^{32}$P]ATP (600–800 MBq/mmol) and purified bovine Rho-kinase (10 ng of protein) with or without substrates (myelin basic protein, S6 peptide or serine-containing synthetic peptides based on the protein kinase C pseudosubstrate (αPKC), 40 µM each). After incubation for 10 min at 30° C., the reaction mixtures were boiled in SDS-sample buffer and subjected to SDS-PAGE for autophosphorylation assay. The radiolabeled bands were visualized by autoradiography. The reaction mixtures were spotted onto a Whatman p81 paper for kinase assay. Incorporation of $^{32}$P into the substrate was assessed by scintillation counting. The result is shown below. [γ-$^{32}$P]ATP was purchased from Amersham Corp.

(1) The enhancement of the autophosphorylation activity of bovine Rho-kinase by the activated RhoA protein is shown in FIG. 4.

Purified bovine Rho-kinase exhibited autophosphorylation in vitro in the presence of [γ-$^{32}$P]ATP. The autophosphorylation was stimulated by GTPγS•GST-RhoA by about two times (lane 3). GTPγS•GST-RhoA$^{Ala37}$ (lane 4) and GDPγS•GST-RhoA (lane 2) were less effective. The concentration of GST-RhoA used was 1 µM each.

Figure 5:
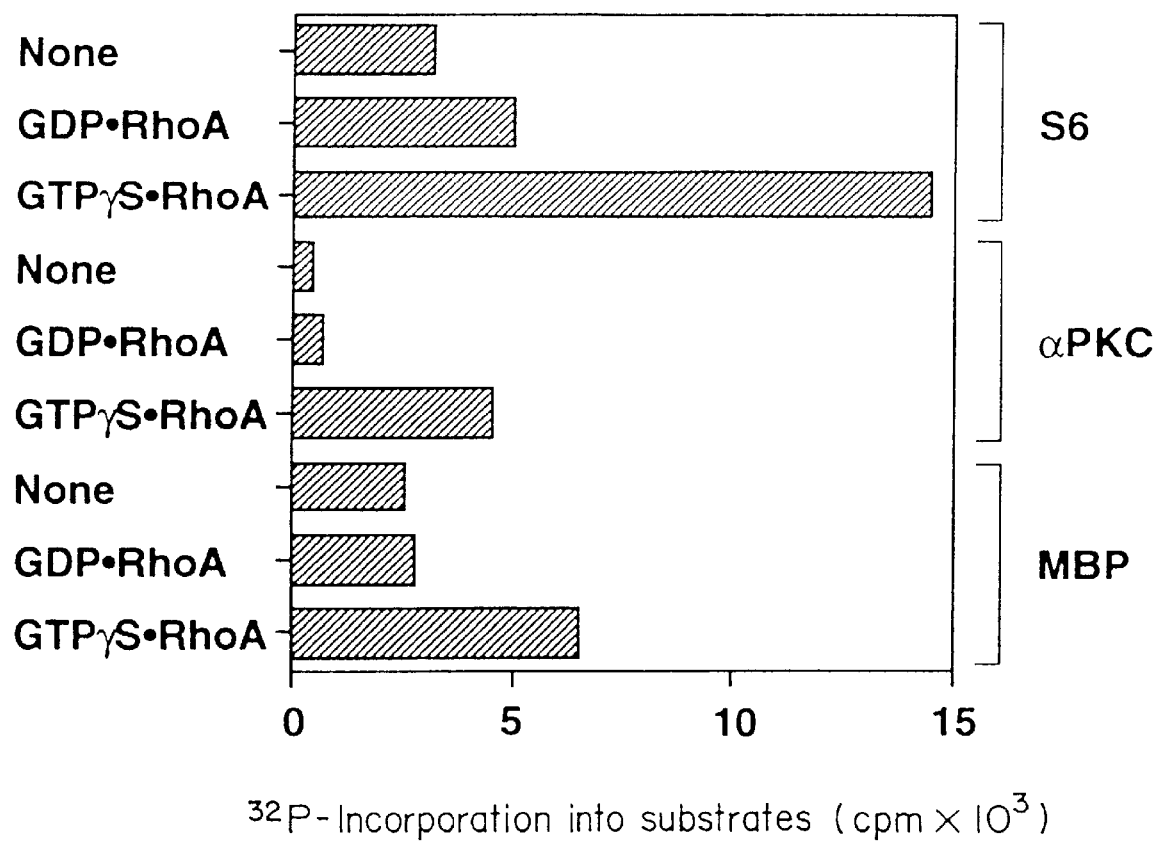
FIG. 5 shows degrees of phosphorylation of myelin basic protein, S6 peptide, or αPKC (40 μM each) in the presence of either GST, GDP•GST-RhoA, or GTPγS•GST-RhoA by bovine Rho-kinase.

(2) The enhancement of bovine Rho-kinase activity by the activated RhoA protein in the presence of non-physiological substrates is shown in FIGS. 5 and 6.

Bovine Rho-kinase exhibited kinase activity in the absence of GST-Rho when myelin basic protein, S6 peptide, and αPKC were used as substrates (FIGS. 5 and 6). The phosphorylation of myelin basic protein, S6 peptide and αPKC by bovine Rho-kinase was stimulated by GTPγS•GST-RhoA, whereas GDP•GST-RhoA had a much weaker effect (FIG. 5). The phosphorylation of S6 peptide was stimulated by GTPγS•GST-RhoA, while GTPγS•GST-H-Ras and GDP•GST-H-Ras had no effect and GTPγS•GST-RhoA$^{Ala37}$, GTPγS•GST-Rac1 and GDP•GST-Rac1 showed only marginal effects (FIG. 6). Among the three substrates, S6 peptide was the most preferable substrate for bovine Rho-kinase. The concentration of GST-small G-protein used was 1 µM each.

Figure 7:
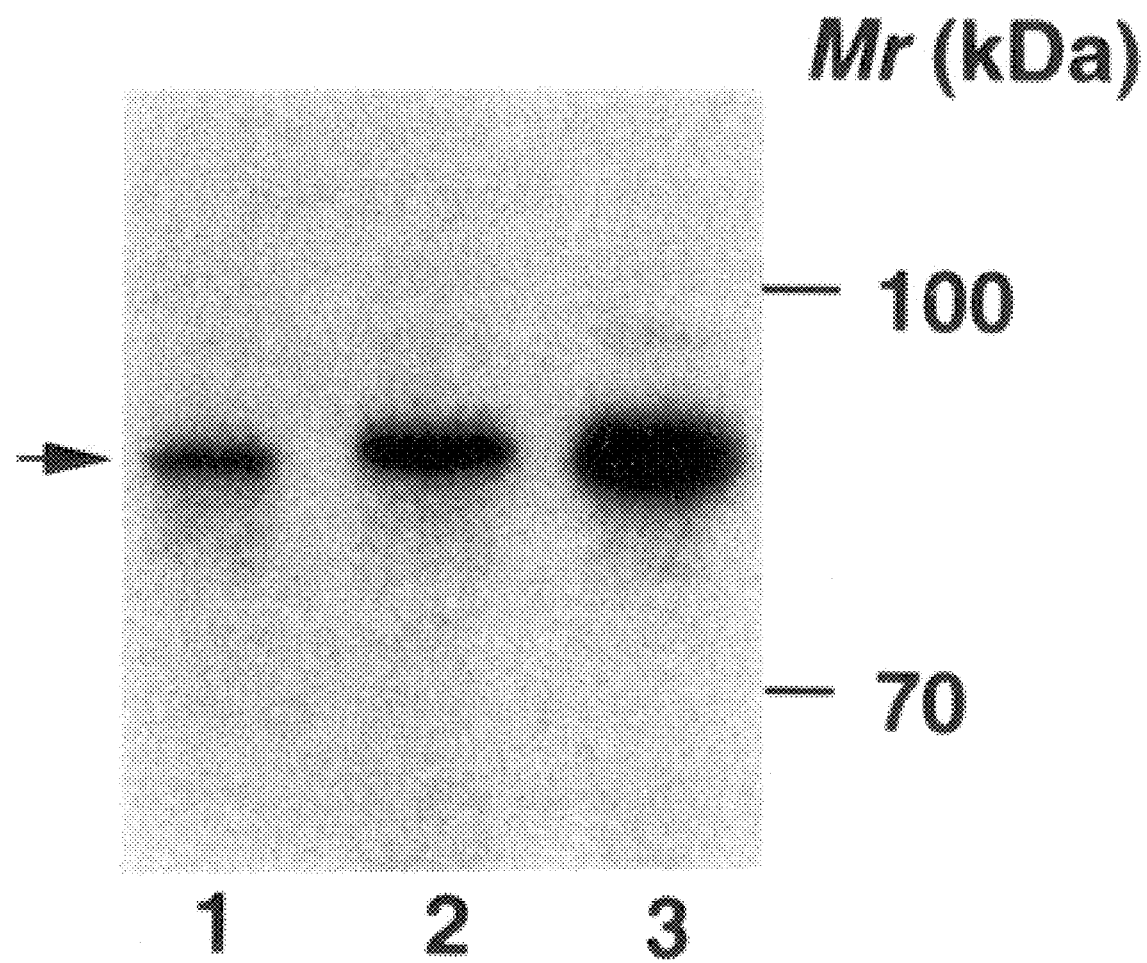
FIG. 7 is an electrophoretic photograph showing enhancement of the phosphorylation of rat myosin-binding subunit by bovine Rho-kinase in the presence of GTPγS•GST-RhoA. Lane 1: GST, Lane 2: GDP•GST-Rho, Lane 3: GTPγS•GST-RhoA. An arrow indicates the position of myosin-binding subunit protein on SDS-PAGE.

(3) The enhancement of bovine Rho-kinase activity by the activated RhoA protein in the presence of proteins as physiological substrates is shown in FIG. 7.

Since the Rho protein is implicated in cytoskeletal rearrangements, we searched for substrates for bovine Rho-kinase according to the above conditions among cytoskeletal regulatory proteins including vinculin, talin, metavinculin, caldesmon, filamin, vimentin, α-actinin (E. A. Clark & J. S. Brugge, Science, 268, 233–239, (1995)), MAP-4 (H. Aizawa et al., J. Biol. Chem., 265, 13849–13855 (1990)), and the myosin-binding subunit of myosin phosphatase (Y. H. Chen et al., FEBS Lett., 356, 51–55 (1994)). The myosin-binding subunit used was the C-terminus of rat myosin-binding subunit (the amino acid sequence 699–976) fused with maltose-binding protein. This fusion protein was expressed in E. coli and purified according to the standard procedure.

Bovine Rho-kinase phosphorylated the above substrates in the presence and absence of GST-RhoA. The enhancement of the phosphorylation level in the presence of GTPγS-RhoA was minor when the substrate was vinculin, talin, metavinculin, caldesmon, filamin, vimentin, α-actinin or MAP-4 (not shown). However, when the substrate was myosin-binding subunit (50 nM), the phosphorylation level was substantially enhanced in the presence of GTPγS•GST-RhoA (FIG. 7). GTPγS•GST-RhoA enhanced the phosphorylation of the myosin-binding subunit by about 15 times (FIG. 7). The concentration of GST-RhoA used was 1 μM each.

(4) Effect of posttranslational processing of RhoA

It has been known that posttranslational processing of the Ras protein is important for the activation of yeast adenylate cyclase (H. Horiuchi et al., Mol. Cell. Biol., 12, 4515–4520 (1992)) and Ras-dependent MAP kinase kinase kinase (B-Raf) (T. Itoh et al., J. Biol. Chem., 268, 3025–3028 (1993)). Also, posttranslational processing of the Rac protein is important for the activation of NADPH oxidase (S. Ando et al., J. Biol. Chem., 267, 25709–25713 (1992)). These observations prompted us to examine whether posttranslational processing of the RhoA protein affects for the activation of bovine Rho-kinase. The RhoA protein was posttranslationally processed according to the procedure described in H. Horiuchi et al., Mol. Cell. Biol., 12, 4515–4520 (1992) and T. Itoh et al., J. Biol. Chem., 268, 3025–3028 (1993), and used to examine the effect of processing on the kinase activity of bovine Rho-kinase according to the aforementioned procedure.

The result is shown in FIG. 8. Posttranslationally processed RhoA protein in the GTPγS-bound form stimulated the kinase activity of S6 peptide more effectively than posttranslationally unprocessed RhoA.

Example 3 Amino Acid Sequence of Bovine Rho-Kinase and DNA Sequence encoding amino acid sequence (1) Peptide sequencing Purified bovine Rho-kinase was subjected to SDS-PAGE and transferred to a polyvinylidene difluoride membrane. The band corresponding to bovine Rho-kinase was digested with lysyl-endopeptidase, Achromobacter protease I, or endoproteinase Asp-N (A. Iwamatsu, Electrophoresis, 13, 142–147 (1992)), and the peptides released were fractionated by C18 column chromatography and sequenced. A total of 37 internal sequences were obtained from the peptides.

(2) cDNA cloning.

To obtain cDNA clones encoding bovine Rho-kinase, a bovine brain cDNA library (1.2×106 independent plaques in total) (CLONTECH) was screened with degenerate oligonucleotide probes corresponding to the partial amino acid sequence determined from the purified bovine Rho-kinase (indicated by double underlines in FIG. 9). Hybridization for screening of the library was done as described previously (J. Sambrook et al., Molecular Cloning: A Laboratory Manual: Cold Spring Habor Laboratory, Cold Spring Harbor, N.Y. (1989)). The cDNA inserted into isolated positive clone of λgt10 phage was cloned into pBluescript II SK(-) (M. A. Alting-Mees & J. M. Short, Nucleic Acids Res., 17, 9494 (1989)) for nucleotide sequencing with ABI DNA sequencer 373S.

(3) Sequencing

The cDNA base sequence and deduced amino acid sequence of bovine Rho-kinase are shown in SEQ ID NO.2 and NO.1, respectively. The protein predicted from the cDNA sequence contains 1388 amino acid residues with a calculated molecular mass of 160,797 Da, which is close to the apparent molecular mass, about 164 kDa, estimated by SDS-PAGE. All thirty-seven peptide sequences obtained were found within the amino acid sequence deduced from the cDNA sequence, as indicated by single underlines in FIG. 9.

Bovine Rho-kinase had a 260 amino acid sequence on the N-terminal (corresponding to the amino acid sequence 90–359 in SEQ ID NO.1), which shared 72% sequence identity with the kinase domain of myotonic dystrophy kinase (J. D. Brook et al., Cell, 68, 799–808 (1992); Y. H. Fu et al., Science, 255, 1256–1258 (1992); M. Mahadevan et al., Science, 255, 1253–1255 (1992)), a type of serine/threonine kinase. Bovine Rho-kinase had a putative coiled-coil structure in the middle (the amino acid sequence 438–1124 in SEQ ID NO.1), which showed a similarity to myosin rod, and a zinc finger-like motif on the C-terminal (the amino acid sequence 1261–1315 in SEQ ID NO.1).

Figure 10:
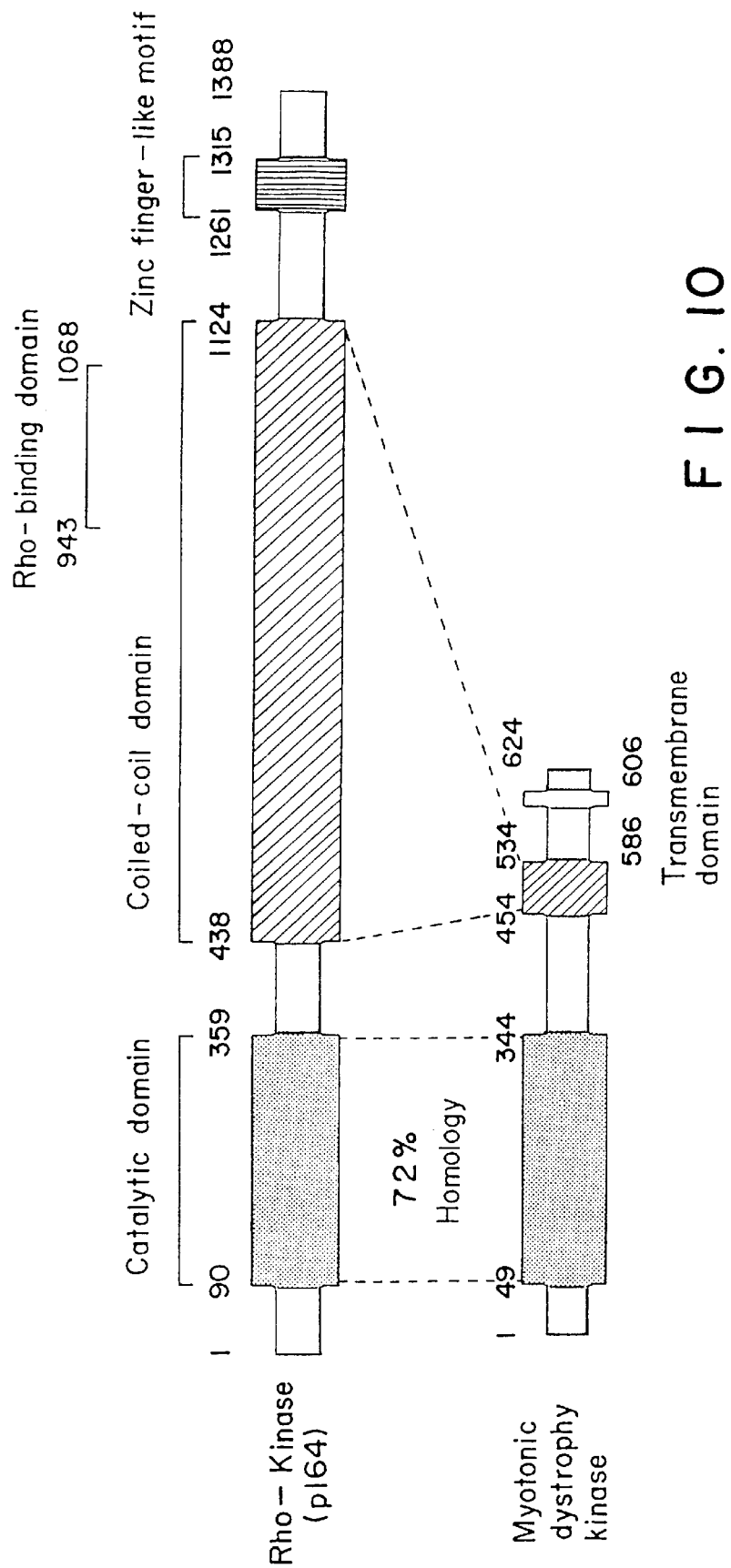
FIG. 10 comparatively shows the domain structures of bovine Rho-kinase and myotonic dystrophy kinase.

Comparison of the kinase domain, coiled-coil domain, and zinc finger motif between bovine Rho-kinase and myotonic dystrophy kinase is shown in FIG. 10. The BLAST program was used for protein homology search (S. F. Altschul et al., J. Mol. Biol., 215, 403–410 (1990)).

(4) Analysis of tissue-specific expression using antibody production and immunoblotting Rabbit polyclonal antibodies against the partial amino acid sequence 669–681 of bovine Rho-kinase (KRQLQERFTDLEK) was prepared according to standard techniques, by immunizing a rabbit using a synthetic peptide (CKRQLQERFTDLEK, corresponding to the amino acid sequence in SEQ ID NO.3) as an antigen and bovine serum albumin as a carrier, and purifying the obtained serum.

Immunoblot analysis of bovine Rho-kinase was carried out as described (E. Harlow & D. Lame, Antibodies: A Laboratory Manual: Cold Spring Harbor Laboratory, Cold Spring Harbor, N.Y. (1988)). Protein concentrations were determined with bovine serum albumin as a reference protein as described (M. Bradford, Anal. Biochem., 72, 248–254 (1976)). The anti-bovine Rho-kinase antibodies from rabbit crossreacted with rat Rho-kinase.

Figure 11:
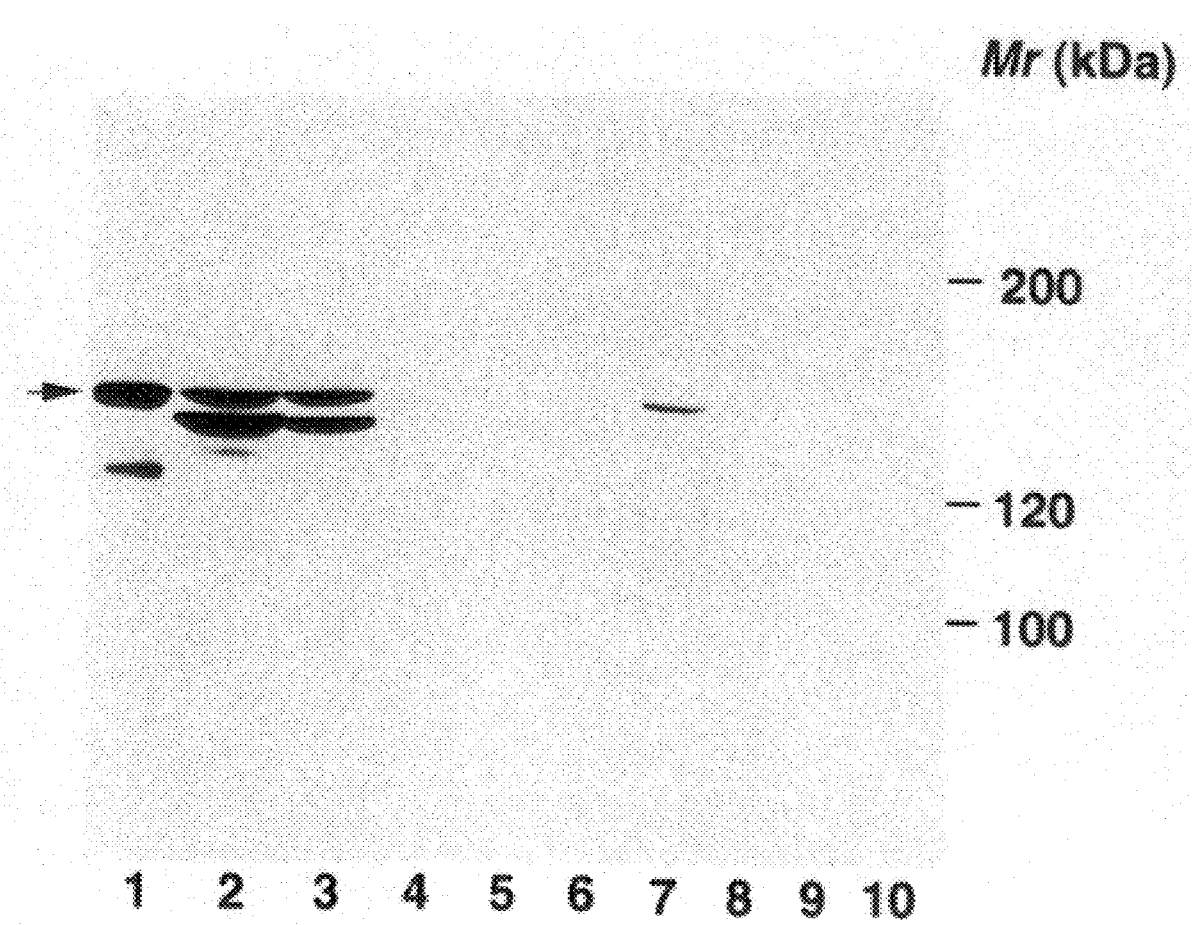
FIG. 11 is an electrophoretic photograph showing the tissue distribution of bovine Rho-kinase expression. Lane 1: 1% CHAPS-elute from the GST-RhoA affinity column, Lane 2: cerebrum, Lane 3: cerebellum, Lane 4: heart, Lane 5: skeletal muscle, Lane 6: spleen, Lane 7: lung, Lane 8: liver, Lane 9: kidney, Lane 10: pancreas. An arrow indicates the position of Rho-kinase on SDS-PAGE.

The result is shown in FIG. 11. The tissue specificity of bovine Rho-kinase expression was analyzed in various rat tissues. Rho-kinase was expressed highly in cerebrum and cerebellum, weakly in heart, spleen, thymus, lung and kidney, and hardly in skeletal muscles, liver and pancreas.

Example 4 Binding between Activated RhoA Protein and Recombinant Bovine Rho-Kinase (1) Plasmid construction To obtain the in vitro-translated coiled-coil domain of bovine Rho-kinase, pGEM-HA-Rho-kinase was constructed as follows: The 2.2 kbp cDNA fragment of bovine Rho-kinase encoding the amino acid sequence 421–1137 in SEQ ID NO.1 was amplified from the bovine Rho-kinase cDNA clone (example 3 (2)) by PCR using the primers (SEQ ID NOS. 7 & 8 Respectively) 5'-ATAAGGATCCCTACTAAGTGACTCTCCATCTTG-3' and 5'-TATAGGATCCTTAACTGCCTATACTGGAACTATCC- 3'. The amplified cDNA fragment was cloned into the BamHI site of pGEM-HA.

(2) In vitro translation

In vitro translation of pGEM-HA-Rho-kinase was performed using the TNT T7-coupled reticulocyte lysate system (Promega) under the conditions described in the instruction manual, to obtain a protein corresponding to the coiled-coil domain of bovine Rho-kinase. GST-small G-proteins loaded with guanine nucleotides (0.75 nmol each) were immobilized onto 31 µl of glutathione-Sepharose 4B beads and washed with 310 µl (10 volumes) of Buffer A. The immobilized beads were added to 30 µl of in vitro-translated mixture and incubated for 1 h at 4° C. with gentle mixing in the presence of 1 mg/ml bovine serum albumin. The beads were washed six times with 102 µl (3.3 volumes) of Buffer A, and the bound proteins were eluted with GST-small G-proteins by addition of 102 µl (3.3 volumes) of Buffer A containing 10 mM glutathione three times. The first eluates were subjected to SDS-PAGE and vacuum-dried followed by autoradiography. The result is shown in FIG. 12.

The in vitro-translated coiled-coil domain of bovine Rho-kinase was retained on the GTPγS•GST-RhoA affinity beads and could be coeluted with GTPγS•GST-RhoA by addition of glutathione (lane 3), whereas it was not retained on the GST (lane 1), GDP•GST-RhoA (lane 2), GTPγS•GST-RhoA$^{Ala37}$ (lane 4), GTPγS•GST-Rac1 (lane 6) and GTPγS•GST-H-Ras (lane 8) affinity beads. Also, essentially the same binding patterns were obtained when a protein corresponding to a sequence overlapping the coiled-coil domain of bovine Rho-kinase (the amino acid sequence 799–1137 in SEQ ID NO.1) was used (not shown). These results confirm that GTPγS•GST-RhoA directly interacts with the coiled-coil domain of bovine Rho-kinase.

Also, the Rho-binding domain of human Rho-kinase was determined by two hybrid system, as described later (example 11). The results suggested that the Rho-binding domain of bovine Rho-kinase was the amino acid sequence 943–1068 in SEQ ID NO.1 (FIG. 10).

Figure 13:
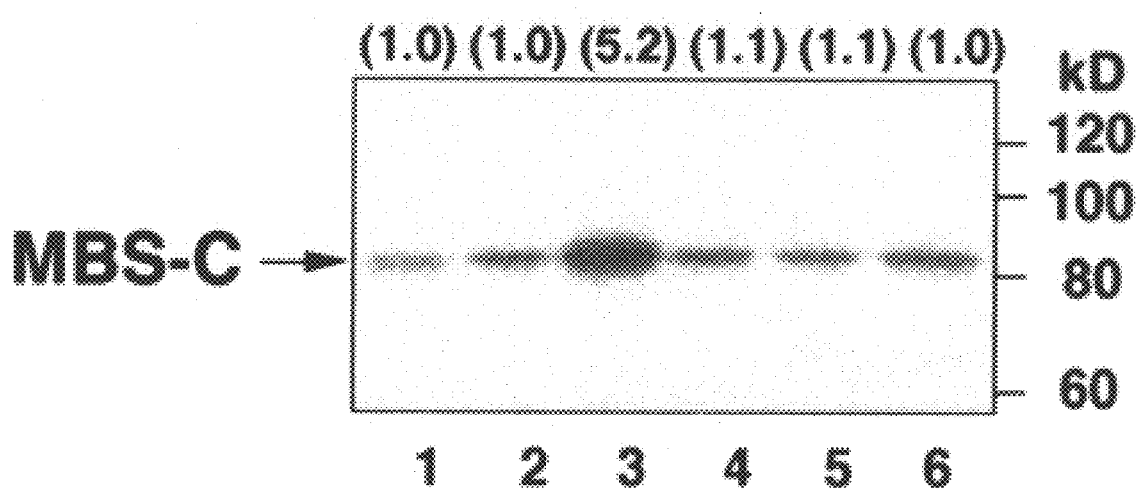
FIG. 13 is an electrophoretic photograph showing enhancement of the phosphorylation of chicken myosin-binding subunit by bovine Rho-kinase in the presence of GTPγS•GST-RhoA. Lane 1: GST, Lane 2: GDP•GST-RhoA, Lane 3: GTPγS•GST-RhoA, Lane 4: GTPγS•GST-RhoA$^{Ala37}$, Lane 5: GDP•GST-Rac1, Lane 6: GTPγS•GST-Rac1. The values in parentheses show fold stimulation relative to Rho-kinase incubated with GST alone (lane 1).

Example 5 Phosphorylation of Chicken Myosin-Binding Subunit and Inhibition of Myosin Light Chain Phosphatase Activity by Bovine Rho-Kinase (1) Phosphorylation of chicken myosin-binding subunit by bovine Rho-kinase Bovine Rho-kinase phosphorylated chicken myosin-binding subunit. The C-terminal domain (the amino acids 753–1004) of chicken myosin-binding subunit (Shimizu, H. et al., J. Biol. Chem., 269, 30407–30411 (1994)) was fused with maltose-binding protein (MBS-C) according to the method described in example 2 (3) and used as a substrate for the measurement of phosphorylation by bovine Rho-kinase according to example 2 (3) (FIG. 13). Phosphorylation of MBS-C by bovine Rho-kinase was at least five times as high in the presence of GTPγS•GST-RhoA (lane 3) as in the presence of GST (control, lane 1). On the contrary, GDP•GST-RhoA (lane 2), GTPγS•GST-RhoA$^{Ala37}$ (lane 4), GDP•GST-Rac1 (lane 5) and GTPγS•GST-Rac1 (lane 6) did not enhance the phosphorylation.

Bovine Rho-kinase did not phosphorylate the N-terminal domain (the amino acids 1–721) of chicken myosin-binding subunit (Shimizu, H. et al., J. Biol. Chem., 269, 30407–30411 (1994)), unlike MBS-C (not shown).

(2) Inhibition of chicken myosin light chain phosphatase activity by bovine Rho-kinase Natural myosin light chain phosphatase was purified from chicken gizzard according to the method described in Shimizu, H. et al., J. Biol. Chem., 269, 30407–30411 (1994). Phosphorylation of the myosin light chain phosphatase was measured in the presence of various concentrations of natural Rho-kinase from bovine brain (experiment 1). Also, the enzymatic activity of myosin light chain phosphatase that was phosphorylated at various bovine Rho-kinase concentrations was measured (experiment 2).

It was elucidated that the myosin-binding subunit of myosin light chain phosphatase was phosphorylated by bovine Rho-kinase in a dose-dependent manner, and that the enzymatic activity of myosin light chain phosphatase was inhibited by the phosphorylation by bovine Rho-kinase. FIG. 14 shows the results of the above two independent experiments (experiments 1 and 2), with the concentration of bovine Rho-kinase taken on the horizontal axis. The procedures for experiments 1 and 2 are as follows:

The phosphorylation of natural myosin light chain phosphatase by bovine Rho-kinase (experiment 1) was measured in 40 µl of reaction mixture (34 mM Tris/HCl at pH 7.5, 34 mM KCl, 4 mM MgCl$_2$, 1.625 mM EDTA, 1.2 mM DTT, 1.3% sucrose, 0.38% CHAPS, and 10 µM [$^{35}$S]ATPγS) containing purified myosin light chain phosphatase (1.0 µg of protein) and various amounts of bovine Rho-kinase, with or without 1 µM GTPγS•GST-RhoA. After incubation for 3 min, the reaction mixtures were subjected to SDS-PAGE. The phosphorylation of myosin-binding subunit was measured by autoradiography (Fuji BAS-2000).

In order to examine the effect of phosphorylation of myosin light chain phosphatase on its activity (experiment 2), myosin light chain phosphatase (1.0 µg of protein) purified in the same manner as above was phosphorylated by various concentrations of bovine Rho-kinase, in the presence or absence of non-radiolabeled 10 µM ATPγS and in the presence or absence of 1 µM GTPγS•GST-RhoA. The reaction was terminated by the addition of 5 µl of 46 mM EDTA. Then, reaction was started by adding 5 µl of 30 mM Tris/HCl at pH 7.5, 30 mM KCl, 0.5 mM DTT containing radiolabeled myosin light chain, to make 50 µl of reaction mixture (containing 5 µM $^{32}$P-myosin light chain), and continued for 6 min at 30° C. After terminating the reaction, the amount of $^{32}$P binding to myosin light chain was measured as described in Ishihara, H. et al., Biochem. Biophys. Res. Commun., 159, 871–877 (1989).

Myosin-binding subunit was $^{35}$S-thiophosphorylated by bovine Rho-kinase in a dose-dependent manner, as shown in FIG. 14.

Also, bovine Rho-kinase inhibited myosin light chain phosphatase activity in a dose-dependent manner in the presence of ATPγS, but did not in its absence. These results show that the enzymatic activity of myosin light chain phosphatase is inhibited as it is phosphorylated by bovine Rho-kinase.

Example 6 Measurement of Enhancement of Phosphorylation of Myosin-Binding Subunit and Myosin Light Chain by Rho Protein in NIH/3T3 Cells We examined whether the phosphorylation of myosin-binding subunit is enhanced by Rho protein in NIH/3T3 cells as follows: NIH/3T3 cells were stably transfected with p3'SS and pOPRSVI-HA-RhoA or pOPRSVI-HA-RhoA$^{Val14}$ according to the manufacturer's (Stratagene) instructions, to establish NIH/3T3 cell lines expressing hemagglutinin (HA)-RhoA or HA-RhoA$^{Val14}$ under the control of IPTG. Confluent NIH/3T3 cell lines (the parent cells, NIH/3T3 RhoA-5, NIH/3T3 RhoA-24, NIH/3T3 RhOA$^{Val14}$-7 and NIH/3T3 RhoA$^{Val14}$-25) cultured in 35 mm dish were treated with 5 mM IPTG for 24 hours. During the last 12 hours, the cells were deprived of serum, and then labeled with 9.25 MBq of [$^{32}$P]-ortho-phosphate for 2 hours. The $^{32}$P-labeled cells were lysed, and myosin-binding subunit was immunoprecipitated. The washed immunoprecipitates were subjected to SDS-PAGE and autoradiography.

Figure 15:
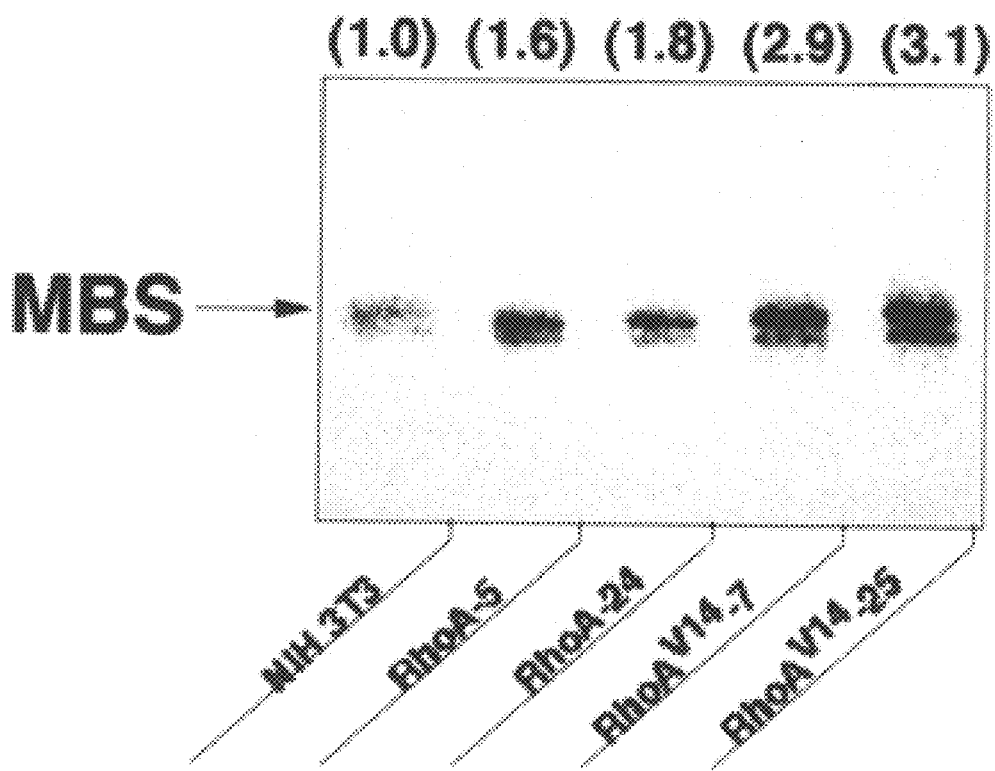
FIG. 15 is an electrophoretic photograph showing degree of myosin-binding subunit phosphorylation in each NIH/3T3 cell line overexpressing RhoA or RhoA$^{Val14}$. The values in parentheses show fold stimulation of myosin-binding subunit relative to that in the absence of thansfected RhoA (lane 1).

In the NIH/3T3 cell lines overexpressing RhoA or RhoA$^{Val14}$, large amounts of stress fibers and focal adhesions were observed as reported in A. J. Ridley & A. Hall, Cell, 70, 389–399 (1992) and A. J. Ridley & A. Hall, EMBO J., 13, 2600–2610 (1994). Although the amount of myosin-binding subunit was similar between the NIH/3T3 cell lines including the parent cells (not shown), the amounts of phosphorylation of myosin-binding subunit in the NIH/3T3 cell lines overexpressing RhoA or RhoA$^{Val14}$ were remarkably greater than that in the parental NIH/3T3 cells (FIG. 15).

Next, phosphorylation of myosin light chain in the NIH/3T3 cell lines overexpressing RhoA or RhoA$^{Val14}$ and the parent cells was measured as follows: IPTG-treated and serum-deprived NIH/3T3 cell lines (100 mm dish) were treated with 10% TCA. To determine the extent of myosin light chain phosphorylation, the trichloroacetic acid (TCA)-precipitable material was subjected to glycerol-urea gel electrophoresis followed by quantitation of the relative amounts of non-phosphorylated and phosphorylated (monophosphorylated (MLCP) and diphosphorylated (MLCP$_2$)) forms of myosin light chain by an immunoblot technique (D. A. Taylor & J. T. Stull, J. Biol. Chem., 263, 14456 (1988)). When the NIH/3T3 cells were treated with 0.1 μM phosphatase inhibitor (calyculin-A (CLA)) for 10 min, phosphorylation of myosin light chain was enhanced (FIG. 16). Phosphorylation of myosin light chain in the NIH/3T3 cell lines overexpressing RhoA or RhoA$^{Val14}$ was clearly higher than in the parent cells (FIG. 16). The result was consistent between three independent NIH/3T3 cell lines overexpressing RhoA or RhoA$^{Val14}$.

The mechanism underlying the above results is considered to be, but not restricted to, that the induced expression of RhoA or RhoA$^{Val14}$ in the NIH/3T3 cells stimulated their endogenous Rho-kinase, which then enhanced the phosphorylation of myosin-binding subunit, inhibiting myosin light chain phosphatase activity and, thus, inhibiting the dephosphorylation of myosin light chain.

Example 7 Phosphorylation of Myosin Light Chain by Bovine Rho-Kinase

We examined whether bovine Rho-kinase phosphorylates isolated myosin light chain in a cell-free system as follows:

Myosin light chain (Hathaway, D. R. & Haeberle, J. R. Anal. Biochem., 135, 37–43 (1983)), myosin and myosin light chain kinase (Ikebe, M. & Hartshorne, D. J., J. Biol. Chem., 260, 10027–10031 (1985)) were purified from frozen chicken gizzard. Bovine Rho-kinase was purified from bovine brain (example 1).

Protein fragment corresponding to the catalytic domain of bovine Rho-kinase were fused with GST to make a recombinant protein (GST-Rho-kinase) as follows. The cDNA fragment encoding the catalytic domain of bovine Rho-kinase (the amino acid sequence 6–553 in SEQ ID NO.1) was inserted into the BamH1 site of plasmid pAcYM1-GST (Matsuura, Y. et al., J. Gen. Virol., 68, 1233–1250 (1987)). GST-Rho-kinase was expressed in Sf9 cells (ATCC CRL 1711) and purified using this recombinant plasmid and a Baculovirus system as described in Matsuura, Y. et al., J. Gen. Virol., 68, 1233–1250 (1987).

The kinase reaction for bovine Rho-kinase was carried out in 50 μl of reaction mixture (50 mM Tris/HCl at pH 7.5, 2 mM EDTA, 1 mM DTT, 7 mM MgCl$_2$, 0.15% CHAPS, 250 μM [γ$^{32}$P]ATP [1–20 GBq/mmol], purified bovine Rho-kinase [20 ng of protein] or GST-bovine Rho-kinase, and indicated amounts of myosin light chain or myosin) with or without 1 μM GTPγS•GST-RhoA. The kinase reaction for myosin light chain kinase was carried out in 50 μl of reaction mixture (50 mM Tris/HCl at pH 7.5, 1 mM MgCl$_2$, 85 mM KCl, 500 μM [γ-$^{32}$P]ATP [0.5–5 GBq/mmol], purified myosin light chain kinase [50 ng of protein], and indicated amounts of myosin light chain or myosin) with or without 0.1 mM CaCl$_2$ and 10 μg/ml calmodulin. After incubation for 10 min at 30° C., the reaction mixtures were boiled in SDS-sample buffer and subjected to SDS-PAGE as described previously (Laemmli, U. K., Nature, 227, 680–685 (1970)). The radiolabeled bands were visualized by an image analyzer (Fuji).

Figure 17:
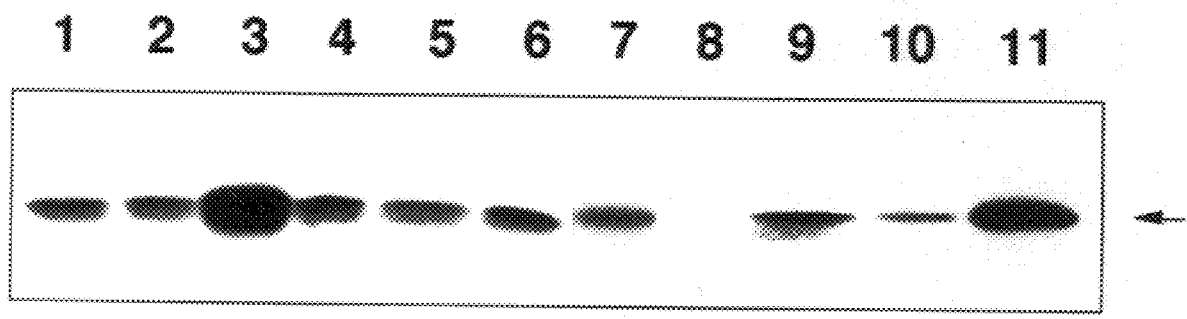
FIG. 17 is an electrophoretic photograph showing phosphorylation of myosin light chain by bovine Rho-kinase. Isolated myosin light chain (0.5 μg of protein) was phosphorylated by purified bovine Rho-kinase (20 ng of protein) in the presence of either GST (lane 1), GDP•GST-RhoA (lane 2), GTPγS•GST-RhoA (lane 3), GTPγS•GST-RhoA$^{Ala37}$ (lane 4), GDP•GST-Rac1 (lane 5) or GTPγS•GST-Rac1 (lane 6), or by GST-bovine Rho-kinase (5 ng of protein) (lane 7), or by myosin light chain kinase in the absence (lane 8) or presence (lane 9) of Ca$^{2+}$ and calmodulin. Intact myosin (5 μg of protein) was phosphorylated in the absence (lane 10) or presence (lane 11) of GTPγS•GST-RhoA. The phosphorylated myosin light chain was resolved by SDS-PAGE and visualized by an image analyzer. The results are representative of three independent experiments.

We found that bovine Rho-kinase phosphorylated myosin light chain (FIG. 17). GTPγS•GST-RhoA enhanced the phosphorylation of myosin light chain by purified bovine Rho-kinase, but GDP•GST-RhoA or GTPγS•GST-RhoA$^{Ala37}$ did not (FIG. 17). RhoA$^{Ala37}$ is structurally equivalent to Ras$^{Ala35}$, which contains an amino acid substitution in the effector domain and, therefore, fails to interact with its target (Satoh, T. et al., J. Biol. Chem., 267, 24149–24152 (1992); McCormick, F., Curr. Opin. Genet. Dev., 4, 71–76 (1994)). GTPγS•GST-Rac1 had no effect either. Structurally activated recombinant bovine Rho-kinase (GST-bovine Rho-kinase) phosphorylated myosin light chain. Under similar conditions, myosin light chain kinase phosphorylated myosin light chain in a Ca$^{2+}$-calmodulin-dependent manner (FIG. 17). We also found that bovine Rho-kinase phosphorylated the myosin light chain of intact myosin in a GTPγS•GST-RhoA-dependent manner (FIG. 17).

A maximum of about 1 mol of phosphate was incorporated into 1 mol of isolated myosin light chain or myosin light chain of intact myosin by purified bovine Rho-kinase or GST-bovine Rho-kinase in the presence of GTPγS•GST-RhoA (data not shown). It is noted that a limited number of kinases such as myosin light chain kinase and protein kinase C are known to phosphorylate intact myosin stoichiometrically (Tan, J. L. et al., Annu. Rev. Biochem., 61, 721–759 (1992)).

Figure 18:
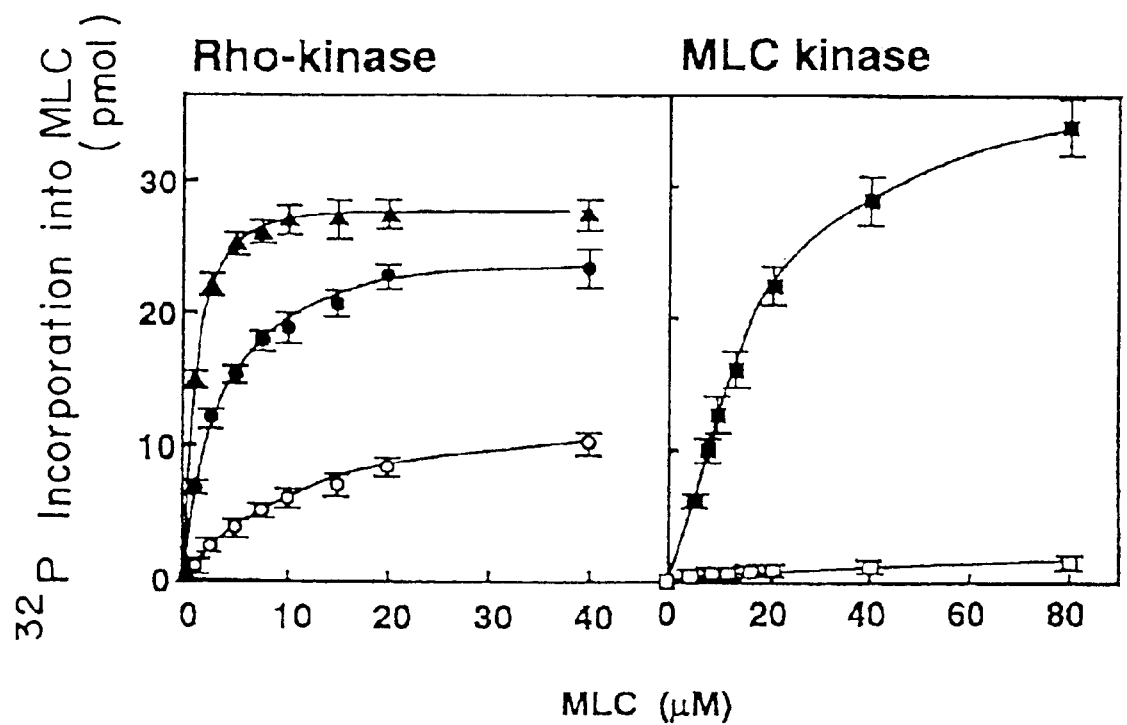
FIG. 18 shows phosphorylation of various amounts of myosin light chain by bovine Rho-kinase. Symbols hereafter indicate the following: MLC: myosin light chain, MLC kinase: myosin light chain kinase. In the left figure, myosin light chain was phosphorylated by Rho-kinase in the presence (closed circle) or absence (open circle) of GTPγS•GST-RhoA, or by GST-Rho-kinase (closed triangle). In the right figure, myosin light chain was phosphorylated by myosin light chain kinase in the presence (closed square) or absence (open square) of Ca$^{2+}$ and calmodulin.

The apparent affinity of isolated myosin light chain for purified bovine Rho-kinase was estimated by measuring the phosphorylation of various concentrations of myosin light chain (FIG. 18). The apparent Km values for myosin light chain in the presence and absence of GTPγS•GST-RhoA were 2.6+0.4 and 12.6+1.6 μM, and the molecular activities were 0.26±0.03 and 0.15±0.02 sec$^{-1}$, respectively. Thus, it is likely that GTPγS•GST-RhoA enhances (increases) the affinity of bovine Rho-kinase for myosin light chain and produces the maximum rate of phosphorylation reaction. The apparent Km value and molecular activity of GST-bovine Rho-kinase were 0.91±0.07 μM and 0.67±0.09 sec$^{-1}$, respectively. The apparent Km value and molecular activity of myosin light chain kinase for myosin light chain were 52.1±7.1 μM and 2.0+0.36 sec$^{-1}$, respectively, under the experimental conditions. The Km value of bovine Rho-kinase for myosin light chain was lower than that of myosin light chain kinase, indicating that bovine Rho-kinase phosphorylates myosin at lower concentrations but has a lower molecular activity than myosin light chain kinase. The lower molecular activity of purified bovine Rho-kinase than that of GST-bovine Rho-kinase is attributed to the fact that the purified bovine Rho-kinase was inactivated during its purification (not shown).

Example 8 Determination of Site of Phosphorylation by Bovine Rho-Kinase on Myosin Light Chain Myosin light chain is phosphorylated primarily at Ser-19 and secondarily at Thr-18 by myosin light chain kinase (Ikebe, M. & Hartshorne, D. J., J. Biol. Chem., 260, 10027–10031 (1985)). The phosphorylation of Ser-19 is essential for the activation of myosin ATPase by actin (Kamisoyama, H. et al., Biochemistry, 33, 840–847 (1994); Bresnick, A. R. et al., Biochemistry, 34, 12576–12583 (1995)). Myosin light chain is phosphorylated at Ser-1, Ser-2 and Thr-9 by protein kinase C, and this phosphorylation by protein kinase C inhibits actin activation by myosin ATPase (Nishikawa, M. et al., J. Biol. Chem., 259, 8808–8814 (1984); Bengur, A. R. et al., J. Biol. Chem., 262, 7613–7617 (1987); Ikebe, M. & Reardon, S., Biochemistry, 29, 2713–2720 (1990)).

Figure 19:
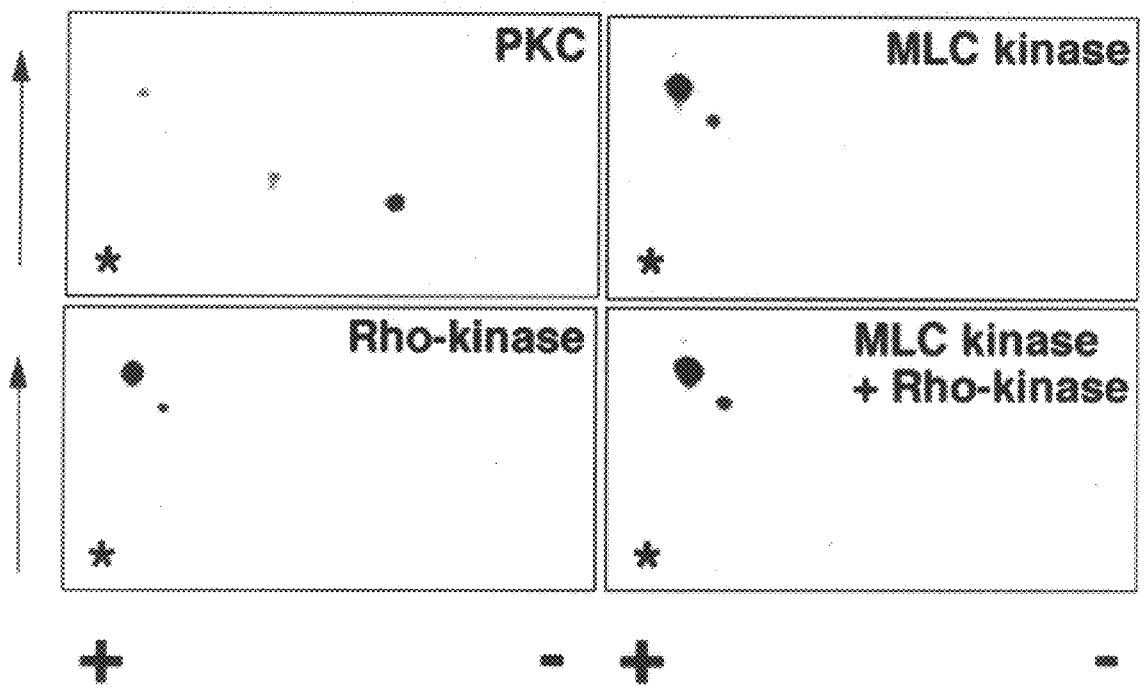
FIG. 19 is an electrophoretic photograph showing the phosphopeptide mapping analysis of myosin light chain. Myosin light chain (0.5 μg of protein) was phosphorylated by Rho-kinase, myosin light chain kinase (MLC kinase), or protein kinase C (PKC). The phosphorylated myosin light chain was digested with trypsin, and each sample was loaded onto a silica gel plate. Phosphopeptides were separated by electrophoresis (horizontal dimension) and chromatography (vertical dimension), and were visualized by an image analyzer. Asterisks indicate origins.

To determine the primary site of phosphorylation by bovine Rho-kinase on myosin light chain, we performed peptide mapping of myosin light chain phosphorylated in vitro by either bovine Rho-kinase, myosin light chain kinase, or protein kinase C according to a previously described method (Naka, M. et al., Nature, 306, 490–492 (1983)). The pattern of two-dimensional peptide mapping of myosin light chain that was phosphorylated by bovine Rho-kinase was identical to that produced by myosin light chain kinase, and different from that produced by protein kinase C (FIG. 19).

A phosphoamino acid analysis according to a previously described method (Hunter, T. & Sefton, B. M., Proc. Natl. Acad. Sci. USA, 77, 1311–1315 (1980)) revealed that phosphorylation by bovine Rho-kinase occurred mainly on the serine residue and partially on the threonine residue of myosin light chain and that phosphorylation by myosin light chain kinase occurred only on the serine residue (Ser-19) of myosin light chain (data not shown). It may be noted that myosin light chain kinase preferentially phosphorylates myosin light chain at Ser-19 under the experimental conditions. The result was consistent when GST-bovine Rho-kinase was used instead of purified bovine Rho-kinase.

GST proteins were fused with wild type myosin light chain and with myosin light chain in which Thr-18 and Ser-19 were substituted by alanine residues to examine if bovine Rho-kinase and myosin light chain kinase could phosphorylate these recombinant proteins. Vectors for expressing these recombinant proteins (pGEX-myosin light chain and pGEX-myosin light chain$^{Ala18,Ala19}$) in E. coli were constructed as follows. The 0.55-kbp cDNA fragment encoding myosin light chain from rat brain Quick clone cDNA (Clontech) was amplified by polymerase chain reaction using the primers SEQ ID NOS: 9 and 10 Respectively 5'-AATAGGATCCGATTTAACCGCCACCATGTCG-3' and 5'-ATAAGGATCCTCAGTCATCTTTGTCTTTCGCTC-3'. Substitution of alanine (Ala) residues for threonine-18 and serine-19 was performed by polymerase chain reaction (Higuchi, R., in PCR Technology (Erlich, H. A. ed) pp. 61–70, Stockton Press, New York (1989)). The cDNA fragments were cloned into the BamHI site of pGEX-2T.

Figure 20:
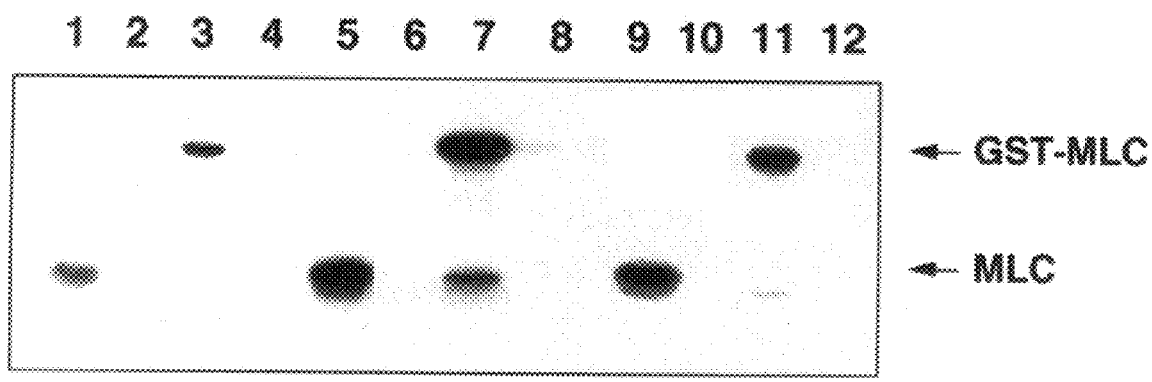
FIG. 20 is an electrophoretic photograph showing the phosphorylation of recombinant myosin light chain. Myosin light chain (MLC), GST, GST-MLC or GST-MLC$^{Ala18,Ala19}$, (2 μM each) was phosphorylated by purified Rho-kinase (20 ng of protein), GST-Rho-kinase (10 ng of protein) or myosin light chain kinase (10 ng of protein) as indicated.
Lanes 1–4: MLC was phosphorylated by purified Rho-kinase.
Lanes 5–8: MLC was phosphorylated by GST-Rho-kinase.
Lanes 9–12: MLC was phosphorylated by MLC kinase.
Lanes 1, 5 and 9: MLC
Lanes 2, 6 and 10: GST
Lanes 3, 7 and 11: GST-MLC
Lanes 4, 8 and 12: GST-MLC$^{Ala18,Ala19}$
The results are representative of three independent experiments.

Both bovine Rho-kinase and myosin light chain kinase phosphorylated GST-myosin light chain but did not phosphorylate GST or GST-myosin light chain$^{Ala18,Ala19}$ (FIG. 20). Protein kinase C phosphorylated both GST-myosin light chain and GST-myosin light chain$^{Ala18,Ala19}$ (data not shown). These results indicate that bovine Rho-kinase phosphorylates myosin light chain mainly at Ser-19, which is the same site phosphorylated by myosin light chain kinase.

Example 9 Actin-Activated MgATPase Assay

To examine whether bovine Rho-kinase functions equivalently to myosin light chain kinase in a cell-free system, we performed an actin-activated MgATPase assay. Purified intact myosin was phosphorylated by GST-bovine Rho-kinase (1 mol phosphorylation per 1 mol myosin), then the activity of actin-activated MgATPase was measured.

Myosin ATPase assay was carried out as described (Ikebe, M. et al., Biochemistry, 23, 5062–5068 (1984)) with minor modifications. Briefly, 0.1 mg/ml myosin was phosphorylated by GST-bovine Rho-kinase (450 ng of protein) in 0.45 ml of reaction mixture (50 mM Tris/HCl at pH 7.5, 2.2 mM EDTA, 1 mM DTT, 6 mM MgCl$_2$, 1 mM EGTA, 85 mM KCl, 1 μM GTPγS·GST-RhoA, and 500 μM ATP [80–200 MBq/mmol]) for 20 min at 30° C. Also, 0.1 mg/ml myosin was phosphorylated by myosin light chain kinase (450 ng of protein) under the same conditions except that 0.1 mM CaCl$_2$ and 10 μg/ml calmodulin were added. The myosin ATPase reaction was carried out in 0.45 ml of ATPase buffer (0.05mg/ml phosphorylated myosin, 50 mM Tris/HCl at pH 7.5, 0.5 mM DTT, 10 mM MgCl$_2$, 0.5 mM EGTA, 85 mM KCl, and 1 mM ATP [80–200 MBq/mmol]) with or without 1 mg/ml F-actin for 30 min at 30° C. An aliquot (80 μl) of the reaction mixture was transferred into the stop solution (1.3% charcoal, 0.12 M NaH$_2$PO$_4$ and 0.33 M perchloric acid) at the indicated time and filtrated. Inorganic phosphate that was liberated from [γ-$^{32}$P]ATP was assessed by a scintillation counter. F-actin was purified from the rabbit skeletal muscle (Spudich, J. A. & Watt, S., J. Biol. Chem., 246, 4866–4871 (1971)). [γ-$^{32}$P]ATP was purchased from Amersham Corp.

Figure 21:
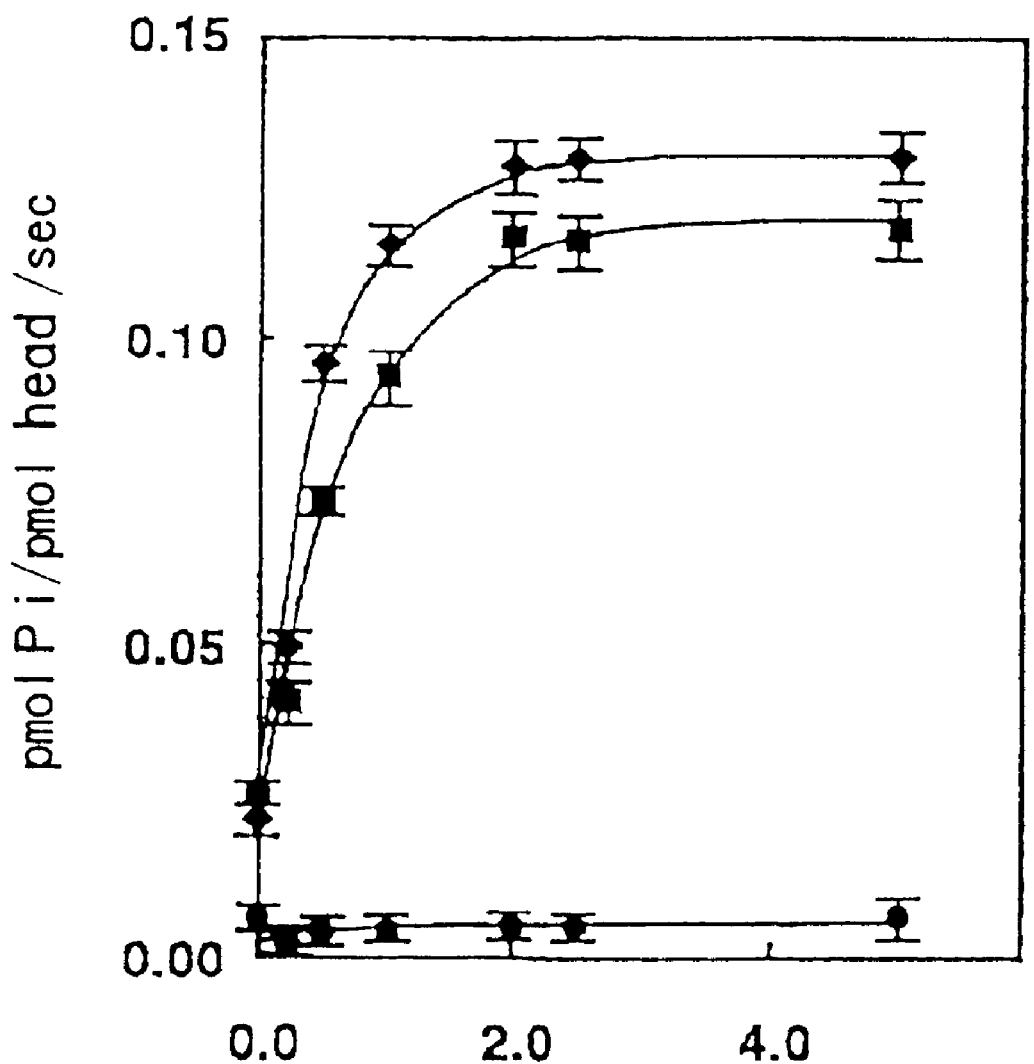
FIG. 21 shows effects of myosin phosphorylation by bovine Rho-kinase on MgATPase activity that was stimulated by actin. The vertical axis denotes phosphorylation rate of myosin head. Myosin was incubated with GST-Rho-kinase (closed square), with myosin light chain kinase (closed rhombus), or without kinase (closed circle). After incubation, the ATPase activity was measured in the presence of F-actin of various concentrations. The values shown are means ± S.E. of triplicates.

The MgATPase activity of myosin increased as it was phosphorylated by GST-Rho-kinase in an F-actin-dependent manner to the extent similar to that increased by myosin light chain kinase (FIG. 21). The apparent K$_a$ value for actin and the molecular activity of phosphorylated myosin were 0.56±0.05 μM and 0.18±0.02 sec$^{-1}$, respectively. These values were similar to those of myosin phosphorylated by myosin light chain kinase. In the experiment, GST-Rho-kinase was used instead of purified natural Rho-kinase because purified natural Rho-kinase does not stoichiometrically phosphorylate myosin under the experimental condition, where high myosin concentration was necessary for the measurement of myosin ATPase activity.

Example 10 Human Rho-Kinase cDNA Cloning

With 0.5 μg of human brain mRNA (CLONTECH) as a template, 1st strand DNA was prepared using SuperScript™ Preamplification System (BRL). With ½₀ volume of this reaction mixture as a template for PCR, cDNA fragment encoding human Rho-kinase (the base sequence 1151–2476 in SEQ ID NO.4) was obtained by PCR, using TAKARA LA PCR kit and the primers SEQ ID NOS 11 & 12 Respectively (5'-CAT TTT CAT TTC TAG GAG ATG ATT ATT CTC TTG CTT TAA C-3', 5'-AAA AAG CAC TTC TTC AGC ACA AAA ATG CAG AAT ATC AGC G-3') produced from the base sequence of bovine Rho-kinase cDNA. A human brain λgt10 cDNA library (1.0×106 plaques) was screened with the prepared cDNA fragment used as a probe, according to J. Sambrook et al., Molecular Cloning: A Laboratory Manual: Cold Spring Habor Laboratory, Cold Spring Harbor, N.Y. (1989). Comparison with the base sequence of bovine Rho-kinase gene revealed that the two obtained clones, p164-20 (the base sequence 938–3710 of SEQ ID NO. 5) and C-9 (the base sequence 2898–4365 of SEQ ID NO. 5), covered the about 2 kbp translated region on the C-terminal. In order to clone the remaining about 1 kbp region on the N-terminal, the human brain λgt10 cDNA library (1.0×106) was screened with the p164-20 clone used as a probe. The result showed that one clone, N6, covered the 1 kbp (approx.) region on the N-terminal (the base sequence 1–929 in SEQ ID NO. 5), including an initiation codon. In order to obtain cDNA fragment that covers the region between p164-20 and N6, the cDNA fragment corresponding to the base sequence 734–1145 was amplified by PCR with Human Brain QUICK-Clone™ cDNA (CLONTECH) as a template, using TAKARA LA PCR kit (Takara Shuzo) and the primers SEQ ID NOS 13 & 14 Respectively 5'-CCT TTG TCA TCT TCA ATG TCA TCG AAA TTG-3' and 5'-CGT GTA TGA AGA TGG ATG AAA CAG GCA TGG-3'. These four clones, covering the translated region of human Rho-kinase gene, were subcloned into Stratagene pBluescriptII SK(-) (M. A. Alting-Mees and J. M. Short, Nucleic Acids Res., 17, 9494 (1989)). Deletion mutants were prepared by using double-stranded Nested Deletion Kit (Pharmacia), and sequenced by using 377 DNA sequencer (ABI). The human brain λgt10 cDNA library was purchased from CLONTECH.

The base sequence of human Rho-kinase cDNA and its deduced amino acid sequence are shown in SEQ ID NO.5 and NO.4, respectively. The predicted protein of human Rho-kinase contains 1388 amino acids with a calculated molecular mass of about 161 kDa. The amino acid sequence of human Rho-kinase (SEQ ID NO.4) was highly homologous to those of bovine Rho-kinase (SEQ ID NO.1) and rat ROKα. (Although the amino acid sequence of rat ROKα reported in Leung, T. et al., J. Biol. Chem., 270, 29051–29054 (1995)* lacked the 84 amino acids on the N-terminal, the entire amino acid sequence was later recorded in the database (EMBL Data Bank accession number U38481). The amino acid residue numbers on rat ROKα hereafter indicate the number according to the sequence recorded in the database.) The amino acids contained in the entire human Rho-kinase were homologous to bovine Rho-kinase and rat ROKα by 97% and 95%, respectively. The human Rho-kinase had a kinase domain on the N-terminal, a coiled-coil domain containing an Rho-binding domain (example 11) in the middle, and a zinc finger-like motif on the C-terminal. The amino acid sequence in the kinase domain of human Rho-kinase (the amino acid sequence 90–359 of SEQ ID NO.4) had 98% similarity and 97% similarity with those in the corresponding domains of bovine Rho-kinase (the amino acid sequence 90–359 of SEQ ID NO.1) and rat ROKα (the amino acid sequence 88–357), respectively. The amino acid sequence in the coiled-coil domain of human Rho-kinase (the amino acid sequence 438–1124 of SEQ ID NO.4) had 97% similarity and 95% similarity with the corresponding domains of bovine Rho-kinase (the amino acid sequence 438–1124 of SEQ ID NO.1) and rat ROKα (the amino acid sequence 436–1122), respectively. The amino acid sequence in the zinc fingerlike motif of human Rho-kinase (the amino acid sequence 1261–1315 in SEQ ID NO.4) had 100% similarity and 98% similarity with the corresponding domains of bovine Rho-kinase (the amino acid sequence 1261–1315 of SEQ ID NO.1) and rat ROKα (the amino acid sequence 1259–1313), respectively.

Also, the amino acid sequence 669–681 of human Rho-kinase (SEQ ID NO.4) contained an amino acid sequence (KRQLQERFTDLEK) recognized by the anti-Rho-kinase antibody described in example 3 (4), which was identical to the amino acid sequence 669–681 of bovine Rho-kinase (SEQ ID NO.1). This fact implies that human Rho-kinase is recognized by the anti-Rho-kinase antibody (example 3 (4)), which is prepared with the synthetic peptide SEQ ID NO: 3 CKRQLQERFTDLEK used as an antigen. Therefore, we concluded that human Rho-kinase is a human counterpart of bovine Rho-kinase.

The entire amino acid sequence of human Rho-kinase (SEQ ID NO.4) had 67% similarity with that of human p160$^{ROCK}$ (Ishizaki, T. et al., EMBO J., 15, 1885–1893 (1996)*). The kinase domain of human Rho-kinase (the amino acid sequence 90–359 in SEQ ID NO.4) was highly homologous to the kinase domain of human p160$^{ROCK}$ (the amino acid sequence 74–343 in Ishizaki, T. et al., EMBO J., 15, 1885–1893 (1996)*) with 92% similarity. Therefore, we concluded that human Rho-kinase is an isozyme of human p160$^{ROCK}$.

Figure 23:
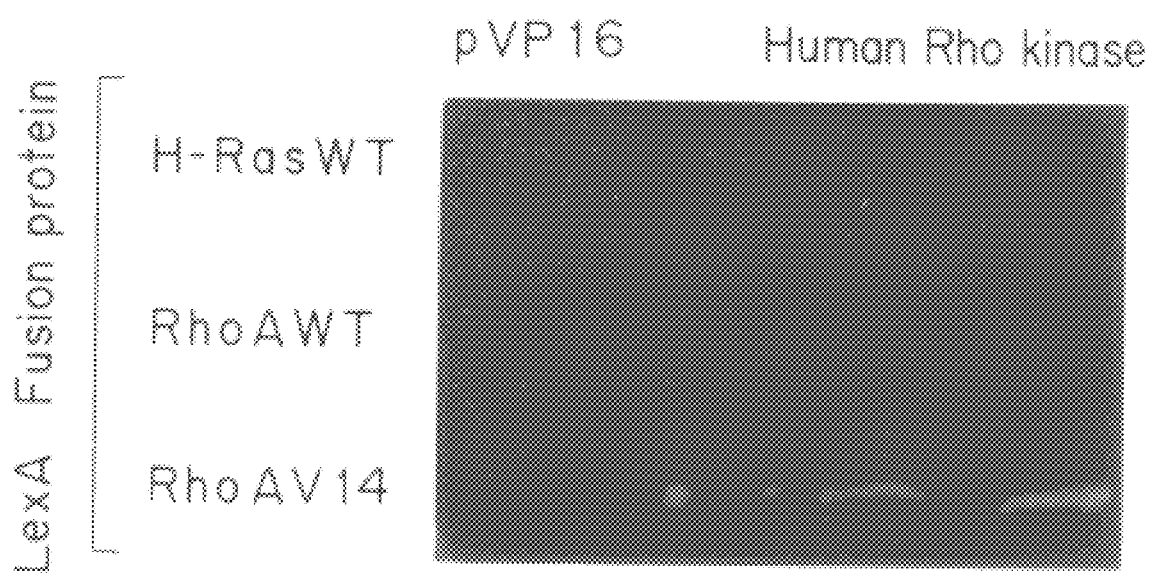
FIG. 23 shows detection of the binding between the Rho protein and human Rho-kinase protein by yeast two hybrid system.

Example 11 Detection of Binding between Human Rho-Kinase and Activated Rho Protein by Two Hybrid System The Rho-binding domain of human Rho-kinase was determined using yeast two hybrid system as follows. The base sequence encoding the amino acid sequence 943–1068 of human Rho-kinase was amplified by PCR using primers SEQ ID NOS 15 & 16 Respectively (5'-TTG CGG CCG CTA AAG ATC ATG AAA GAG CTG GAG ATC-3', 5'-TAG CGG CCG CAA CAT ATG TAG CTT TCT ATT CTC-3'), and inserted in the NotI site of pVP16, to prepare a vector expressing Rho-kinase-VP16-fusion protein (Vojtek, A. B. et al., Cell, 74, 205–214 (1993)). Then, yeast (*S. cerevisiae*) L40 strains (Mat a trp1 leu2 his3 ade2 LYS2::(LexAop)4-HIS3 URA3:: (LexAop)8-LacZ) expressing fusion proteins (LexA-wild H-Ras, LexA-wild Rho, LexA-activated Rho, and LexA-wild H-Ras v.s. Rho-kinase-VP16; LexA-wild Rho v.s. Rho-kinase-VP16; and LexA-activated Rho v.s. Rho-kinase-VP16) were produced by LiCl method (Ito, H. et al., J. Bacteriol., 153, 163–168 (1983)), and cultured in a selective medium (Leu-, Trp-, His-, 200 mM 3AT) to examine their histidine auxotrophy. Only one strain, expressing the LexA-activated Rho fusion protein and the Rho-kinase-VP16 fusion protein, survived in the selective medium (FIG. 23). This result shows that the amino acid sequence 943–1068 of human Rho-kinase or a partial sequence thereof was the Rho-binding domain.

Comparison of the amino acid sequence in the Rho-binding domain of human Rho-kinase with those in the corresponding domains of rat Rho-kinase and Bovine Rho-kinase revealed that human Rho-kinase (the amino acid sequence 943–1068) had 98% similarity with rat ROKα (the amino acid sequence 941–1066) and 98% similarity with bovine Rho-kinase (the amino acid sequence 943–1068). Also, the Rho-binding domain of human Rho-kinase (the amino acid sequence 943–1068) had 53% similarity with the corresponding domain of human p160$^{ROCK}$ (the amino acid sequence 910–1039).

Example 12 Induction of Permeabilized Smooth Muscle Contraction by GST-Rho-Kinase Induction of permeabilized smooth muscle contraction was examined, by using constitutively activated bovine Rho-kinase (recombinant GST-Rho-kinase, example 7) and a smooth muscle whose cell membrane's permeability to protein was increased by surfactant, according to a previously described method (Kobayashi, S. et al., J. Biol. Chem., 264, 17997–18004 (1989); Gong, M. et al., Proc. Natl. Acad. Sci. USA, 93, 1340–1345 (1996)*). The procedure was as follows:

The portal vein was extracted from a rabbit (Japanese white rabbit, male, 2.5–3.0 kg weight). A smooth muscle specimen 1–2 mm in length and 100–200 μm in width was prepared from the portal vein medium. The specimen was placed in plate wells filled with a solution (123 mM NaCl, 4.7 mM KCl, 15.5 mM NaHCO$_3$, 41.2 mM KH$_2$PO$_4$, 1.2 mM MgCl$_2$, 1.25 mM CaCl$_2$, and 11.5 mM D-glucose), and stretched to 1.2 times its original length. Isometric tension was measured by using a transducer (NEC Sanei 6M82). Solutions were changed by transferring the specimen to an adjacent well. The specimen was first incubated in a relaxing solution (74.1 mM potassium methanesulfonate, 2 mM magnesium methanesulfonate, 4.5 mM MgATP, 10 mM creatine phosphate, and 30 mM PIPES) containing 1 mM EGTA. In order to introduce GST-Rho-kinase into the cells and control the intracellular Ca concentration, the specimen was permeabilized (i.e., cell membranes were made porous) by incubating in Triton X-100 solution (relaxing solution containing 10 mM EGTA mixed with 0.3 μM calmodulin, 1 μM leupeptin, and 1 μM FCCP; pCa 6.5) containing 0.5% Triton X-100 at 25° C. for 20 min. The Ca$^{2+}$ concentration in the relaxing solution containing 10 mM EGTA was controlled by varying the Ca salt and EGTA concentrations in the solution.

In order to eliminate any bias, the experiment was performed in blind test. The preparation of sample solutions and contraction measurement were as follows. Sample solution 1 (50 mM Tris-HCl at pH 7.5, 2 mM EGTA, 1 mM dithiothreitol (DTT), and 10 mM glutathione) not containing GST-Rho-kinase, and sample solution 2 (220 μg/ml GST-Rho-kinase, 50 mM Tris-HCl at pH 7.5, 2 mM EGTA, 1 mM dithiothreitol (DTT), and 10 mM glutathione) containing GST-Rho-kinase were prepared. Contraction measurement was performed by a experimenter different from those who prepared the solution to assure that the experimenter did not know which sample solution contained GST-Rho-kinase. The specific activity of GST-Rho-kinase was 41 mol per minute per 1 mol GST-Rho-kinase using S6 peptide (example 2) as a substrate.

Contraction was measured in Triton X-100 solution containing various amounts of sample solution 1 or 2, or phosphatase inhibitor microcystin-LR (MC-LR) (Wakosha) at a concentration of 10 μM. The permeabilized smooth muscle exhibited maximum contraction when exposed to a solution of pCa 4.5 (Ca$^{2+}$ concentration of $10^{-4.5}$ M). FIGS. 24 and 25 indicate the amounts of sample solutions 1 and 2 as their volumetric percentages of Triton X-100 solution.

The results are shown in FIGS. 24 and 25. The permeabilized specimen was completely relaxed in a Ca$^{2+}$-free 10 mM EGTA relaxing solution of pCa 8 or above (10 mM EGTA relaxing solution with Ca$^{2+}$, concentration of $10^{-8}$ M or less), and contracted slightly and slowly in a solution of pCa 6.5 (Ca$^{2+}$ concentration of $10^{-6.5}$ M). The specimen did not show any change by the addition of sample solution 1 (final concentration: 1%) to this mixture, but further contracted (to about 50% of maximum contraction) by the addition of sample solution 2 (final concentration: 1%). A following addition of microcystin-LR (10 μM) caused near-maximum contraction (FIG. 24). Then, the effect of sample solution 2 was examined in a Ca$^{2+}$-free 10 nm EGTA relaxing solution, i.e., a solution of pCa 8 or above (10 mM EGTA relaxing solution with Ca$^{2+}$ concentration of $10^{-8}$ M or less). The result showed contraction changed with the concentration of sample solution 2 and about 70% of maximum contraction when the concentration of sample solution 2 was 6% (FIG. 25). The contraction induced by solution 2 was reversible; i.e., when the specimen was treated (washed) in Triton X-100 solution not containing sample solution 2, it relaxed (data not shown). These results indicated that activated Rho-kinase in smooth muscle cells induces its contraction and that the muscle contracts with essentially no Ca$^{2+}$

What is claimed is:

1. An isolated protein having activated Rho protein binding activity and protein kinase activity, comprising: (1) the amino acid sequence of SEQ ID NO: 1, or (2) an amino acid sequence modified from SEQ ID NO: 1 by at least addition, substitution or deletion of at least one residue to a sequence chosen from the sequence group consisting of positions 1–89, 360–942, and 1069–1388.

2. An isolated protein according to claim 1, wherein all or part of at least one sequence selected from the sequence group consisting of positions 1–89, 360–942, and 1069–1388 is deleted.

3. A isolated protein according to claim 1, wherein said modified amino acid sequence comprises the amino acid sequence from positions 90–359 and 943–1068.

4. An isolated protein having activated Rho protein binding activity and protein kinase activity comprising: (1) the amino acid sequence of SEQ ID NO: 4, or (2) an amino acid sequence modified from SEQ ID NO. 4 by at least addition, substitution or deletion of at least one residue to a sequence chosen from the sequence group consisting of positions 1–89, 360–942, and 1069–1388.

5. A protein according to claim 4, wherein all or part of at least one sequence selected from the sequence group consisting of positions 1–89, 360–942, and 1069–1388 is deleted.

6. A protein according to claim 4, wherein said modified amino acid sequence comprises the amino acid sequence of positions 90–359 and 943–1068.

7. An isolated protein of SEQ ID NO: 1 or a modification thereof having activated Rho protein binding activity wherein at least one amino acid has been added to amino acid sequence positions 1–942 or 1069–1388, and at least one amino acid has been substituted or deleted from amino acid sequence positions 1–942 or 1069–1388.

8. A protein according to claim 7, that lacks protein kinase activity, and that has at least one addition, insertion, substitution, or deletion within sequence positions 90–359.

9. A protein according to claim 8 having deleted therein sequence positions 90–359 or a portion of this sequence that has protein kinase activity.

10. A protein according to claim 8, wherein said modified amino acid sequence comprises the amino acid sequence positions 421–1137, 438–1124, 799–1137 or 943–106.

11. An isolated protein or derivative thereof comprising a modified amino acid sequence of SEQ ID NO: 4 which has activated Rho protein binding activity wherein SEQ ID NO: 4 has been altered by at least one amino acid modification selected from the group consisting of adding an amino acid to the sequence within positions 1–942, adding an amino acid to the sequence within positions 1069–1388, substituting an amino acid within sequence positions 1–942, substituting an amino acid within sequence positions 1069–1388, deleting an amino acid from sequence positions 1–942, and deleting an amino acid from sequence positions 1069–1388.

12. A protein according to claim 11, wherein said modified amino acid sequence does not have protein kinase activity and has at least one of an addition, an insertion, a substitution, or a deletion in the amino acid sequence positions 90–359 in SEQ ID NO: 4.

13. A protein according to claim 12, wherein the amino acid sequence positions 90–359 in SEQ ID NO: 4 or a region containing a part thereof which has protein kinase activity is deleted.

14. A protein according to claim 12, wherein said modified amino acid sequence comprises the amino acid sequence positions 421–1137, 438–1124, 799–1137 or 943–1068.

15. A protein comprising a modified amino acid sequence of SEQ ID NO: 1 which has protein kinase activity wherein SEQ ID NO. 1 has been altered by at least one amino acid modification selected from the group consisting of adding an amino acid to the sequence within positions 1–89, adding an amino acid to the sequence within positions 360–1388, substituting an amino acid within sequence positions 1–89, substituting an amino acid within sequence positions 360–1388, deleting an amino acid from sequence positions 1–89, and deleting an amino acid from sequence positions 360–1388.

16. A protein according to claim 15, wherein said modified amino acid sequence does not have activated Rho binding activity and has an addition, an insertion, a substitution, and/or a deletion in the amino acid sequence positions 943–1068 in SEQ ID NO: 1.

17. A protein according to claim 16, wherein the amino acid sequence positions 943–1068 in SEQ ID NO: 1 or a region containing a part thereof which has protein kinase activity is deleted.

18. A protein according to claim 16, wherein said modified amino acid sequence comprises the amino acid sequence positions 90–359 or 6553 in SEQ ID NO: 1.

19. An isolated protein comprising a modified amino acid sequence of SEQ ID NO: 4 which has protein kinase activity wherein one or more amino acids are added into the amino acid sequence positions 1–89 and/or 360–1388 in SEQ ID NO: 4, and/or one or more amino acids in the amino acid sequence positions 1–89 and/or 360–1388 in SEQ ID NO: 4 are substituted and/or deleted.

20. A protein according to claim 19, wherein said modified amino acid sequence does not have activated Rho binding activity and has at least one selected from the group consisting of an addition, an insertion, a substitution, and a deletion in the amino acid sequence positions 943–1068 in SEQ ID NO: 4.

21. A protein according to claim 20, wherein the amino acid sequence positions 943–1068 in SEQ ID NO: 4 or a region containing a part thereof which has protein kinase activity is deleted.

22. A protein according to claim 20, wherein said modified amino acid sequence comprises the amino acid sequence positions 90–359 or 6553 in SEQ ID NO: 4.

23. A method for screening a material inhibiting binding between activated Rho protein and a protein according to claim 1, 4, 7, or 11 comprising; (1) placing a material to be screened in a screening system containing said activated Rho protein and said protein, and (2) measuring the degree of inhibition of binding between said activated Rho protein and said protein.

24. A screening method according to claim 23, wherein the screening system is a cell system.

25. A screening method according to claim 23, wherein the screening system is a yeast two hybrid system.

26. A screening method according to claim 23, which is a method for screening tumorigenesis or metastasis suppressors.

27. A screening method according to claim 23, which is a method for screening smooth muscle contraction suppressors.

28. A method for screening a material inhibiting protein kinase activity of a protein according to claim 1, 4, 15 or 19, comprising: (1) placing the material in a screening system containing said protein, and (2) measuring degree of inhibition of the protein kinase activity of said protein.

29. A screening method according to claim 28, wherein the screening system is a cell system.

30. A screening method according to claim 28, which is a method for screening tumorigenesis or metastasis suppressors.

31. A screening method according to claim 28, which is a method for screening smooth muscle contraction suppressors.

32. A method for screening a material inhibiting protein kinase activity of a protein according to claim 1, 4, 15 or 19, comprising: (1) placing the material in a screening system containing activated Rho protein and said protein, and (2) measuring the degree of inhibition of the protein kinase activity of said protein.

33. A screening method according to claim 32, wherein said activated Rho protein placed in the screening system is a posttranslationally controlled protein.

34. A screening method according to claim 32, wherein the degree of the inhibition of the protein kinase activity is measured by using a substrate selected from the group consisting of myelin basic protein, S6 peptide, α PKC, vinculin, talin, metavinculin, caldesmon, filamin, vimentin, α-actinin, MAP-4, myosin light chain, myosin light chain phosphatase, and myosin binding subunit of myosin light chain phosphatase.

35. A screening method according to claim 32, wherein the screening system is a cell system.

36. A screening method according to claim 32, which is a method for screening tumorigenesis or metastasis suppressors.

37. A screening method according to claim 32, which is a method for screening smooth muscle contraction suppressors.

38. A method for screening a material inhibiting enhancement of protein kinase activity of a protein according to claim 1, 4, 15, or 19, comprising: (1) placing a material to be screened in a screening system containing activated Rho protein and said protein, and (2) measuring the degree of inhibition of the protein kinase activity enhancement of said protein.

39. A screening method according to claim 38, wherein said activated Rho protein placed in the screening system is a posttranslationally controlled protein.

40. A screening method according to claim 38, wherein the degree of the inhibition the enhancement of the protein kinase activity is measured by using a substrate selected from the group consisting of myelin basic protein, S6 peptide, α PKC, vinculin, talin, metavinculin, caldesmon, filamin, vimentin, α-actinin, MAP-4, myosin light chain, myosin light chain phosphatase, and myosin binding subunit of myosin light chain phosphatase.

41. A screening method according to claim 38, wherein the screening system is a cell system.

42. A screening method according to claim 38, which is a method for screening tumorigenesis or metastasis suppressors.

43. A screening method according to claim 38, which is a method for screening smooth muscle contraction suppressors.

44. A protein according to claim 1 which is recognized by an antibody against a peptide of SEQ ID NO: 3.

45. A composition for suppressing smooth muscle contraction comprising a protein according to claim 8 or 12.

46. A pharmaceutical composition for treating a circulatory system disease comprising a protein according to claim 8 or 12.

47. A pharmaceutical composition according to claim 46, wherein the circulatory system disease is selected from the group consisting of hypertension, vasospasm (cardiovascular vasospasm and cerebrovascular vasospasm), cardiac angina, myocardial infarction, and arteriosclerosis obliterans.

48. A method for treating a circulatory system disease comprising administrating an effective amount of a protein according to claim 8 or 12.

49. A method according to claim 48, wherein the circulatory system disease is selected from the group consisting of hypertension, vasospasm, cardiac angina, myocardial infarction, and arteriosclerosis obliterans.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 1388 amino acids
        (B) TYPE: amino acid
        (D) TOPOLOGY: linear (ii) MOLECULE TYPE: protein (xi) SEQUENCE DESCRIPTION: SEQ ID NO:1:

```
Met Ser Arg Pro Pro Pro Thr Gly Lys Met Pro Gly Ala Pro Glu Ala
 1               5                  10                  15

Val Ser Gly Asp Gly Ala Gly Ala Ser Arg Gln Arg Lys Leu Glu Ala
                20                  25                  30

Leu Ile Arg Asp Pro Arg Ser Pro Ile Asn Val Glu Ser Leu Leu Asp
            35                  40                  45

Gly Leu Asn Pro Leu Val Leu Asp Leu Asp Phe Pro Ala Leu Arg Lys
    50                  55                  60

Asn Lys Asn Ile Asp Asn Phe Leu Asn Arg Tyr Glu Lys Ile Val Lys
65                  70                  75                  80

Lys Ile Arg Gly Leu Gln Met Lys Ala Glu Asp Tyr Asp Val Val Lys
```

-continued

```
                    85                  90                  95
Val Ile Gly Arg Gly Ala Phe Gly Glu Val Gln Leu Val Arg His Lys
            100                 105                 110
Ala Ser Gln Lys Val Tyr Ala Met Lys Leu Leu Ser Lys Phe Glu Met
            115                 120                 125
Ile Lys Arg Ser Asp Ser Ala Phe Phe Trp Glu Glu Arg Asp Ile Met
            130                 135                 140
Ala Phe Ala Asn Ser Pro Trp Val Val Gln Leu Phe Cys Ala Phe Gln
145                 150                 155                 160
Asp Asp Lys Tyr Leu Tyr Met Val Met Glu Tyr Met Pro Gly Gly Asp
                165                 170                 175
Leu Val Asn Leu Met Ser Asn Tyr Asp Val Pro Glu Lys Trp Ala Lys
                180                 185                 190
Phe Tyr Thr Ala Glu Val Val Leu Ala Leu Asp Ala Ile His Ser Met
                195                 200                 205
Gly Leu Ile His Arg Asp Val Lys Pro Asp Asn Met Leu Leu Asp Lys
            210                 215                 220
His Gly His Leu Lys Leu Ala Asp Phe Gly Thr Cys Met Lys Met Asp
225                 230                 235                 240
Glu Thr Gly Met Val His Cys Asp Thr Ala Val Gly Thr Pro Asp Tyr
                245                 250                 255
Ile Ser Pro Glu Val Leu Lys Ser Gln Gly Gly Asp Gly Tyr Tyr Gly
                260                 265                 270
Arg Glu Cys Asp Trp Trp Ser Val Gly Val Phe Leu Phe Glu Met Leu
            275                 280                 285
Val Gly Asp Thr Pro Phe Tyr Ala Asp Ser Leu Val Gly Thr Tyr Ser
            290                 295                 300
Lys Ile Met Asp His Lys Asn Ser Leu Cys Phe Pro Glu Asp Ala Glu
305                 310                 315                 320
Ile Ser Lys His Ala Lys Asn Leu Ile Cys Ala Phe Leu Thr Asp Arg
                325                 330                 335
Glu Val Arg Leu Gly Arg Asn Gly Val Glu Glu Ile Lys Gln His Pro
            340                 345                 350
Phe Phe Lys Asn Asp Gln Trp Asn Trp Asp Asn Ile Arg Glu Thr Ala
            355                 360                 365
Ala Pro Val Val Pro Glu Leu Ser Ser Asp Ile Asp Ser Ser Asn Phe
370                 375                 380
Asp Asp Ile Glu Asp Asp Lys Gly Asp Val Glu Thr Phe Pro Ile Pro
385                 390                 395                 400
Lys Ala Phe Val Gly Asn Gln Leu Pro Phe Ile Gly Phe Thr Tyr Tyr
                405                 410                 415
Arg Glu Asn Leu Leu Leu Ser Asp Ser Pro Ser Cys Lys Glu Asn Asp
            420                 425                 430
Ser Ile Gln Ser Arg Lys Asn Glu Glu Ser Gln Glu Ile Gln Lys Lys
            435                 440                 445
Leu Tyr Thr Leu Glu Glu His Leu Ser Thr Glu Ile Gln Ala Lys Glu
            450                 455                 460
Glu Leu Glu Gln Lys Cys Lys Ser Val Asn Thr Arg Leu Glu Lys Val
465                 470                 475                 480
Ala Lys Glu Leu Glu Glu Glu Ile Thr Leu Arg Lys Asn Val Glu Ser
                485                 490                 495
Thr Leu Arg Gln Leu Glu Arg Glu Lys Ala Leu Leu Gln His Lys Asn
            500                 505                 510
```

```
Ala Glu Tyr Gln Arg Lys Ala Asp His Glu Ala Asp Lys Lys Arg Asn
        515                 520                 525

Leu Glu Asn Asp Val Asn Ser Leu Lys Asp Gln Leu Glu Asp Leu Lys
        530                 535                 540

Lys Arg Asn Gln Asn Ser Gln Ile Ser Thr Glu Lys Val Asn Gln Leu
545                 550                 555                 560

Gln Arg Gln Leu Asp Glu Thr Asn Ala Leu Leu Arg Thr Glu Ser Asp
                565                 570                 575

Thr Ala Ala Arg Leu Arg Lys Thr Gln Ala Glu Ser Ser Lys Gln Ile
            580                 585                 590

Gln Gln Leu Glu Ser Asn Asn Arg Asp Leu Gln Asp Lys Asn Cys Leu
        595                 600                 605

Leu Glu Thr Ala Lys Leu Lys Leu Glu Lys Glu Phe Ile Asn Leu Gln
        610                 615                 620

Ser Val Leu Glu Ser Glu Arg Arg Asp Arg Thr His Gly Ser Glu Ile
625                 630                 635                 640

Ile Asn Asp Leu Gln Gly Arg Ile Ser Gly Leu Glu Glu Asp Val Lys
                645                 650                 655

Asn Gly Lys Ile Leu Leu Ala Lys Val Glu Leu Glu Lys Arg Gln Leu
            660                 665                 670

Gln Glu Arg Phe Thr Asp Leu Glu Lys Glu Lys Asn Asn Met Glu Ile
        675                 680                 685

Asp Met Thr Tyr Gln Leu Lys Val Ile Gln Gln Ser Leu Glu Gln Glu
        690                 695                 700

Glu Thr Glu His Lys Ala Thr Lys Ala Arg Leu Ala Asp Lys Asn Lys
705                 710                 715                 720

Ile Tyr Glu Ser Ile Glu Ala Lys Ser Ala Met Lys Glu Met
                725                 730                 735

Glu Lys Lys Leu Ser Glu Glu Arg Thr Leu Lys Gln Lys Val Glu Asn
            740                 745                 750

Leu Leu Leu Glu Ala Glu Lys Arg Cys Ser Ile Leu Asp Cys Asp Leu
        755                 760                 765

Lys Gln Ser Gln Gln Lys Ile Asn Glu Leu Leu Lys Gln Lys Asp Val
        770                 775                 780

Leu Asn Glu Asp Val Arg Asn Leu Thr Leu Lys Ile Glu Gln Glu Thr
785                 790                 795                 800

Gln Lys Arg Cys Leu Thr Gln Asn Asp Leu Lys Met Gln Thr Gln Gln
                805                 810                 815

Val Asn Thr Leu Lys Met Ser Glu Lys Gln Leu Lys Gln Glu Asn Asn
            820                 825                 830

His Leu Leu Glu Met Lys Met Ser Leu Glu Lys Gln Asn Ala Glu Leu
        835                 840                 845

Arg Lys Glu Arg Gln Asp Ala Asp Gly Gln Met Lys Glu Leu Gln Asp
850                 855                 860

Gln Leu Glu Ala Glu Gln Tyr Phe Ser Thr Leu Tyr Lys Thr Gln Val
865                 870                 875                 880

Arg Glu Leu Lys Glu Glu Cys Glu Glu Lys Thr Lys Leu Cys Lys Glu
                885                 890                 895

Leu Gln Gln Lys Lys Gln Glu Leu Gln Asp Glu Arg Asp Ser Leu Ala
            900                 905                 910

Ala Gln Leu Glu Ile Thr Leu Thr Lys Ala Asp Ser Glu Gln Leu Ala
        915                 920                 925

Arg Ser Ile Ala Glu Glu Gln Tyr Ser Asp Leu Glu Lys Glu Lys Ile
        930                 935                 940
```

-continued

```
Met Lys Glu Leu Glu Ile Lys Glu Met Met Ala Arg His Lys Gln Glu
945                 950                 955                 960

Leu Thr Glu Lys Asp Ala Thr Ile Ala Ser Leu Glu Glu Thr Asn Arg
            965                 970                 975

Thr Leu Thr Ser Asp Val Ala Asn Leu Ala Asn Glu Lys Glu Glu Leu
            980                 985                 990

Asn Asn Lys Leu Lys Glu Ala Gln Glu Gln Leu Ser Arg Leu Lys Asp
            995                 1000                1005

Glu Glu Ile Ser Ala Ala Ala Ile Lys Ala Gln Phe Glu Lys Gln Leu
            1010                1015                1020

Leu Thr Glu Arg Thr Leu Lys Thr Gln Ala Val Asn Lys Leu Ala Glu
1025                1030                1035                1040

Ile Met Asn Arg Lys Glu Pro Val Lys Arg Gly Asn Asp Thr Asp Val
                1045                1050                1055

Arg Arg Lys Glu Lys Glu Asn Arg Lys Leu His Met Glu Leu Lys Ser
                1060                1065                1070

Glu Arg Glu Lys Leu Thr Gln Gln Met Ile Lys Tyr Gln Lys Glu Leu
                1075                1080                1085

Asn Glu Met Gln Ala Gln Ile Ala Glu Glu Ser Gln Ile Arg Ile Glu
                1090                1095                1100

Leu Gln Met Thr Leu Asp Ser Lys Asp Ser Asp Ile Glu Gln Leu Arg
1105                1110                1115                1120

Ser Gln Leu Gln Ala Leu His Ile Gly Leu Asp Ser Ser Ser Ile Gly
                1125                1130                1135

Ser Gly Pro Gly Asp Thr Glu Ala Asp Asp Gly Phe Pro Glu Ser Arg
                1140                1145                1150

Leu Glu Gly Trp Leu Ser Leu Pro Val Arg Asn Asn Thr Lys Lys Phe
                1155                1160                1165

Gly Trp Val Lys Lys Tyr Val Ile Val Ser Ser Lys Lys Ile Leu Phe
                1170                1175                1180

Tyr Asp Ser Glu Gln Asp Lys Glu Gln Ser Asn Pro Tyr Met Val Leu
1185                1190                1195                1200

Asp Ile Asp Lys Leu Phe His Val Arg Pro Val Thr Gln Thr Asp Val
                1205                1210                1215

Tyr Arg Ala Asp Ala Lys Glu Ile Pro Arg Ile Phe Gln Ile Leu Tyr
                1220                1225                1230

Ala Asn Glu Gly Glu Ser Lys Lys Glu Gln Glu Phe Pro Val Glu Pro
                1235                1240                1245

Val Gly Glu Lys Ser Asn Tyr Ile Cys His Lys Gly His Glu Phe Ile
                1250                1255                1260

Pro Thr Leu Tyr His Phe Pro Thr Asn Cys Glu Ala Cys Met Lys Pro
1265                1270                1275                1280

Leu Trp His Met Phe Lys Pro Pro Ala Leu Glu Cys Arg Arg Cys
                1285                1290                1295

His Ile Lys Cys His Lys Asp His Met Asp Lys Lys Glu Glu Ile Ile
                1300                1305                1310

Ala Pro Cys Lys Val Tyr Tyr Asp Ile Ser Ser Ala Lys Asn Leu Leu
                1315                1320                1325

Leu Leu Ala Asn Ser Thr Glu Glu Gln Gln Lys Trp Val Ser Arg Leu
                1330                1335                1340

Val Lys Lys Ile Pro Lys Lys Pro Pro Ala Pro Asp Pro Phe Ala Arg
1345                1350                1355                1360

Ser Ser Pro Arg Thr Ser Met Lys Ile Gln Gln Asn Gln Ser Ile Arg
```

```
                              1365               1370                1375
Arg Pro Ser Arg Gln Leu Ala Pro Asn Lys Pro Ser
              1380                 1385

(2) INFORMATION FOR SEQ ID NO:2:

(i) SEQUENCE CHARACTERISTICS:
        (A) LENGTH: 5053 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Bovine (ix) FEATURE:
        (A) NAME/KEY: CDS
        (B) LOCATION: 1..4164

(xi) SEQUENCE DESCRIPTION: SEQ ID NO:2:

ATG AGC CGG CCC CCG CCG ACG GGG AAG ATG CCC GGC GCC CCC GAG GCC        48
Met Ser Arg Pro Pro Pro Thr Gly Lys Met Pro Gly Ala Pro Glu Ala
 1               5                  10                  15

GTG TCG GGG GAC GGC GCG GGC GCG AGC CGC CAG AGG AAG CTG GAA GCG        96
Val Ser Gly Asp Gly Ala Gly Ala Ser Arg Gln Arg Lys Leu Glu Ala
             20                  25                  30

CTG ATC CGA GAC CCT CGT TCG CCC ATC AAC GTG GAG AGC TTG CTG GAT       144
Leu Ile Arg Asp Pro Arg Ser Pro Ile Asn Val Glu Ser Leu Leu Asp
         35                  40                  45

GGC TTA AAT CCT TTG GTC CTT GAT TTG GAT TTT CCT GCT TTG AGG AAA       192
Gly Leu Asn Pro Leu Val Leu Asp Leu Asp Phe Pro Ala Leu Arg Lys
 50                  55                  60

AAC AAA AAT ATA GAT AAT TTC TTA AAT AGA TAT GAG AAA ATT GTG AAA       240
Asn Lys Asn Ile Asp Asn Phe Leu Asn Arg Tyr Glu Lys Ile Val Lys
 65                  70                  75                  80

AAA ATT AGA GGT TTA CAG ATG AAG GCA GAA GAC TAC GAT GTT GTA AAA       288
Lys Ile Arg Gly Leu Gln Met Lys Ala Glu Asp Tyr Asp Val Val Lys
             85                  90                  95

GTT ATC GGA AGA GGT GCT TTT GGT GAA GTC CAG TTG GTT CGT CAT AAG       336
Val Ile Gly Arg Gly Ala Phe Gly Glu Val Gln Leu Val Arg His Lys
            100                 105                 110

GCA TCA CAG AAA GTT TAT GCT ATG AAG CTT CTT AGT AAG TTT GAA ATG       384
Ala Ser Gln Lys Val Tyr Ala Met Lys Leu Leu Ser Lys Phe Glu Met
        115                 120                 125

ATA AAA AGA TCA GAT TCT GCT TTT TTC TGG GAG GAA AGA GAT ATT ATG       432
Ile Lys Arg Ser Asp Ser Ala Phe Phe Trp Glu Glu Arg Asp Ile Met
    130                 135                 140

GCC TTT GCC AAC AGT CCC TGG GTG GTT CAG CTC TTT TGT GCC TTT CAA       480
Ala Phe Ala Asn Ser Pro Trp Val Val Gln Leu Phe Cys Ala Phe Gln
145                 150                 155                 160

GAT GAT AAG TAT CTG TAC ATG GTA ATG GAG TAC ATG CCT GGT GGA GAC       528
Asp Asp Lys Tyr Leu Tyr Met Val Met Glu Tyr Met Pro Gly Gly Asp
                165                 170                 175

CTT GTA AAC CTT ATG AGT AAC TAT GAT GTA CCT GAA AAA TGG GCC AAA       576
Leu Val Asn Leu Met Ser Asn Tyr Asp Val Pro Glu Lys Trp Ala Lys
            180                 185                 190

TTT TAT ACT GCT GAA GTT GTT CTT GCT TTG GAT GCC ATA CAC TCC ATG       624
Phe Tyr Thr Ala Glu Val Val Leu Ala Leu Asp Ala Ile His Ser Met
        195                 200                 205

GGT TTA ATT CAC AGA GAT GTG AAG CCT GAC AAC ATG CTC TTG GAT AAA       672
Gly Leu Ile His Arg Asp Val Lys Pro Asp Asn Met Leu Leu Asp Lys
    210                 215                 220
```

```
CAT GGG CAT CTA AAA TTA GCA GAT TTT GGC ACA TGT ATG AAG ATG GAT        720
His Gly His Leu Lys Leu Ala Asp Phe Gly Thr Cys Met Lys Met Asp
225                 230                 235                 240

GAA ACA GGC ATG GTG CAT TGT GAT ACA GCA GTT GGA ACA CCC GAT TAT        768
Glu Thr Gly Met Val His Cys Asp Thr Ala Val Gly Thr Pro Asp Tyr
                245                 250                 255

ATA TCA CCC GAG GTC CTG AAA TCA CAA GGG GGT GAT GGT TAC TAT GGG        816
Ile Ser Pro Glu Val Leu Lys Ser Gln Gly Gly Asp Gly Tyr Tyr Gly
            260                 265                 270

CGA GAA TGT GAT TGG TGG TCC GTG GGT GTT TTC CTT TTT GAA ATG CTG        864
Arg Glu Cys Asp Trp Trp Ser Val Gly Val Phe Leu Phe Glu Met Leu
        275                 280                 285

GTG GGG GAT ACT CCA TTT TAT GCA GAT TCA CTT GTA GGA ACA TAT AGC        912
Val Gly Asp Thr Pro Phe Tyr Ala Asp Ser Leu Val Gly Thr Tyr Ser
    290                 295                 300

AAA ATT ATG GAT CAT AAA AAC TCA CTA TGT TTC CCT GAA GAT GCA GAA        960
Lys Ile Met Asp His Lys Asn Ser Leu Cys Phe Pro Glu Asp Ala Glu
305                 310                 315                 320

ATT TCT AAA CAT GCG AAG AAT CTC ATC TGT GCC TTC TTA ACA GAT AGG       1008
Ile Ser Lys His Ala Lys Asn Leu Ile Cys Ala Phe Leu Thr Asp Arg
                325                 330                 335

GAG GTA CGC CTT GGA AGA AAC GGG GTA GAA GAA ATC AAA CAA CAT CCT       1056
Glu Val Arg Leu Gly Arg Asn Gly Val Glu Glu Ile Lys Gln His Pro
                340                 345                 350

TTC TTT AAG AAT GAT CAG TGG AAT TGG GAT AAC ATA AGA GAG ACT GCA       1104
Phe Phe Lys Asn Asp Gln Trp Asn Trp Asp Asn Ile Arg Glu Thr Ala
            355                 360                 365

GCT CCT GTG GTA CCT GAA CTC AGC AGT GAC ATA GAC AGC AGC AAT TTT       1152
Ala Pro Val Val Pro Glu Leu Ser Ser Asp Ile Asp Ser Ser Asn Phe
        370                 375                 380

GAT GAC ATT GAA GAT GAT AAA GGA GAT GTA GAA ACC TTC CCA ATT CCC       1200
Asp Asp Ile Glu Asp Asp Lys Gly Asp Val Glu Thr Phe Pro Ile Pro
385                 390                 395                 400

AAG GCT TTT GTG GGA AAT CAG CTA CCT TTT ATA GGA TTT ACC TAC TAC       1248
Lys Ala Phe Val Gly Asn Gln Leu Pro Phe Ile Gly Phe Thr Tyr Tyr
                405                 410                 415

AGA GAA AAT TTG CTA CTA AGT GAC TCT CCA TCT TGT AAA GAA AAT GAC       1296
Arg Glu Asn Leu Leu Leu Ser Asp Ser Pro Ser Cys Lys Glu Asn Asp
                420                 425                 430

TCA ATT CAA TCA AGG AAG AAT GAA GAG AGT CAA GAG ATT CAG AAA AAA       1344
Ser Ile Gln Ser Arg Lys Asn Glu Glu Ser Gln Glu Ile Gln Lys Lys
            435                 440                 445

CTG TAC ACA TTA GAA GAA CAC CTT AGC ACT GAG ATT CAG GCC AAA GAG       1392
Leu Tyr Thr Leu Glu Glu His Leu Ser Thr Glu Ile Gln Ala Lys Glu
        450                 455                 460

GAA CTA GAA CAG AAG TGC AAG TCT GTT AAT ACT CGC TTA GAG AAA GTG       1440
Glu Leu Glu Gln Lys Cys Lys Ser Val Asn Thr Arg Leu Glu Lys Val
465                 470                 475                 480

GCA AAG GAG TTA GAA GAA GAG ATT ACC TTA AGG AAA AAT GTG GAA TCA       1488
Ala Lys Glu Leu Glu Glu Glu Ile Thr Leu Arg Lys Asn Val Glu Ser
                485                 490                 495

ACA TTA AGA CAA TTA GAA AGA GAA AAA GCA CTT CTT CAG CAC AAA AAT       1536
Thr Leu Arg Gln Leu Glu Arg Glu Lys Ala Leu Leu Gln His Lys Asn
                500                 505                 510

GCA GAA TAT CAG CGG AAA GCT GAT CAT GAA GCA GAC AAG AAG CGA AAT       1584
Ala Glu Tyr Gln Arg Lys Ala Asp His Glu Ala Asp Lys Lys Arg Asn
            515                 520                 525

TTG GAG AAT GAT GTT AAC AGT TTA AAA GAT CAG CTT GAA GAT TTG AAA       1632
Leu Glu Asn Asp Val Asn Ser Leu Lys Asp Gln Leu Glu Asp Leu Lys
        530                 535                 540
```

```
AAA AGA AAT CAG AAC TCT CAG ATA TCC ACT GAG AAA GTG AAT CAA CTC      1680
Lys Arg Asn Gln Asn Ser Gln Ile Ser Thr Glu Lys Val Asn Gln Leu
545                 550                 555                 560

CAG AGA CAA CTG GAT GAA ACC AAT GCT TTG CTG CGA ACA GAA TCT GAT      1728
Gln Arg Gln Leu Asp Glu Thr Asn Ala Leu Leu Arg Thr Glu Ser Asp
                565                 570                 575

ACT GCA GCC CGG TTA AGG AAA ACA CAG GCA GAA AGT TCA AAA CAG ATT      1776
Thr Ala Ala Arg Leu Arg Lys Thr Gln Ala Glu Ser Ser Lys Gln Ile
            580                 585                 590

CAG CAG CTG GAA TCT AAC AAT AGA GAT CTA CAA GAC AAA AAT TGC CTG      1824
Gln Gln Leu Glu Ser Asn Asn Arg Asp Leu Gln Asp Lys Asn Cys Leu
        595                 600                 605

CTG GAG ACT GCC AAG TTA AAA CTT GAA AAG GAA TTT ATC AAT CTT CAG      1872
Leu Glu Thr Ala Lys Leu Lys Leu Glu Lys Glu Phe Ile Asn Leu Gln
    610                 615                 620

TCA GTT CTA GAA TCT GAA AGG AGG GAC CGA ACC CAT GGA TCA GAG ATT      1920
Ser Val Leu Glu Ser Glu Arg Arg Asp Arg Thr His Gly Ser Glu Ile
625                 630                 635                 640

ATT AAT GAT TTA CAA GGT AGA ATA TCT GGC CTA GAA GAA GAT GTA AAG      1968
Ile Asn Asp Leu Gln Gly Arg Ile Ser Gly Leu Glu Glu Asp Val Lys
                645                 650                 655

AAT GGT AAA ATC TTA TTA GCA AAA GTA GAG CTG GAG AAG AGA CAA CTA      2016
Asn Gly Lys Ile Leu Leu Ala Lys Val Glu Leu Glu Lys Arg Gln Leu
            660                 665                 670

CAG GAG AGA TTT ACT GAT TTG GAA AAG GAA AAG AAC AAC ATG GAA ATA      2064
Gln Glu Arg Phe Thr Asp Leu Glu Lys Glu Lys Asn Asn Met Glu Ile
        675                 680                 685

GAT ATG ACA TAC CAA CTA AAA GTC ATA CAG CAA AGT TTA GAA CAA GAA      2112
Asp Met Thr Tyr Gln Leu Lys Val Ile Gln Gln Ser Leu Glu Gln Glu
    690                 695                 700

GAA ACT GAA CAT AAG GCT ACA AAA GCA CGG CTT GCA GAT AAA AAC AAG      2160
Glu Thr Glu His Lys Ala Thr Lys Ala Arg Leu Ala Asp Lys Asn Lys
705                 710                 715                 720

ATT TAT GAA TCC ATT GAA GAA GCT AAA TCA GAA GCC ATG AAA GAA ATG      2208
Ile Tyr Glu Ser Ile Glu Glu Ala Lys Ser Glu Ala Met Lys Glu Met
                725                 730                 735

GAG AAA AAG CTC TCG GAG GAA AGA ACT TTA AAA CAG AAA GTA GAG AAC      2256
Glu Lys Lys Leu Ser Glu Glu Arg Thr Leu Lys Gln Lys Val Glu Asn
            740                 745                 750

TTG TTG CTG GAG GCT GAG AAA AGA TGC TCT ATA TTA GAC TGT GAC CTC      2304
Leu Leu Leu Glu Ala Glu Lys Arg Cys Ser Ile Leu Asp Cys Asp Leu
        755                 760                 765

AAA CAG TCA CAG CAG AAA ATA AAT GAA CTC CTC AAA CAG AAA GAT GTG      2352
Lys Gln Ser Gln Gln Lys Ile Asn Glu Leu Leu Lys Gln Lys Asp Val
    770                 775                 780

CTA AAT GAG GAT GTT AGA AAC TTG ACA TTA AAA ATA GAA CAG GAA ACT      2400
Leu Asn Glu Asp Val Arg Asn Leu Thr Leu Lys Ile Glu Gln Glu Thr
785                 790                 795                 800

CAG AAG CGC TGC CTT ACA CAA AAT GAC TTG AAG ATG CAA ACA CAG CAA      2448
Gln Lys Arg Cys Leu Thr Gln Asn Asp Leu Lys Met Gln Thr Gln Gln
                805                 810                 815

GTT AAC ACA CTA AAA ATG TCA GAA AAG CAG TTA AAG CAA GAG AAT AAT      2496
Val Asn Thr Leu Lys Met Ser Glu Lys Gln Leu Lys Gln Glu Asn Asn
            820                 825                 830

CAT CTC CTA GAA ATG AAA ATG AGC TTG GAA AAA CAG AAT GCT GAA CTT      2544
His Leu Leu Glu Met Lys Met Ser Leu Glu Lys Gln Asn Ala Glu Leu
        835                 840                 845

CGA AAA GAA CGT CAA GAT GCA GAT GGA CAG ATG AAA GAG CTC CAG GAT      2592
Arg Lys Glu Arg Gln Asp Ala Asp Gly Gln Met Lys Glu Leu Gln Asp
    850                 855                 860
```

-continued

```
CAG CTT GAA GCA GAG CAG TAT TTC TCA ACC CTC TAT AAA ACA CAG GTT    2640
Gln Leu Glu Ala Glu Gln Tyr Phe Ser Thr Leu Tyr Lys Thr Gln Val
865                 870                 875                 880

AGG GAA CTT AAG GAA GAA TGT GAA GAA AAG ACC AAA CTT TGT AAA GAA    2688
Arg Glu Leu Lys Glu Glu Cys Glu Glu Lys Thr Lys Leu Cys Lys Glu
                885                 890                 895

TTA CAG CAG AAG AAG CAG GAA TTA CAG GAT GAA AGG GAC TCC TTG GCT    2736
Leu Gln Gln Lys Lys Gln Glu Leu Gln Asp Glu Arg Asp Ser Leu Ala
            900                 905                 910

GCT CAA CTG GAG ATT ACC TTA ACC AAA GCA GAT TCT GAG CAA CTG GCT    2784
Ala Gln Leu Glu Ile Thr Leu Thr Lys Ala Asp Ser Glu Gln Leu Ala
        915                 920                 925

CGT TCA ATT GCT GAG GAA CAG TAT TCT GAT TTG GAA AAA GAG AAG ATC    2832
Arg Ser Ile Ala Glu Glu Gln Tyr Ser Asp Leu Glu Lys Glu Lys Ile
    930                 935                 940

ATG AAA GAG CTG GAG ATC AAA GAG ATG ATG GCT CGA CAC AAA CAG GAA    2880
Met Lys Glu Leu Glu Ile Lys Glu Met Met Ala Arg His Lys Gln Glu
945                 950                 955                 960

CTC ACC GAA AAA GAT GCT ACT ATT GCG TCT CTT GAA GAA ACT AAT AGG    2928
Leu Thr Glu Lys Asp Ala Thr Ile Ala Ser Leu Glu Glu Thr Asn Arg
                965                 970                 975

ACA CTA ACT AGT GAT GTT GCC AAT CTT GCA AAT GAG AAA GAA GAA TTA    2976
Thr Leu Thr Ser Asp Val Ala Asn Leu Ala Asn Glu Lys Glu Glu Leu
            980                 985                 990

AAT AAC AAA CTG AAG GAA GCC CAA GAG CAA CTA TCA AGG TTG AAA GAT    3024
Asn Asn Lys Leu Lys Glu Ala Gln Glu Gln Leu Ser Arg Leu Lys Asp
        995                 1000                1005

GAA GAA ATA AGT GCA GCA GCT ATT AAA GCA CAA TTT GAG AAG CAG CTG    3072
Glu Glu Ile Ser Ala Ala Ala Ile Lys Ala Gln Phe Glu Lys Gln Leu
    1010                1015                1020

TTA ACA GAG AGG ACA CTC AAA ACT CAA GCT GTG AAT AAG TTG GCT GAG    3120
Leu Thr Glu Arg Thr Leu Lys Thr Gln Ala Val Asn Lys Leu Ala Glu
1025                1030                1035                1040

ATC ATG AAT CGA AAG GAA CCT GTT AAG CGT GGT AAT GAC ACA GAT GTG    3168
Ile Met Asn Arg Lys Glu Pro Val Lys Arg Gly Asn Asp Thr Asp Val
                1045                1050                1055

CGG AGA AAA GAA AAG GAG AAT AGA AAG CTA CAT ATG GAA CTT AAA TCT    3216
Arg Arg Lys Glu Lys Glu Asn Arg Lys Leu His Met Glu Leu Lys Ser
            1060                1065                1070

GAA CGC GAA AAA CTG ACC CAG CAG ATG ATC AAG TAT CAG AAA GAA CTG    3264
Glu Arg Glu Lys Leu Thr Gln Gln Met Ile Lys Tyr Gln Lys Glu Leu
        1075                1080                1085

AAT GAA ATG CAG GCT CAA ATA GCT GAA GAG AGT CAG ATT CGA ATT GAA    3312
Asn Glu Met Gln Ala Gln Ile Ala Glu Glu Ser Gln Ile Arg Ile Glu
    1090                1095                1100

CTA CAG ATG ACA CTG GAC AGT AAG GAC AGT GAC ATT GAG CAG CTG CGC    3360
Leu Gln Met Thr Leu Asp Ser Lys Asp Ser Asp Ile Glu Gln Leu Arg
1105                1110                1115                1120

TCC CAG CTC CAG GCC TTG CAC ATT GGT TTG GAT AGT TCC AGT ATA GGC    3408
Ser Gln Leu Gln Ala Leu His Ile Gly Leu Asp Ser Ser Ser Ile Gly
                1125                1130                1135

AGT GGA CCA GGG GAT ACT GAA GCT GAT GAC GGT TTT CCA GAA TCA AGA    3456
Ser Gly Pro Gly Asp Thr Glu Ala Asp Asp Gly Phe Pro Glu Ser Arg
            1140                1145                1150

CTA GAA GGA TGG CTT TCA TTG CCT GTG CGA AAC AAC ACT AAG AAA TTT    3504
Leu Glu Gly Trp Leu Ser Leu Pro Val Arg Asn Asn Thr Lys Lys Phe
        1155                1160                1165

GGA TGG GTT AAA AAG TAT GTG ATT GTA AGC AGT AAG AAG ATC CTT TTC    3552
Gly Trp Val Lys Lys Tyr Val Ile Val Ser Ser Lys Lys Ile Leu Phe
    1170                1175                1180
```

```
TAT GAC AGT GAG CAA GAT AAA GAA CAA TCT AAT CCT TAC ATG GTT TTA      3600
Tyr Asp Ser Glu Gln Asp Lys Glu Gln Ser Asn Pro Tyr Met Val Leu
1185                1190                1195                1200

GAT ATA GAC AAG TTA TTT CAT GTC CGA CCA GTT ACA CAG ACA GAT GTA      3648
Asp Ile Asp Lys Leu Phe His Val Arg Pro Val Thr Gln Thr Asp Val
        1205                1210                1215

TAT AGA GCA GAT GCT AAA GAA ATT CCA AGG ATA TTC CAG ATT CTG TAT      3696
Tyr Arg Ala Asp Ala Lys Glu Ile Pro Arg Ile Phe Gln Ile Leu Tyr
                1220                1225                1230

GCC AAC GAA GGA GAA AGT AAG AAG GAA CAA GAA TTT CCA GTG GAG CCA      3744
Ala Asn Glu Gly Glu Ser Lys Lys Glu Gln Glu Phe Pro Val Glu Pro
                    1235                1240                1245

GTG GGA GAA AAA TCA AAT TAT ATT TGC CAC AAG GGA CAT GAA TTT ATT      3792
Val Gly Glu Lys Ser Asn Tyr Ile Cys His Lys Gly His Glu Phe Ile
1250                1255                1260

CCT ACT CTG TAT CAT TTC CCA ACC AAC TGT GAG GCA TGT ATG AAG CCA      3840
Pro Thr Leu Tyr His Phe Pro Thr Asn Cys Glu Ala Cys Met Lys Pro
1265                1270                1275                1280

TTG TGG CAC ATG TTT AAA CCC CCT CCT GCT TTA GAG TGC CGT CGC TGT      3888
Leu Trp His Met Phe Lys Pro Pro Pro Ala Leu Glu Cys Arg Arg Cys
                1285                1290                1295

CAT ATT AAA TGT CAT AAA GAT CAC ATG GAC AAA AAG GAG GAA ATT ATA      3936
His Ile Lys Cys His Lys Asp His Met Asp Lys Lys Glu Glu Ile Ile
                1300                1305                1310

GCG CCT TGC AAA GTG TAT TAT GAT ATT TCA TCG GCA AAG AAT CTA TTG      3984
Ala Pro Cys Lys Val Tyr Tyr Asp Ile Ser Ser Ala Lys Asn Leu Leu
        1315                1320                1325

TTA TTG GCA AAT TCT ACA GAA GAG CAG CAA AAG TGG GTT AGT CGG TTA      4032
Leu Leu Ala Asn Ser Thr Glu Glu Gln Gln Lys Trp Val Ser Arg Leu
1330                1335                1340

GTG AAA AAA ATA CCT AAA AAG CCT CCA GCT CCA GAC CCT TTT GCA CGG      4080
Val Lys Lys Ile Pro Lys Lys Pro Pro Ala Pro Asp Pro Phe Ala Arg
1345                1350                1355                1360

TCA TCT CCT AGA ACG TCA ATG AAA ATA CAA CAA AAC CAG TCT ATT CGA      4128
Ser Ser Pro Arg Thr Ser Met Lys Ile Gln Gln Asn Gln Ser Ile Arg
                1365                1370                1375

CGG CCA AGT CGA CAA CTT GCT CCA AAC AAA CCA AGC TAACTGCCTT           4174
Arg Pro Ser Arg Gln Leu Ala Pro Asn Lys Pro Ser
                1380                1385

CTGTGAATGC AGTCATTATT TAAGGTGATC ATATTCTTCT AGTTGAAACA AGACTGAAAT    4234

ATGATGGCCC AAAATTTATT AAAAAGTTAT ATTTTCCTGA GAGACTAATA CACATATATA    4294

TTCCCTCTAT TCCTGCAATA TAAATTCTAA ATCTTGAATA GGTTTTCTGG GCTCCTTTGG    4354

AGCAACAAGT TGAACCAACA GTGATTGGTT AATAGAATAA GAATATCATG TGCAACTCTT    4414

CCAGACTTAT TCCATAAAGC TCTCCTAGCA TCACTCACAC TACATTGCAT AAAGGATTTA    4474

GAAGAGTTAC AGAAATCATC TTTTCAGCTT CAACAGAGAC ATTTCACCAG CACATTTGCC    4534

AGAAGAATCT GGGAATGGAT TCCACTACAG TGATAGAGAC TGCGTCTTTA AGAAGTGACC    4594

ATTGTAGTGT GTGTGTGAAC ACACACACAC ACATACACAC ACACACACAC ACACACATAG    4654

TACTGTAATA CTGCAAGAGG GTTTTTTAAC TTCCCACTTT ATTTTTTTAT AAACATTAAT    4714

CAGATATCAT TACTTACTGC AGTTGTAACT ATGCACTTGT ATAAAGCCAT AATGTTGGAG    4774

TTTATATCAC TCATTGTGTG TACCTGCTGG AAGCTGCATG TTCATGTTTA AGCAGTTATT    4834

GTAACAAGAA GTTTGAAGTT AATTATATCA GTTTCTTAAT GCTTTGTAAT AGGCAATTTT    4894

ACCCATTTTG AATGCCTTAA TTTAATTTTT TTCAAGGTAT CCACCCTTTC CTGTATTTAA    4954

AACAAAAAAA AAAGTATTTG CCAGCTCTTA GGATGCAAAT TTGCTTTGCA GAAGAAAATT    5014
```

```
AGTGCACTAT TTTTACACAT AGTAGTTATC ATTGTCGGC                                    5053
```

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Homo sapiens (xi) SEQUENCE DESCRIPTION: SEQ ID NO:3:

```
Cys Lys Arg Gln Leu Gln Glu Arg Phe Thr Asp Leu Glu Lys
1               5                   10
```

(2) INFORMATION FOR SEQ ID NO:4:

(i) SEQUENCE CHARACTERISTICS:
        (A) LENGTH: 1388 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Arg Pro Pro Pro Thr Gly Lys Met Pro Gly Ala Pro Glu Thr
1               5                   10                  15

Ala Pro Gly Asp Gly Ala Gly Ala Ser Arg Gln Arg Lys Leu Glu Ala
                20                  25                  30

Leu Ile Arg Asp Pro Arg Ser Pro Ile Asn Val Glu Ser Leu Leu Asp
            35                  40                  45

Gly Leu Asn Ser Leu Val Leu Asp Leu Asp Phe Pro Ala Leu Arg Lys
    50                  55                  60

Asn Lys Asn Ile Asp Asn Phe Leu Asn Arg Tyr Glu Lys Ile Val Lys
65                  70                  75                  80

Lys Ile Lys Gly Leu Gln Met Lys Ala Glu Asp Tyr Asp Val Val Lys
                85                  90                  95

Val Ile Gly Arg Gly Ala Phe Gly Glu Val Gln Leu Val Arg His Lys
                100                 105                 110

Ala Ser Gln Lys Val Tyr Ala Met Lys Leu Leu Ser Lys Phe Glu Met
            115                 120                 125

Ile Lys Arg Ser Asp Ser Ala Phe Phe Trp Glu Glu Arg Asp Ile Met
    130                 135                 140

Ala Phe Ala Asn Ser Pro Trp Val Val Gln Leu Phe Tyr Ala Phe Gln
145                 150                 155                 160

Asp Asp Arg Tyr Leu Tyr Met Val Met Glu Tyr Met Pro Gly Gly Asp
                165                 170                 175

Leu Val Asn Leu Met Ser Asn Tyr Asp Val Pro Glu Lys Trp Ala Lys
            180                 185                 190

Phe Tyr Thr Ala Glu Val Val Leu Ala Leu Asp Ala Ile His Ser Met
    195                 200                 205

Gly Leu Ile His Arg Asp Val Lys Pro Asp Asn Met Leu Leu Asp Lys
    210                 215                 220

His Gly His Leu Lys Leu Ala Asp Phe Gly Thr Cys Met Lys Met Asp
225                 230                 235                 240

Glu Thr Gly Met Val His Cys Asp Thr Ala Val Gly Thr Pro Asp Tyr
```

```
                245                 250                 255
Ile Ser Pro Glu Val Leu Lys Ser Gln Gly Asp Gly Phe Tyr Gly
            260                 265                 270

Arg Glu Cys Asp Trp Trp Ser Val Gly Val Phe Leu Tyr Glu Met Leu
        275                 280                 285

Val Gly Asp Thr Pro Phe Tyr Ala Asp Ser Leu Val Gly Thr Tyr Ser
        290                 295                 300

Lys Ile Met Asp His Lys Asn Ser Leu Cys Phe Pro Glu Asp Ala Glu
305                 310                 315                 320

Ile Ser Lys His Ala Lys Asn Leu Ile Cys Ala Phe Leu Thr Asp Arg
                325                 330                 335

Glu Val Arg Leu Gly Arg Asn Gly Val Glu Glu Ile Arg Gln His Pro
            340                 345                 350

Phe Phe Lys Asn Asp Gln Trp His Trp Asp Asn Ile Arg Glu Thr Ala
            355                 360                 365

Ala Pro Val Val Pro Glu Leu Ser Ser Asp Ile Asp Ser Ser Asn Phe
        370                 375                 380

Asp Asp Ile Glu Asp Asp Lys Gly Asp Val Glu Thr Phe Pro Ile Pro
385                 390                 395                 400

Lys Ala Phe Val Gly Asn Gln Leu Pro Phe Ile Gly Phe Thr Tyr Tyr
                405                 410                 415

Arg Glu Asn Leu Leu Leu Ser Asp Ser Pro Ser Cys Arg Glu Asn Asp
            420                 425                 430

Ser Ile Gln Ser Arg Lys Asn Glu Glu Ser Gln Glu Ile Gln Lys Lys
            435                 440                 445

Leu Tyr Thr Leu Glu Glu His Leu Ser Asn Glu Met Gln Ala Lys Glu
        450                 455                 460

Glu Leu Glu Gln Lys Cys Lys Ser Val Asn Thr Arg Leu Glu Lys Thr
465                 470                 475                 480

Ala Lys Glu Leu Glu Glu Ile Thr Leu Arg Lys Ser Val Glu Ser
                485                 490                 495

Ala Leu Arg Gln Leu Glu Arg Glu Lys Ala Leu Leu Gln His Lys Asn
            500                 505                 510

Ala Glu Tyr Gln Arg Lys Ala Asp His Glu Ala Asp Lys Lys Arg Asn
        515                 520                 525

Leu Glu Asn Asp Val Asn Ser Leu Lys Asp Gln Leu Glu Asp Leu Lys
        530                 535                 540

Lys Arg Asn Gln Asn Ser Gln Ile Ser Thr Glu Lys Val Asn Gln Leu
545                 550                 555                 560

Gln Arg Gln Leu Asp Glu Thr Asn Ala Leu Leu Arg Thr Glu Ser Asp
            565                 570                 575

Thr Ala Ala Arg Leu Arg Lys Thr Gln Ala Glu Ser Ser Lys Gln Ile
            580                 585                 590

Gln Gln Leu Glu Ser Asn Asn Arg Asp Leu Gln Asp Lys Asn Cys Leu
        595                 600                 605

Leu Glu Thr Ala Lys Leu Lys Leu Glu Lys Glu Phe Ile Asn Leu Gln
        610                 615                 620

Ser Ala Leu Glu Ser Glu Arg Arg Asp Arg Thr His Gly Ser Glu Ile
625                 630                 635                 640

Ile Asn Asp Leu Gln Gly Arg Ile Cys Gly Leu Glu Glu Asp Leu Lys
                645                 650                 655

Asn Gly Lys Ile Leu Leu Ala Lys Val Glu Leu Glu Lys Arg Gln Leu
            660                 665                 670
```

-continued

```
Gln Glu Arg Phe Thr Asp Leu Glu Lys Glu Lys Ser Asn Met Glu Ile
        675                 680                 685

Asp Met Thr Tyr Gln Leu Lys Val Ile Gln Gln Ser Leu Glu Gln Glu
        690                 695                 700

Glu Ala Glu His Lys Ala Thr Lys Ala Arg Leu Ala Asp Lys Asn Lys
705                 710                 715                 720

Ile Tyr Glu Ser Ile Glu Glu Ala Lys Ser Glu Ala Met Lys Glu Met
                725                 730                 735

Glu Lys Lys Leu Leu Glu Glu Arg Thr Leu Lys Gln Lys Val Glu Asn
                740                 745                 750

Leu Leu Leu Glu Ala Glu Lys Arg Cys Ser Leu Leu Asp Cys Asp Leu
            755                 760                 765

Lys Gln Ser Gln Gln Lys Ile Asn Glu Leu Leu Lys Gln Lys Asp Val
        770                 775                 780

Leu Asn Glu Asp Val Arg Asn Leu Thr Leu Lys Ile Glu Gln Glu Thr
785                 790                 795                 800

Gln Lys Arg Cys Leu Thr Gln Asn Asp Leu Lys Met Gln Thr Gln Gln
                805                 810                 815

Val Asn Thr Leu Lys Met Ser Glu Lys Gln Leu Lys Gln Glu Asn Asn
                820                 825                 830

His Leu Met Glu Met Lys Met Asn Leu Glu Lys Gln Asn Ala Glu Leu
            835                 840                 845

Arg Lys Glu Arg Gln Asp Ala Asp Gly Gln Met Lys Glu Leu Gln Asp
850                 855                 860

Gln Leu Glu Ala Glu Gln Tyr Phe Ser Thr Leu Tyr Lys Thr Gln Val
865                 870                 875                 880

Arg Glu Leu Lys Glu Glu Cys Glu Glu Lys Thr Lys Leu Gly Lys Glu
                885                 890                 895

Leu Gln Gln Lys Lys Gln Glu Leu Gln Asp Glu Arg Asp Ser Leu Ala
                900                 905                 910

Ala Gln Leu Glu Ile Thr Leu Thr Lys Ala Asp Ser Glu Gln Leu Ala
            915                 920                 925

Arg Ser Ile Ala Glu Glu Gln Tyr Ser Asp Leu Glu Lys Glu Lys Ile
930                 935                 940

Met Lys Glu Leu Glu Ile Lys Glu Met Met Ala Arg His Lys Gln Glu
945                 950                 955                 960

Leu Thr Glu Lys Asp Ala Thr Ile Ala Ser Leu Glu Glu Thr Asn Arg
                965                 970                 975

Thr Leu Thr Ser Asp Val Ala Asn Leu Ala Asn Glu Lys Glu Glu Leu
            980                 985                 990

Asn Asn Lys Leu Lys Asp Val Gln Glu Gln Leu Ser Arg Leu Lys Asp
        995                 1000                1005

Glu Glu Ile Ser Ala Ala Ile Lys Ala Gln Phe Glu Lys Gln Leu
    1010                1015                1020

Leu Thr Glu Arg Thr Leu Lys Thr Gln Ala Val Asn Lys Leu Ala Glu
1025                1030                1035                1040

Ile Met Asn Arg Lys Glu Pro Val Lys Arg Gly Asn Asp Thr Asp Val
                1045                1050                1055

Arg Arg Lys Glu Lys Glu Asn Arg Lys Leu His Met Glu Leu Lys Ser
            1060                1065                1070

Glu Arg Glu Lys Leu Thr Gln Gln Met Ile Lys Tyr Gln Lys Glu Leu
        1075                1080                1085

Asn Glu Met Gln Ala Gln Ile Ala Glu Glu Ser Gln Ile Arg Ile Glu
        1090                1095                1100
```

```
Leu Gln Met Thr Leu Asp Ser Lys Asp Ser Asp Ile Glu Gln Leu Arg
1105                1110                1115                1120

Ser Gln Leu Gln Ala Leu His Ile Gly Leu Asp Ser Ser Ile Gly
        1125                1130                1135

Ser Gly Pro Gly Asp Ala Glu Ala Asp Asp Gly Phe Pro Glu Ser Arg
        1140                1145                1150

Leu Glu Gly Trp Leu Ser Leu Pro Val Arg Asn Asn Thr Lys Lys Phe
        1155                1160                1165

Gly Trp Val Lys Lys Tyr Val Ile Val Ser Ser Lys Lys Ile Leu Phe
        1170                1175                1180

Tyr Asp Ser Glu Gln Asp Lys Glu Gln Ser Asn Pro Tyr Met Val Leu
1185                1190                1195                1200

Asp Ile Asp Lys Leu Phe His Val Arg Pro Val Thr Gln Thr Asp Val
                1205                1210                1215

Tyr Arg Ala Asp Ala Lys Glu Ile Pro Arg Ile Phe Gln Ile Leu Tyr
        1220                1225                1230

Ala Asn Glu Gly Glu Ser Lys Lys Glu Gln Glu Phe Pro Val Glu Pro
        1235                1240                1245

Val Gly Glu Lys Ser Asn Tyr Ile Cys His Lys Gly His Glu Phe Ile
        1250                1255                1260

Pro Thr Leu Tyr His Phe Pro Thr Asn Cys Glu Ala Cys Met Lys Pro
1265                1270                1275                1280

Leu Trp His Met Phe Lys Pro Pro Pro Ala Leu Glu Cys Arg Arg Cys
        1285                1290                1295

His Ile Lys Cys His Lys Asp His Met Asp Lys Lys Glu Glu Ile Ile
        1300                1305                1310

Ala Pro Cys Lys Val Tyr Tyr Asp Ile Ser Thr Ala Lys Asn Leu Leu
        1315                1320                1325

Leu Leu Ala Asn Ser Thr Glu Glu Gln Gln Lys Trp Val Ser Arg Leu
        1330                1335                1340

Val Lys Lys Ile Pro Lys Lys Pro Pro Ala Pro Asp Pro Phe Ala Arg
1345                1350                1355                1360

Ser Ser Pro Arg Thr Ser Met Lys Ile Gln Gln Asn Gln Ser Ile Arg
                1365                1370                1375

Arg Pro Ser Arg Gln Leu Ala Pro Asn Lys Pro Ser
        1380                1385

(2) INFORMATION FOR SEQ ID NO:5:

(i) SEQUENCE CHARACTERISTICS:
        (A) LENGTH: 4363 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION: 1..4164

(xi) SEQUENCE DESCRIPTION: SEQ ID NO:5:

ATG AGC CGG CCC CCG CCG ACG GGG AAA ATG CCC GGC GCC CCC GAG ACC        48
Met Ser Arg Pro Pro Pro Thr Gly Lys Met Pro Gly Ala Pro Glu Thr
1                5                  10                  15

GCG CCG GGG GAC GGG GCA GGC GCG AGC CGC CAG AGG AAG CTG GAG GCG        96
```

-continued

```
Ala Pro Gly Asp Gly Ala Gly Ala Ser Arg Gln Arg Lys Leu Glu Ala
         20                  25                  30

CTG ATC CGA GAC CCT CGC TCC CCC ATC AAC GTG GAG AGC TTG CTG GAT       144
Leu Ile Arg Asp Pro Arg Ser Pro Ile Asn Val Glu Ser Leu Leu Asp
             35                  40                  45

GGC TTA AAT TCC TTG GTC CTT GAT TTA GAT TTT CCT GCT TTG AGG AAA       192
Gly Leu Asn Ser Leu Val Leu Asp Leu Asp Phe Pro Ala Leu Arg Lys
 50                  55                  60

AAC AAG AAC ATA GAT AAT TTC TTA AAT AGA TAT GAG AAA ATT GTG AAA       240
Asn Lys Asn Ile Asp Asn Phe Leu Asn Arg Tyr Glu Lys Ile Val Lys
 65                  70                  75                  80

AAA ATC AAA GGT CTA CAG ATG AAG GCA GAA GAC TAT GAT GTT GTA AAA       288
Lys Ile Lys Gly Leu Gln Met Lys Ala Glu Asp Tyr Asp Val Val Lys
                 85                  90                  95

GTT ATT GGA AGA GGT GCT TTT GGT GAA GTG CAG TTG GTT CGT CAC AAG       336
Val Ile Gly Arg Gly Ala Phe Gly Glu Val Gln Leu Val Arg His Lys
             100                 105                 110

GCA TCG CAG AAG GTT TAT GCT ATG AAG CTT CTT AGT AAG TTT GAA ATG       384
Ala Ser Gln Lys Val Tyr Ala Met Lys Leu Leu Ser Lys Phe Glu Met
         115                 120                 125

ATA AAA AGA TCA GAT TCT GCC TTT TTT TGG GAA GAA AGA GAT ATT ATG       432
Ile Lys Arg Ser Asp Ser Ala Phe Phe Trp Glu Glu Arg Asp Ile Met
 130                 135                 140

GCC TTT GCC AAT AGC CCC TGG GTG GTT CAG CTT TTT TAT GCC TTT CAA       480
Ala Phe Ala Asn Ser Pro Trp Val Val Gln Leu Phe Tyr Ala Phe Gln
145                 150                 155                 160

GAT GAT AGG TAT CTG TAC ATG GTA ATG GAG TAC ATG CCT GGT GGA GAC       528
Asp Asp Arg Tyr Leu Tyr Met Val Met Glu Tyr Met Pro Gly Gly Asp
                 165                 170                 175

CTT GTA AAC CTT ATG AGT AAT TAT GAT GTG CCT GAA AAA TGG GCC AAA       576
Leu Val Asn Leu Met Ser Asn Tyr Asp Val Pro Glu Lys Trp Ala Lys
             180                 185                 190

TTT TAC ACT GCT GAA GTT GTT CTT GCT CTG GAT GCA ATA CAC TCC ATG       624
Phe Tyr Thr Ala Glu Val Val Leu Ala Leu Asp Ala Ile His Ser Met
         195                 200                 205

GGT TTA ATA CAC AGA GAT GTG AAG CCT GAC AAC ATG CTC TTG GAT AAA       672
Gly Leu Ile His Arg Asp Val Lys Pro Asp Asn Met Leu Leu Asp Lys
 210                 215                 220

CAT GGA CAT CTA AAA TTA GCA GAT TTT GGC ACG TGT ATG AAG ATG GAT       720
His Gly His Leu Lys Leu Ala Asp Phe Gly Thr Cys Met Lys Met Asp
225                 230                 235                 240

GAA ACA GGC ATG GTA CAT TGT GAT ACA GCA GTT GGA ACA CCG GAT TAT       768
Glu Thr Gly Met Val His Cys Asp Thr Ala Val Gly Thr Pro Asp Tyr
                 245                 250                 255

ATA TCA CCT GAG GTT CTG AAA TCA CAA GGG GGT GAT GGT TTC TAT GGG       816
Ile Ser Pro Glu Val Leu Lys Ser Gln Gly Gly Asp Gly Phe Tyr Gly
             260                 265                 270

CGA GAA TGT GAT TGG TGG TCT GTA GGT GTT TTC CTT TAT GAG ATG CTA       864
Arg Glu Cys Asp Trp Trp Ser Val Gly Val Phe Leu Tyr Glu Met Leu
         275                 280                 285

GTG GGG GAT ACT CCA TTT TAT GCG GAT TCA CTT GTA GGA ACA TAT AGC       912
Val Gly Asp Thr Pro Phe Tyr Ala Asp Ser Leu Val Gly Thr Tyr Ser
 290                 295                 300

AAA ATT ATG GAT CAT AAG AAT TCA CTG TGT TTC CCT GAA GAT GCA GAA       960
Lys Ile Met Asp His Lys Asn Ser Leu Cys Phe Pro Glu Asp Ala Glu
305                 310                 315                 320

ATT TCC AAA CAT GCA AAG AAT CTC ATC TGT GCT TTC TTA ACA GAT AGG      1008
Ile Ser Lys His Ala Lys Asn Leu Ile Cys Ala Phe Leu Thr Asp Arg
                 325                 330                 335

GAG GTA CGA CTT GGG AGA AAT GGG GTG GAA GAA ATC AGA CAG CAT CCT      1056
```

```
                Glu Val Arg Leu Gly Arg Asn Gly Val Glu Glu Ile Arg Gln His Pro
                                340                 345                 350

TTC TTT AAG AAT GAT CAG TGG CAT TGG GAT AAC ATA AGA GAA ACG GCA             1104
Phe Phe Lys Asn Asp Gln Trp His Trp Asp Asn Ile Arg Glu Thr Ala
            355                 360                 365

GCT CCT GTA GTA CCT GAA CTC AGC AGT GAC ATA GAC AGC AGC AAT TTC             1152
Ala Pro Val Val Pro Glu Leu Ser Ser Asp Ile Asp Ser Ser Asn Phe
370                 375                 380

GAT GAC ATT GAA GAT GAC AAA GGA GAT GTA GAA ACC TTC CCA ATT CCT             1200
Asp Asp Ile Glu Asp Asp Lys Gly Asp Val Glu Thr Phe Pro Ile Pro
385                 390                 395                 400

AAA GCT TTT GTT GGA AAT CAG CTG CCT TTC ATC GGA TTT ACC TAC TAT             1248
Lys Ala Phe Val Gly Asn Gln Leu Pro Phe Ile Gly Phe Thr Tyr Tyr
            405                 410                 415

AGA GAA AAT TTA TTA TTA AGT GAC TCT CCA TCT TGT AGA GAA AAT GAT             1296
Arg Glu Asn Leu Leu Leu Ser Asp Ser Pro Ser Cys Arg Glu Asn Asp
            420                 425                 430

TCC ATA CAA TCA AGG AAA AAT GAA GAA AGT CAA GAG ATT CAG AAA AAA             1344
Ser Ile Gln Ser Arg Lys Asn Glu Glu Ser Gln Glu Ile Gln Lys Lys
            435                 440                 445

CTG TAT ACA TTA GAA GAA CAT CTT AGC AAT GAG ATG CAA GCC AAA GAG             1392
Leu Tyr Thr Leu Glu Glu His Leu Ser Asn Glu Met Gln Ala Lys Glu
            450                 455                 460

GAA CTG GAA CAG AAG TGC AAA TCT GTT AAT ACT CGC CTA GAA AAA ACA             1440
Glu Leu Glu Gln Lys Cys Lys Ser Val Asn Thr Arg Leu Glu Lys Thr
465                 470                 475                 480

GCA AAG GAG CTA GAA GAG GAG ATT ACC TTA CGG AAA AGT GTG GAA TCA             1488
Ala Lys Glu Leu Glu Glu Glu Ile Thr Leu Arg Lys Ser Val Glu Ser
            485                 490                 495

GCA TTA AGA CAG TTA GAA AGA GAA AAG GCG CTT CTT CAG CAC AAA AAT             1536
Ala Leu Arg Gln Leu Glu Arg Glu Lys Ala Leu Leu Gln His Lys Asn
            500                 505                 510

GCA GAA TAT CAG AGG AAA GCT GAT CAT GAA GCA GAC AAA AAA CGA AAT             1584
Ala Glu Tyr Gln Arg Lys Ala Asp His Glu Ala Asp Lys Lys Arg Asn
            515                 520                 525

TTG GAA AAT GAT GTT AAC AGC TTA AAA GAT CAA CTT GAA GAT TTG AAA             1632
Leu Glu Asn Asp Val Asn Ser Leu Lys Asp Gln Leu Glu Asp Leu Lys
            530                 535                 540

AAA AGA AAT CAA AAC TCT CAA ATA TCC ACT GAG AAA GTG AAT CAA CTC             1680
Lys Arg Asn Gln Asn Ser Gln Ile Ser Thr Glu Lys Val Asn Gln Leu
545                 550                 555                 560

CAG AGA CAA CTG GAT GAA ACC AAT GCT TTA CTG CGA ACA GAG TCT GAT             1728
Gln Arg Gln Leu Asp Glu Thr Asn Ala Leu Leu Arg Thr Glu Ser Asp
            565                 570                 575

ACT GCA GCC CGG TTA AGG AAA ACC CAG GCA GAA AGT TCA AAA CAG ATT             1776
Thr Ala Ala Arg Leu Arg Lys Thr Gln Ala Glu Ser Ser Lys Gln Ile
            580                 585                 590

CAG CAG CTG GAA TCT AAC AAT AGA GAT CTA CAA GAT AAA AAC TGC CTG             1824
Gln Gln Leu Glu Ser Asn Asn Arg Asp Leu Gln Asp Lys Asn Cys Leu
            595                 600                 605

CTG GAG ACT GCC AAG TTA AAA CTT GAA AAG GAA TTT ATC AAT CTT CAG             1872
Leu Glu Thr Ala Lys Leu Lys Leu Glu Lys Glu Phe Ile Asn Leu Gln
            610                 615                 620

TCA GCT CTA GAA TCT GAA AGG AGG GAT CGA ACC CAT GGA TCA GAG ATA             1920
Ser Ala Leu Glu Ser Glu Arg Arg Asp Arg Thr His Gly Ser Glu Ile
625                 630                 635                 640

ATT AAT GAT TTA CAA GGT AGA ATA TGT GGC CTA GAA GAA GAT TTA AAG             1968
Ile Asn Asp Leu Gln Gly Arg Ile Cys Gly Leu Glu Glu Asp Leu Lys
            645                 650                 655

AAC GGC AAA ATC TTA CTA GCG AAA GTA GAA CTG GAG AAG AGA CAA CTT             2016
```

```
                Asn Gly Lys Ile Leu Leu Ala Lys Val Glu Leu Glu Lys Arg Gln Leu
                            660                 665                 670

CAG GAG AGA TTT ACT GAT TTG GAA AAG GAA AAA AGC AAC ATG GAA ATA          2064
Gln Glu Arg Phe Thr Asp Leu Glu Lys Glu Lys Ser Asn Met Glu Ile
            675                 680                 685

GAT ATG ACA TAC CAA CTA AAA GTT ATA CAG CAG AGC CTA GAA CAA GAA          2112
Asp Met Thr Tyr Gln Leu Lys Val Ile Gln Gln Ser Leu Glu Gln Glu
690                 695                 700

GAA GCT GAA CAT AAG GCC ACA AAG GCA CGA CTA GCA GAT AAA AAT AAG          2160
Glu Ala Glu His Lys Ala Thr Lys Ala Arg Leu Ala Asp Lys Asn Lys
705                 710                 715                 720

ATC TAT GAG TCC ATC GAA GAA GCC AAA TCA GAA GCC ATG AAA GAA ATG          2208
Ile Tyr Glu Ser Ile Glu Glu Ala Lys Ser Glu Ala Met Lys Glu Met
                725                 730                 735

GAG AAG AAG CTC TTG GAG GAA AGA ACT TTA AAA CAG AAA GTG GAG AAC          2256
Glu Lys Lys Leu Leu Glu Glu Arg Thr Leu Lys Gln Lys Val Glu Asn
            740                 745                 750

CTA TTG CTA GAA GCT GAG AAA AGA TGT TCT CTA TTA GAC TGT GAC CTC          2304
Leu Leu Leu Glu Ala Glu Lys Arg Cys Ser Leu Leu Asp Cys Asp Leu
        755                 760                 765

AAA CAG TCA CAG CAG AAA ATA AAT GAG CTC CTT AAA CAG AAA GAT GTG          2352
Lys Gln Ser Gln Gln Lys Ile Asn Glu Leu Leu Lys Gln Lys Asp Val
    770                 775                 780

CTA AAT GAG GAT GTT AGA AAC CTG ACA TTA AAA ATA GAG CAA GAA ACT          2400
Leu Asn Glu Asp Val Arg Asn Leu Thr Leu Lys Ile Glu Gln Glu Thr
785                 790                 795                 800

CAG AAG CGC TGC CTT ACA CAA AAT GAC CTG AAG ATG CAA ACA CAA CAG          2448
Gln Lys Arg Cys Leu Thr Gln Asn Asp Leu Lys Met Gln Thr Gln Gln
                805                 810                 815

GTT AAC ACA CTA AAA ATG TCA GAA AAG CAG TTA AAG CAA GAA AAT AAC          2496
Val Asn Thr Leu Lys Met Ser Glu Lys Gln Leu Lys Gln Glu Asn Asn
            820                 825                 830

CAT CTC ATG GAA ATG AAA ATG AAC TTG GAA AAA CAA AAT GCT GAA CTT          2544
His Leu Met Glu Met Lys Met Asn Leu Glu Lys Gln Asn Ala Glu Leu
        835                 840                 845

CGA AAA GAA CGT CAG GAT GCA GAT GGG CAA ATG AAA GAG CTC CAG GAT          2592
Arg Lys Glu Arg Gln Asp Ala Asp Gly Gln Met Lys Glu Leu Gln Asp
    850                 855                 860

CAG CTC GAA GCA GAA CAG TAT TTC TCA ACC CTT TAT AAA ACA CAA GTT          2640
Gln Leu Glu Ala Glu Gln Tyr Phe Ser Thr Leu Tyr Lys Thr Gln Val
865                 870                 875                 880

AGG GAG CTT AAA GAA GAA TGT GAA GAA AAG ACC AAA CTT GGT AAA GAA          2688
Arg Glu Leu Lys Glu Glu Cys Glu Glu Lys Thr Lys Leu Gly Lys Glu
                885                 890                 895

TTG CAG CAG AAG AAA CAG GAA TTA CAG GAT GAA CGG GAC TCT TTG GCT          2736
Leu Gln Gln Lys Lys Gln Glu Leu Gln Asp Glu Arg Asp Ser Leu Ala
            900                 905                 910

GCC CAA CTG GAG ATC ACC TTG ACC AAA GCA GAT TCT GAG CAA CTG GCT          2784
Ala Gln Leu Glu Ile Thr Leu Thr Lys Ala Asp Ser Glu Gln Leu Ala
        915                 920                 925

CGT TCA ATT GCT GAA GAA CAA TAT TCT GAT TTG GAA AAA GAG AAG ATC          2832
Arg Ser Ile Ala Glu Glu Gln Tyr Ser Asp Leu Glu Lys Glu Lys Ile
    930                 935                 940

ATG AAA GAG CTG GAG ATC AAA GAG ATG ATG GCT AGA CAC AAA CAG GAA          2880
Met Lys Glu Leu Glu Ile Lys Glu Met Met Ala Arg His Lys Gln Glu
945                 950                 955                 960

CTT ACG GAA AAA GAT GCT ACA ATT GCT TCT CTT GAG GAA ACT AAT AGG          2928
Leu Thr Glu Lys Asp Ala Thr Ile Ala Ser Leu Glu Glu Thr Asn Arg
                965                 970                 975

ACA CTA ACT AGT GAT GTT GCC AAT CTT GCA AAT GAG AAA GAA GAA TTA          2976
```

-continued

```
        Thr Leu Thr Ser Asp Val Ala Asn Leu Ala Asn Glu Lys Glu Glu Leu
                    980                 985                 990

AAT AAC AAA TTG AAA GAT GTT CAA GAG CAA CTG TCA AGA TTG AAA GAT        3024
Asn Asn Lys Leu Lys Asp Val Gln Glu Gln Leu Ser Arg Leu Lys Asp
        995                 1000                1005

GAA GAA ATA AGC GCA GCA GCT ATT AAA GCA CAG TTT GAG AAG CAG CTA        3072
Glu Glu Ile Ser Ala Ala Ala Ile Lys Ala Gln Phe Glu Lys Gln Leu
        1010                1015                1020

TTA ACA GAA AGA ACA CTC AAA ACT CAA GCT GTG AAT AAG TTG GCT GAG        3120
Leu Thr Glu Arg Thr Leu Lys Thr Gln Ala Val Asn Lys Leu Ala Glu
1025                1030                1035                1040

ATC ATG AAT CGA AAA GAA CCT GTC AAG CGT GGT AAT GAC ACA GAT GTG        3168
Ile Met Asn Arg Lys Glu Pro Val Lys Arg Gly Asn Asp Thr Asp Val
                1045                1050                1055

CGG AGA AAA GAG AAG GAG AAT AGA AAG CTA CAT ATG GAG CTT AAA TCT        3216
Arg Arg Lys Glu Lys Glu Asn Arg Lys Leu His Met Glu Leu Lys Ser
                1060                1065                1070

GAA CGT GAG AAA TTG ACC CAG CAG ATG ATC AAG TAT CAG AAA GAA CTG        3264
Glu Arg Glu Lys Leu Thr Gln Gln Met Ile Lys Tyr Gln Lys Glu Leu
                1075                1080                1085

AAT GAA ATG CAG GCA CAA ATA GCT GAA GAG AGC CAG ATT CGA ATT GAA        3312
Asn Glu Met Gln Ala Gln Ile Ala Glu Glu Ser Gln Ile Arg Ile Glu
                1090                1095                1100

CTG CAG ATG ACA TTG GAC AGT AAA GAC AGT GAC ATT GAG CAG CTG CGG        3360
Leu Gln Met Thr Leu Asp Ser Lys Asp Ser Asp Ile Glu Gln Leu Arg
1105                1110                1115                1120

TCA CAA CTC CAA GCC TTG CAT ATT GGT CTG GAT AGT TCC AGT ATA GGC        3408
Ser Gln Leu Gln Ala Leu His Ile Gly Leu Asp Ser Ser Ser Ile Gly
                1125                1130                1135

AGT GGA CCA GGG GAT GCT GAG GCA GAT GAT GGG TTT CCA GAA TCA AGA        3456
Ser Gly Pro Gly Asp Ala Glu Ala Asp Asp Gly Phe Pro Glu Ser Arg
                1140                1145                1150

TTA GAA GGA TGG CTT TCA TTG CCT GTA CGA AAC AAC ACT AAG AAA TTT        3504
Leu Glu Gly Trp Leu Ser Leu Pro Val Arg Asn Asn Thr Lys Lys Phe
                1155                1160                1165

GGA TGG GTT AAA AAG TAT GTG ATT GTA AGC AGT AAG AAG ATT CTT TTC        3552
Gly Trp Val Lys Lys Tyr Val Ile Val Ser Ser Lys Lys Ile Leu Phe
        1170                1175                1180

TAT GAC AGT GAA CAA GAT AAA GAA CAA TCC AAT CCT TAC ATG GTT TTA        3600
Tyr Asp Ser Glu Gln Asp Lys Glu Gln Ser Asn Pro Tyr Met Val Leu
1185                1190                1195                1200

GAT ATA GAC AAG TTA TTT CAT GTC CGA CCA GTT ACA CAG ACA GAT GTG        3648
Asp Ile Asp Lys Leu Phe His Val Arg Pro Val Thr Gln Thr Asp Val
                1205                1210                1215

TAT AGA GCA GAT GCT AAA GAA ATT CCA AGG ATA TTC CAG ATT CTG TAT        3696
Tyr Arg Ala Asp Ala Lys Glu Ile Pro Arg Ile Phe Gln Ile Leu Tyr
                1220                1225                1230

GCC AAT GAA GGA GAA AGT AAG AAG GAA CAA GAA TTT CCA GTG GAG CCA        3744
Ala Asn Glu Gly Glu Ser Lys Lys Glu Gln Glu Phe Pro Val Glu Pro
                1235                1240                1245

GTT GGA GAA AAA TCT AAT TAT ATT TGC CAC AAG GGA CAT GAG TTT ATT        3792
Val Gly Glu Lys Ser Asn Tyr Ile Cys His Lys Gly His Glu Phe Ile
        1250                1255                1260

CCT ACT CTT TAT CAT TTC CCA ACC AAC TGT GAG GCT TGT ATG AAG CCC        3840
Pro Thr Leu Tyr His Phe Pro Thr Asn Cys Glu Ala Cys Met Lys Pro
1265                1270                1275                1280

CTG TGG CAC ATG TTT AAG CCT CCT CCT GCT TTG GAG TGC CGC CGT TGC        3888
Leu Trp His Met Phe Lys Pro Pro Pro Ala Leu Glu Cys Arg Arg Cys
                1285                1290                1295

CAT ATT AAG TGT CAT AAA GAT CAT ATG GAC AAA AAG GAG GAG ATT ATA        3936
```

```
His Ile Lys Cys His Lys Asp His Met Asp Lys Lys Glu Glu Ile Ile
        1300                1305                1310

GCA CCT TGC AAA GTA TAT TAT GAT ATT TCA ACG GCA AAG AAT CTG TTA    3984
Ala Pro Cys Lys Val Tyr Tyr Asp Ile Ser Thr Ala Lys Asn Leu Leu
        1315                1320                1325

TTA CTA GCA AAT TCT ACA GAA GAG CAG CAG AAG TGG GTT AGT CGG TTG    4032
Leu Leu Ala Asn Ser Thr Glu Glu Gln Gln Lys Trp Val Ser Arg Leu
        1330                1335                1340

GTG AAA AAG ATA CCT AAA AAG CCC CCA GCT CCA GAC CCT TTT GCC CGA    4080
Val Lys Lys Ile Pro Lys Lys Pro Pro Ala Pro Asp Pro Phe Ala Arg
1345            1350                1355                1360

TCA TCT CCT AGA ACT TCA ATG AAG ATA CAG CAA AAC CAG TCT ATT AGA    4128
Ser Ser Pro Arg Thr Ser Met Lys Ile Gln Gln Asn Gln Ser Ile Arg
                1365                1370                1375

CGG CCA AGT CGA CAG CTT GCC CCA AAC AAA CCT AGC TAACTGCCTT         4174
Arg Pro Ser Arg Gln Leu Ala Pro Asn Lys Pro Ser
        1380                1385

CTATGAAAGC AGTCATTATT CAAGGTGATC GTATTCTTCC AGTGAAAACA AGACTGAAAT  4234

ATGATGACCC CATGGTACCC GGATCCTCGA ATCTTTTGCT TTTTACCCTG GAAGAAATAC  4294

TCATAAGCCA CCTCTGTAAT CGGATCCCCG GGTACCGAAA TACTCATAAG CCACCTCTGT  4354

AATCGGATC                                                         4363

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..3
        (D) OTHER INFORMATION: /product= "aliphatic amino acids"

(xi) SEQUENCE DESCRIPTION: SEQ ID NO:6:

Cys Xaa Xaa Leu
1

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

ATAAGGATCC CTACTAAGTG ACTCTCCATC TTG                                33

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"
```

(xi) SEQUENCE DESCRIPTION: SEQ ID NO:8:

TATAGGATCC TTAACTGCCT ATACTGGAAC TATCC                35

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

AATAGGATCC GATTTAACCG CCACCATGTC G                31

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

ATAAGGATCC TCAGTCATCT TTGTCTTTCG CTC                33

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

CATTTTCATT TCTAGGAGAT GATTATTCTC TTGCTTTAAC                40

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

AAAAAGCACT TCTTCAGCAC AAAAATGCAG AATATCAGCG                40

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

CCTTTGTCAT CTTCAATGTC ATCGAAATTG                                30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

CGTGTATGAA GATGGATGAA ACAGGCATGG                                30

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

TTGCGGCCGC TAAAGATCAT GAAAGAGCTG GAGATC                         36

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

TAGCGGCCGC AACATATGTA GCTTTCTATT CTC                            33